United States Patent [19]

Suzuki et al.

[11] Patent Number: 5,484,920

[45] Date of Patent: Jan. 16, 1996

[54] THERAPEUTIC AGENT FOR PARKINSON'S DISEASE

[75] Inventors: Fumio Suzuki, Mishima; Junichi Shimada, Shizuoka; Nobuaki Koike, Shizuoka; Joji Nakamura, Shizuoka; Shizuo Shioazaki, Fuji; Shunji Ichikawa, Shizuoka; Akio Ishii, Shizuoka; Hiromi Nonaka, Shizuoka, all of Japan

[73] Assignee: Kyowa Hakko Kogyo Co., Ltd., Tokyo, Japan

[21] Appl. No.: 133,510

[22] Filed: Oct. 7, 1993

Related U.S. Application Data

[63] Continuation-in-part of Ser. No. 42,535, Apr. 5, 1993, abandoned.

[30] Foreign Application Priority Data

Apr. 8, 1992 [JP] Japan .................................. 4-87715
Sep. 25, 1992 [JP] Japan .................................. 4-257834

[51] Int. Cl.$^6$ ........................ C07D 473/06; A61K 31/52
[52] U.S. Cl. ........................ 544/268; 544/264; 544/265
[58] Field of Search ........................ 544/268; 514/265

[56] References Cited

U.S. PATENT DOCUMENTS

| | | | |
|---|---|---|---|
| 2,729,642 | 1/1956 | Burgison | 260/256 |
| 3,624,215 | 11/1971 | Stein et al. | 424/253 |
| 3,624,216 | 11/1971 | Stein et al. | 424/253 |
| 3,641,010 | 2/1972 | Schweiss et al. | 260/240 |
| 3,900,474 | 8/1975 | Ginger et al. | 260/256 |
| 4,452,788 | 6/1984 | Bristol et al. | 424/253 |
| 4,548,820 | 10/1985 | Regnier et al. | 514/255 |
| 4,612,315 | 9/1986 | Jacobson et al. | 514/263 |
| 4,696,932 | 9/1987 | Jacobson et al. | 514/263 |
| 4,755,517 | 7/1988 | Bruns et al. | 514/263 |
| 4,879,296 | 11/1989 | Daluge et al. | 514/263 |
| 4,968,672 | 11/1990 | Jacobson et al. | 514/46 |
| 4,981,857 | 1/1991 | Daluge et al. | 514/263 |
| 5,098,996 | 3/1992 | Jacobson et al. | 530/303 |
| 5,173,491 | 12/1992 | Kamoun et al. | 514/265 |
| 5,175,291 | 12/1992 | Kufner-Muhl | 544/267 |
| 5,248,770 | 9/1993 | Jacobson et al. | 536/26.1 |

FOREIGN PATENT DOCUMENTS

| | | | |
|---|---|---|---|
| 0215736 | 3/1987 | European Pat. Off. | 473/12 |
| 0267607 | 5/1988 | European Pat. Off. | 473/6 |
| 415456A2 | 6/1991 | European Pat. Off. | 473/6 |
| 0512486 | 10/1971 | Switzerland | 57/40 |
| 2107709 | 5/1983 | United Kingdom | 473/8 |
| 2135311 | 8/1984 | United Kingdom | 473/6 |
| 0389282 | 3/1990 | United Kingdom . | |
| 9200297 | 1/1992 | WIPO . | |
| 9206976 | 4/1992 | WIPO . | |

OTHER PUBLICATIONS

Jacobson, K. A. et al. "Structure–Activity Relationships of 8–Styrylxanthines as A$_2$–Selective Adenosine Antagonists," J. Med. Chem. 36: 1333–1342, 1993.

Ossowska et al. Eur. J. Pharmacol., 182: 327–334, 1990.

Goodman, et al. In: Pharmacological Basis of Therapeutics, Gilman A. G. Ed. 8th Ed., Pergamon Press, N.Y., Chap. 20, 1990.

Erickson R. H. et al. "1,3,8–Trisubstituted Xanthines. Effects of Substitution Pattern upon Adenosine Receptor A$_1$/A$_2$ Affinity". J. Med. Chem., 34, col. 1431–1435 (1991).

Kaupp, G. und Ringer, E. "Multifunktionelle Photoaddition von Stilben an Coffeinderivate und Benzothiazole." Chem. Ber., 119, col. 1525–1539 (1986).

Lugovkin, B. P. "Condensation of Isocaffeine–8–carboxaldehyde with Alkyl Iodides of Heterocyclic Bases." Chem. Abst., 60, col. 1741–1742 (1964).

Heikkila, et al. "Dopaminegeric Neurotoxicity of 1–methyl–4–phenyl–1,2,5,6–tetrahydropyridine in mice", Science 224: 1451–1453 (1984).

Langston, et al. "Chronic Parkinsonism in humans due to a product of Meperidine–analog synthesis", Science 219: 979–980 (1983).

Jiang, et al. "Adenosine receptor antagonists potentiate dopamine receptor agonist—induced rotational behavior in 6–hydroxydopamine—lesioned rats", Brain Res. 613:347–351 (1993).

Primary Examiner—Mukund J. Shah
Assistant Examiner—Pavanaram K. Sripada
Attorney, Agent, or Firm—White & Case

[57] ABSTRACT

Agents for the treatment of Parkinson's disease contain, as an active ingredient, a xanthine derivative or a pharmaceutically acceptable salt thereof. The xanthine derivative is represented by the formula:

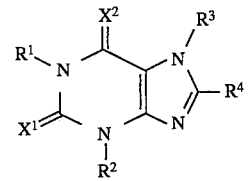

in which $R^1$, $R^2$ are $R^3$ are independently hydrogen, lower alkyl, lower alkenyl, or lower alkynyl; and $R^4$ represents cycloalkyl, —$(CH_2)_n$—$R^5$ (in which $R^5$ represents substituted or unsubstituted aryl or a substituted or unsubstituted heterocyclic group; and n is an integer of 0 to 4), or

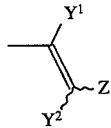

in which $Y^1$ and $Y^2$ represent independently hydrogen, halogen, or lower alkyl; and Z represents substituted or unsubstituted aryl,

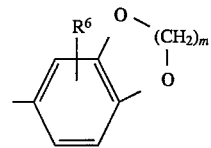

in which $R^6$ represents hydrogen, hydroxy, lower alkyl, lower alkoxy, halogen, nitro, or amino; and m represents an integer of 1 to 4, or a substituted or unsubstituted heterocyclic group; and $X^1$ and $X^2$ represent independently O or S.

11 Claims, No Drawings

THERAPEUTIC AGENT FOR PARKINSON'S DISEASE

CROSS REFERENCE TO RELATED APPLICATION

This application is a continuation-in-part of application Ser. No. 08/042,535, filed Apr. 5, 1993, now abandoned.

BACKGROUND OF THE INVENTION

The present invention relates to a therapeutic agent for Parkinson's disease containing a xanthine derivative or a salt thereof as an active ingredient.

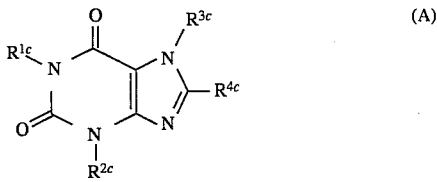
(A)

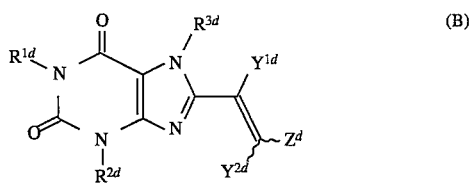
(B)

It is known that adenosine antagonistic action is found in compounds represented by Formula (A) in which $R^{1c}$ and $R^{2c}$ represent propyl, $R^{3c}$ represents hydrogen, and $R^{4c}$ represents substituted or unsubstituted phenyl, aromatic heterocyclic group, cycloalkyl, styryl, or phenylethyl [J. Med. Chem., 34, 1431 (1991)]. Further, Japanese Published Unexamined Patent Application No. 26516/72 discloses, as brain stimulants, compounds represented by Formula (B) in which $R^{1d}$ and $R^{2d}$ independently represent methyl or ethyl, $R^{3d}$ represents methyl, $Y^{1d}$ and $Y^{2d}$ represent hydrogen, and $Z^d$ represents phenyl or 3,4,5-trimethoxyphenyl. WO92/06976 discloses, as adenosine $A_2$ receptor antagonists, compounds represented by Formula (B) in which $R^{1d}$ and $R^{2d}$ independently represent hydrogen, propyl, butyl, or allyl, $R^{3d}$ represents hydrogen or lower alkyl, $Y^{1d}$ and $Y^{2d}$ independently represent hydrogen or methyl, and $Z^d$ represents phenyl, pyridyl, imidazolyl, furyl, or thienyl unsubstituted or substituted by 1 to 3 substituents such as lower alkyl, hydroxy, lower alkoxy, halogen, amino, and nitro. Furthermore, other compounds represented by Formula (B) are known. One is 8-styryl caffeine which is a compound of Formula (B) in which $R^{1d}$, $R^{2d}$, and $R^{3d}$ represent methyl, $Y^{1d}$ and $Y^{2d}$ represent hydrogen, and $Z^d$ represents phenyl [Chem. Ber. 119, 1525 (1986)]. Another is a compound of Formula (B) in which $R^{1d}$, $R^{2d}$, and $R^{3d}$ represent methyl, $Y^{1d}$ and $Y^{2d}$ represent hydrogen, and $Z^d$ represents pyridyl, quinolyl, or methoxy-substituted or unsubstituted benzothiazolyl [Chem. Abst. 60, 1741h (1964)]. However, there is no description with regard to the pharmacologic action of any of these compounds.

SUMMARY OF THE INVENTION

An object of the present invention is to provide an excellent therapeutic agent for Parkinson's disease having a xanthine skeleton and having a potent and selective adenosine $A_2$ receptor antagonistic activity.

The present invention relates to a therapeutic agent for Parkinson's disease containing as an active ingredient a xanthine derivative or a pharmaceutically acceptable salt of the xanthine derivative, the xanthine derivative being represented by the following Formula (I):

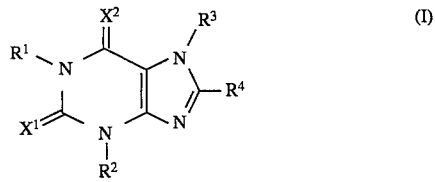
(I)

in which $R^1$, $R^2$, and $R^3$ represent independently hydrogen, lower alkyl, lower alkenyl, or lower alkynyl; $R^4$ represents cycloalkyl, —$(CH_2)_n$—$R^5$ (in which $R^5$ represents substituted or unsubstituted aryl or a substituted or unsubstituted heterocyclic group; and n is an integer of 0 to 4 ), or

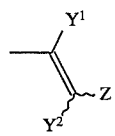

(in which $Y^1$ and $Y^2$ represent independently hydrogen, halogen, or lower alkyl; and Z represents substituted or unsubstituted aryl,

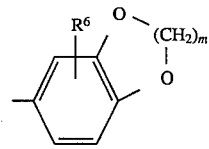

(in which $R^6$ represents hydrogen, hydroxy, lower alkyl, lower alkoxy, halogen, nitro, or amino; and m represents an integer of 1 to 3), or a substituted or unsubstituted heterocyclic group);
and $X^1$ and $X^2$ represent independently O or S.

The present invention also provides a xanthine derivative represented by the following Formula (I-A):

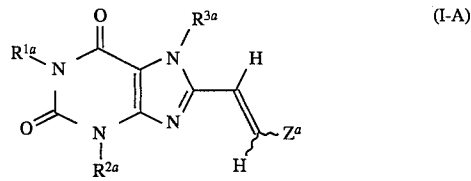
(I-A)

in which $R^{1a}$ and $R^{2a}$ represent independently methyl or ethyl;
$R^{3a}$ represents hydrogen or lower alkyl;
and $Z^a$ represents

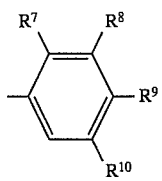

(in which at least one of $R^7$, $R^8$, and $R^9$ represents lower alkyl or lower alkoxy and the others represent hydrogen; $R^{10}$ represents hydrogen or lower alkyl) or

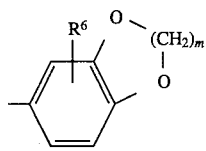

(in which $R^6$ and m have the same meanings as defined above), or a pharmaceutically acceptable salt thereof.

The present invention also provides a xanthine derivative represented by the following Formula (I-B):

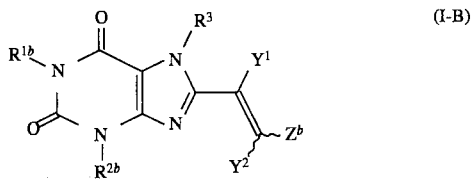

in which $R^{1b}$ and $R^{2b}$ represent independently hydrogen, propyl, butyl, lower alkenyl, or lower alkynyl;
$Z^b$ represents substituted or unsubstituted naphthyl, or

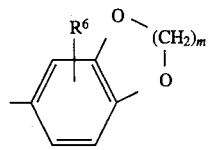

(in which $R^6$ and m have the same meanings as defined above); and $R^3$, $Y^1$ and $Y^2$ have the same meanings as defined above, or a pharmaceutically acceptable salt thereof.

The present invention further provides a method of treating Parkinson's disease comprising administration of an effective amount of a xanthine derivative.

DETAILED DESCRIPTION OF THE INVENTION

In the definitions of the groups in Formula (I), Formula (I-A), and Formula (I-B), the lower alkyl and the lower alkyl moiety of the lower alkoxy mean a straight-chain or branched alkyl group having 1 to 6 carbon atoms, such as methyl, ethyl, propyl, isopropyl, butyl, isobutyl, sec-butyl, tert-butyl, pentyl, neopentyl, and hexyl. The lower alkenyl means a straight-chain or branched alkenyl group having 2 to 6 carbon atoms, such as vinyl, allyl, methacryl, crotyl, 3-butenyl, 2-pentenyl, 4-pentenyl, 2-hexenyl, 5-hexenyl. The lower alkynyl means a straight-chain or branched alkenyl group having 2 to 6 carbon atoms, such as ethynyl, propargyl, 2-butynyl, 3-butynyl, 2-pentynyl, 4-pentynyl, 2-hexynyl, 5-hexynyl, 4-methyl-2-pentynyl. The aryl means phenyl or naphthyl. The cycloalkyl means a cycloalkyl group having 3 to 8 carbon atoms, such as cyclopropyl, cyclobutyl, cyclopentyl, cyclohexyl, cycloheptyl, and cyclooctyl. Examples of the heterocyclic group are furyl, thienyl, pyrrolyl, pyranyl, thiopyranyl, pyridyl, thiazolyl, imidazolyl, pyrimidyl, triazinyl, indolyl, quinolyl, purinyl, and benzothiazolyl. The halogen includes fluorine, chlorine, bromine, and iodine.

The substituted aryl and the substituted heterocyclic ring each has 1 to 4 independently-selected substituents. Examples of the substituents are lower alkyl, hydroxy, substituted or unsubstituted lower alkoxy, halogen, nitro, amino, lower alkylamino, di(lower alkyl) amino, trifluoromethyl, trifluoromethoxy, benzyloxy, phenyl, and phenoxy.

The lower alkyl and the alkyl moiety of the lower alkoxy, lower alkylamino, and di(lower alkyl)amino have the same meaning as the lower alkyl defined above. The halogen has the same meaning as the halogen defined above. Examples of the substituent of the substituted lower alkoxy are hydroxy, lower alkoxy, halogen, amino, azide, carboxy, and lower alkoxycarbonyl. The lower alkyl moiety of the lower alkoxy and lower alkoxycarbonyl has the same meaning as the lower alkyl defined above, and the halogen has the same meaning as the halogen defined above.

The above-mentioned pharmaceutically acceptable salts of Compounds (I), Compounds (I-A), and Compounds (I-B) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The processes for producing Compounds (I) are described below. Compounds (I) can also be produced according to the methods described in, for example, U.S. Pat. No. 3,641,010; J. Med. Chem., 34, 1431 (1991); Chem. Ber., 119, 1525 (1986); and Chem. Abst., 60, 1741h (1964).

PROCESS 1

Compound (I-a) [Compound (I) in which $R^3$ is hydrogen] can be prepared by the following reaction steps:

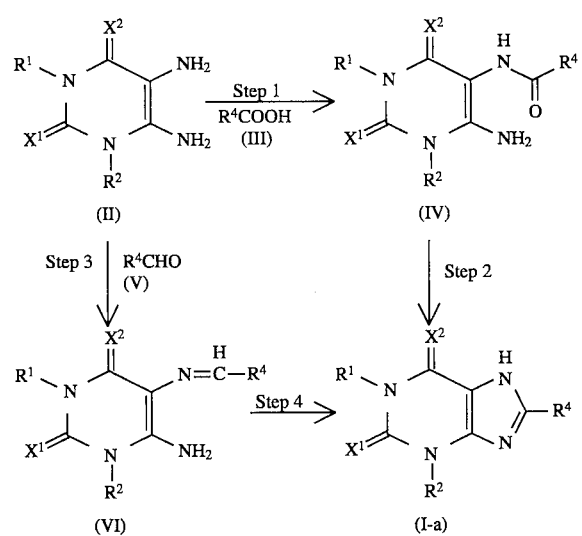

(In the formulae $R^1$, $R^2$, $R^4$, $X^1$, and $X^2$ have the same meanings as defined above.)

Step 1

A uracil derivative (II) obtained by a known method [for example, Japanese Published Unexamined Patent Application No. 42383/84; J. Med. Chem., 32, 1873 (1989)] is allowed to react with either a carboxylic acid (III) or a reactive derivative thereof to give Compound (IV). Examples of the reactive derivative of the carboxylic acid (III) are acid halides such as acid chloride and acid bromide, active esters such as p-nitrophenyl ester and N-oxysuccinimide, commercially available acid anhydrides, acid anhydrides produced by using carbodiimides such as 3-(3-dimethylaminopropyl)-1-ethylcarbodiimide, diisopropyl carbodiimide, and dicyclohexyl carbodiimide, and mixed acid anhydrides with monoethyl carbonate or monoisobutyl carbonate. If the carboxylic acid (III) is used, the reaction is completed in 10 minutes to 5 hours at 50 to 200° C. without using a solvent.

If a reactive derivative of the carboxylic acid (III) is used, the reaction can be carried out according to a conventional method employed in peptide chemistry. That is, Compound (II) and a derivative of the carboxylic acid (III) are allowed to react in a solvent, preferably in the presence of an additive or a base, to give Compound (IV). Examples of the solvent are halogenated hydrocarbons such as methylene chloride, chloroform, and ethylene dichloride, ethers such as dioxane and tetrahydrofuran, dimethylformamide, dimethylsulfoxide, and water if necessary. An example of the additive is 1-hydroxybenzotriazole. Examples of the base are pyridine, triethylamine, 4-dimethylaminopyridine, and N-methylmorpholine. The reaction is completed in 0.5 to 24 hours at −80° to 50° C. The reactive derivative may be formed in the reaction system and then used without being isolated.

Step 2

Compound (I-a) can be obtained by reaction of Compound (IV) carried out in any of the following manners: in the presence of a base (Method A); by treatment with a dehydrating agent (Method B); or by heating (Method C). In Method A, the reaction is carried out in a solvent in the presence of a base such as an alkali metal hydroxide (e.g. sodium hydroxide and potassium hydroxide). As the solvent, water, lower alcohols such as methanol and ethanol, ethers such as dioxane and tetrahydrofuran, dimethylformamide, dimethylsulfoxide, and the like may be used alone or in combination. The reaction is completed in 10 minutes to 6 hours at 0° to 180° C.

In Method B, the reaction is carried out in an inert solvent or in the absence of a solvent using a dehydrating agent such as a thionyl halide (e.g. thionyl chloride) and a phosphorus oxyhalide (e.g. phosphorus oxychloride). Examples of the inert solvent are halogenated hydrocarbons such as methylene chloride, chloroform and ethylene dichloride, dimethylformamide, and dimethylsulfoxide. The reaction is completed in 0.5 to 12 hours at 0° to 180° C.

In Method C, the reaction is carried out in a polar solvent such as dimethylformamide, dimethylsulfoxide, and Dowtherm A (Dow Chemicals). The reaction is completed in 10 minutes to 5 hours at 50° to 200° C.

Step 3

Compound (II) is allowed to react with an aldehyde (V) to give a Schiff's base (VI). As a reaction solvent, mixtures of acetic acid and a lower alcohol such as methanol and ethanol may be used. The reaction is completed in 0.5 to 12 hours at −20° to 100° C.

Step 4

Compound (VI) is oxidatively cyclized in an inert solvent in the presence of an oxidizing agent to form Compound (I-a). Examples of the oxidizing agent are oxygen, ferric chloride, cerium (IV) ammonium nitrate, and diethylazodicarboxylate. Examples of the inert solvent are lower alcohols such as methanol and ethanol, halogenated hydrocarbons such as methylene chloride and chloroform, and aromatic hydrocarbons such as toluene, xylene, and nitrobenzene. The reaction is completed in 10 minutes to 12 hours at 0° to 180° C.

PROCESS 2

Compound (I-b) [Compound (I) in which $R^3$ is a group other than hydrogen] can be prepared by the following reaction step.

Compound (I-b) is obtained from Compound (I-a) prepared by Process 1.

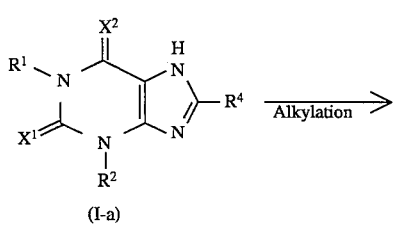

(In the formulae, $R^{3e}$ represents a group other than hydrogen in the definition of $R^3$; and $R^1$, $R^2$, $R^4$, $X^1$, and $X^2$ have the same meanings as defined above.)

Compound (I-b) can be obtained by reaction of Compound (I-a) with an alkylating agent, in the presence of a base if necessary. Examples of the alkylating agent are alkyl halides such as methyl iodide, ethyl iodide, and allyl bromide, dialkyl sulfates such as dimethyl sulfate, sulfonic esters such as allyl p-tolenesulfonate and methyl trifluoromethanesulfonate, and diazoalkanes such as diazomethane. Examples of the base are alkali metal carbonates such as sodium carbonate and potassium carbonate, alkali metal hydrides such as sodium hydride, and alkali metal alkoxides such as sodium methoxide and sodium ethoxide. As a reaction solvent, aromatic hydrocarbons such as toluene and xylene, ketones such as acetone and methyl ethyl ketone, dimethylformamide, dimethylsulfoxide, or the like may be used. The reaction is completed in 0.5 to 24 hours at 0° to 180° C.

PROCESS 3

Compound (I-d) [Compound (I) in which Z is phenyl having hydroxy as substituent(s)] can be alternatively prepared by the following reaction step.

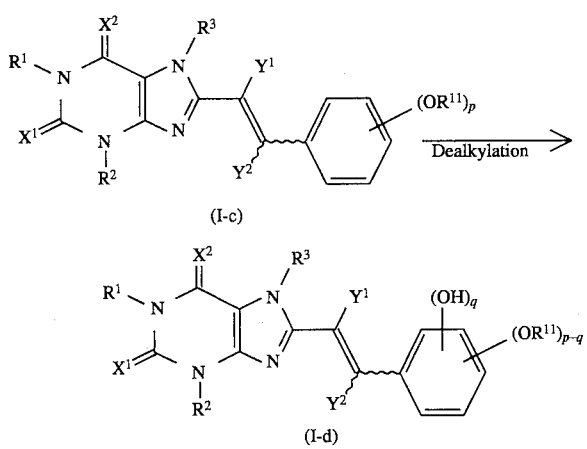

(I-c)

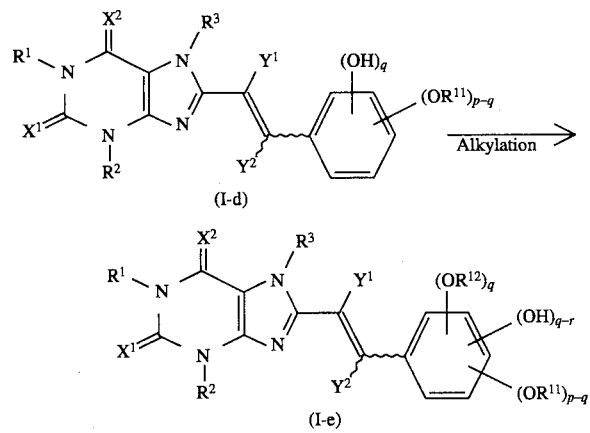

(I-d)

(In the formulae, $R^{11}$ represents substituted or unsubstituted lower alkyl; p and q are integers of 1 to 4 and $p \geq q$; and $R^1$, $R^2$, $R^3$, $X^1$, $X^2$, $Y^1$, and $Y^2$ have the same meanings as defined above.)

The substituted or unsubstituted lower alkyl in the definition of $R^{11}$ has the same meaning as defined above.

Compound (I-d) can be obtained by reaction of Compound (I-c) [Compound (I) in which Z is phenyl having lower alkoxy as substituent (s)] obtained by Process 1 or Process 2 with a dealkylating agent. Examples of the suitable dealkylating agent are boron tribromide and the complex thereof with dimethyl disulfide, boron trichloride, iodotrimethylsilane, sodium ethanethiolate, sodium benzenethiolate, and hydrobromic acid. A reaction solvent is selected from aromatic hydrocarbons such as toluene and xylene, halogenated hydrocarbons such as methylene chloride, chloroform, and ethylene dichloride, dimethylformamide, acetic acid, etc. depending upon the kind of the dealkylating agent used. The reaction is completed in 10 minutes to 120 hours at −30° to 140° C.

PROCESS 4

Compound (I-e) [Compound (I) in which Z is phenyl having lower alkoxy as substituent(s)] can be alternatively prepared by the following reaction step.

(I-d)

(I-e)

(In the formulae, $R^{12}$ represents substituted or unsubstituted lower alkyl; r is an integer of 1 to 4 and $q \geq r$; and $R^1$, $R^2$, $R^3$, $R^{11}$, $X^1$, $X^2$, $Y^1$, $Y^2$, p, and q have the same meanings as defined above.)

The substituted or unsubstituted lower alkyl in the definition of $R^{12}$ has the same meaning as defined above.

Compound (I-e) can be obtained from Compound (I-d) according to the method of Process 2.

PROCESS 5

Compound (I-h) [Compound (I) in which Z is phenyl having amino-substituted lower alkoxy as the substituent] can be alternatively prepared by the following reaction step.

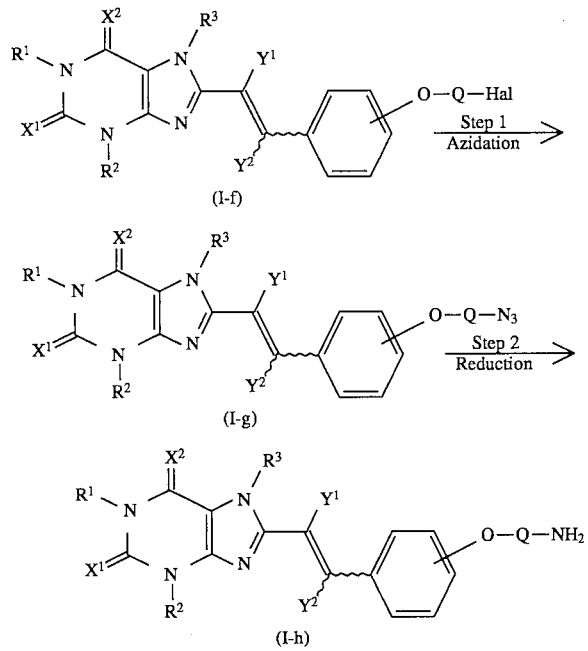

(I-f)

(I-g)

(I-h)

(In the formulae, Q represents lower alkylene; Hal represents chlorine, bromine, or iodine; and $R^1$, $R^2$, $R^3$, $X^1$, $X^2$, $Y^1$, and $Y^2$ have the same meanings as defined above.)

The lower alkylene in the definition of Q means a straight-chain or branched alkylene group having 1 to 6 carbon atoms, such as methylene, ethylene, propylene, 1-methylethylene, butylene, 1-methylpropylene, 2-methylpropylene, pentylene, and hexylene.

Step 1

Compound (I-g) can be obtained by reaction of Compound (I-f) [Compound (I) in which Z is phenyl having chlorine, bromine, or iodine-substituted lower alkoxy as the substituent] obtained by Process 4 with 5 to 10 equivalents of sodium azide. As a reaction solvent, an inert solvent such as dimethylformamide may be used. The reaction is completed in 1 to 10 hours at 50° to 80° C.

Step 2

Compound (I-h) can be obtained by treatment of Compound (I-g) in an inert solvent such as tetrahydrofuran and dioxane in the presence of 2 to 5 equivalents of a reducing agent such as triphenylphosphine, followed by addition of an excess of water and further treatment for 1 to 10 hours at 50° C. to the boiling point of the solvent used.

PROCESS 6

Compound (I-j) [Compound (I) in which Z is phenyl having carboxy-substituted lower alkoxy as the substituent] can be alternatively prepared by the following reaction step.

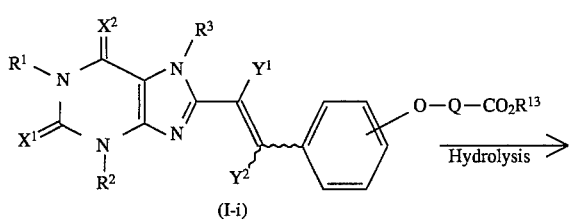

(I-i)

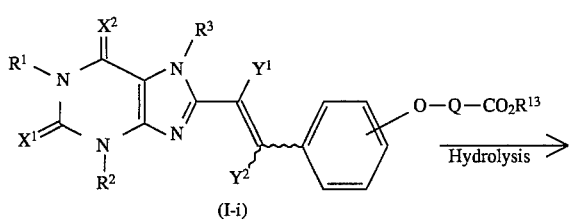

(I-j)

(In the formulae, $R^{13}$ represents lower alkyl; and $R^1$, $R^2$, $R^3$, Q, $X^1$, $X^2$, $Y^1$, and $Y^2$ have the same meanings as defined above.)

The lower alkyl in the definition of $R^{13}$ has the same meaning as defined above.

Compound (I-j) can be obtained by hydrolysis of Compound (I-i) [Compound (I) in which Z is phenyl having lower alkoxycarbonyl-substituted lower alkoxy as the substituent] obtained by Process 4 in the presence of an alkali metal hydroxide such as sodium hydroxide and lithium hydroxide. As a reaction solvent, a mixture of water and an ether such as dioxane and tetrahydrofuran, or a mixture of water and an alcohol such as methanol and ethanol may be used. The reaction is completed in 10 minutes to 12 hours at room temperature to the boiling point of the solvent used.

PROCESS 7

Compound (I-m) [Compound (I) in which Z is phenyl having hydroxy as the substituent(s)] can be alternatively prepared by the following reaction step.

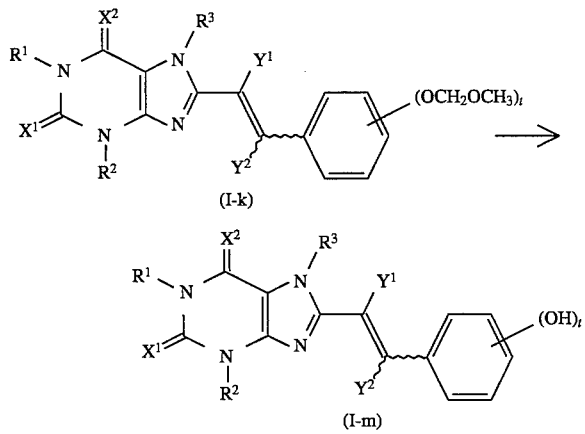

(I-k)

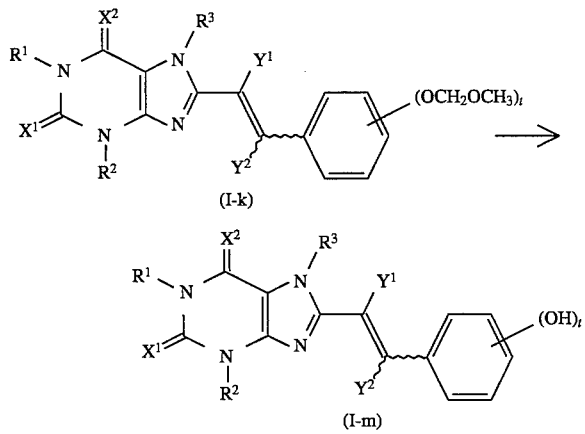

(I-m)

(In the formulae, t is an integer of 1 to 4; and $R^1$, $R^2$, $R^3$, $X^1$, $X^2$, $Y^1$, and $Y^2$ have the same meanings as defined above.)

Compound (I-m) can be obtained by treatment of Compound (I-k) [Compound (I) in which Z is phenyl having methoxymethoxy as the substituent (s)] obtained by Process 1, Process 2, or Process 4 in the presence of hydrogen chloride gas, an aqueous solution of hydrochloric acid, or the like. As a reaction solvent, ethers such as dioxane and tetrahydrofuran, alcohols such as methanol and ethanol, or the like may be used. The reaction is completed in 1 to 20 hours at room temperature to the boiling point of the solvent used.

PROCESS 8

Compound (I-o) [Compound (I) in which $X^2$ is S] can be alternatively prepared by the following reaction step.

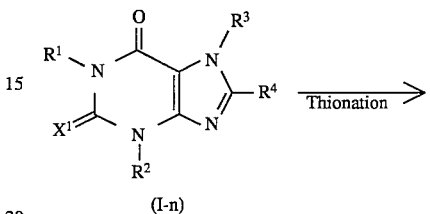

(I-n)

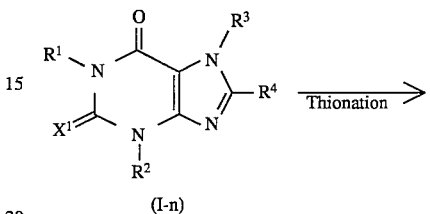

(I-o)

(In the formulae $R^1$, $R^2$, $R^3$, $R^4$, and $X^1$ have the same meanings as defined above.)

Compound (I-o) can be obtained by reaction of Compound (I-n) [Compound (I) in which $X^2$ is O] obtained by Process 1 to Process 7 with a thionating agent. Examples of the thionating agent are phosphorus pentachloride and Leawsson's reagent. As a reaction solvent, pyridine, dimethylformamide, dioxane, tetrahydrofuran, or the like, preferably pyridine, may be used. The reaction is completed in 10 minutes to 36 hours at 50° to 180° C.

The desired compounds in the processes described above can be isolated and purified by purification methods conventionally used in organic synthetic chemistry, for example, filtration, extraction, washing, drying, concentration, recrystallization, and various kinds of chromatography.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or a base to form a salt.

Some of Compounds (I) can exist in the form of geometrical isomers such as an (E)-isomer and a (Z)-isomer, and the present invention covers all possible isomers including the above-mentioned ones and mixtures thereof. In the case where separation between an (E)-isomer and a (Z)-isomer is desired, they can be isolated and purified by fractionation methods, for example, fractional crystallization, fractional precipitation, and fractional dissolution.

Compounds (I) and pharmaceutically acceptable salts thereof may be in the form of adducts with water or various solvents, which can also be used as the therapeutic agent of the present invention.

Examples of Compounds (I) are shown in Table 1.

TABLE 1

[Structure: imidazole-fused diketopiperazine-like core with R¹-N, R²-N, R³-N substituents and a vinyl-Z group]

| Compound | −R¹ | −R² | −Z | −R³ |
|---|---|---|---|---|
| 1 | −(CH₂)₂CH₃ | −(CH₂)₂CH₃ | 3,4-dimethoxyphenyl (OCH₃, OCH₃) | −CH₃ |
| 2 | −CH₃ | −CH₃ | 3,4,5-trimethoxyphenyl (OCH₃, OCH₃, OCH₃) | " |
| 3 | −(CH₂)₂CH₃ | −(CH₂)₂CH₃ | phenyl | " |
| 4 | −CH₂CH₃ | −CH₂CH₃ | 3,4,5-trimethoxyphenyl (OCH₃, OCH₃, OCH₃) | " |
| 5 | −(CH₂)₂CH₃ | −(CH₂)₂CH₃ | " | " |
| 6 | " | " | 4-methoxyphenyl (OCH₃) | " |
| 7 | −CH₂−CH=CH₂ | −CH₂−CH=CH₂ | 3,4,5-trimethoxyphenyl (OCH₃, OCH₃, OCH₃) | " |
| 8 | −(CH₂)₃CH₃ | −(CH₂)₃CH₃ | " | " |
| 9 | −(CH₂)₂CH₃ | −(CH₂)₂CH₃ | " | −H |
| 10 | −CH₃ | −CH₃ | " | " |
| 11 | −CH₂−CH=CH₂ | −CH₂−CH=CH₂ | " | " |
| 12 | −(CH₂)₂CH₃ | −(CH₂)₂CH₃ | 4-OCH₃, 2,3-di-CH₃ phenyl (H₃C, CH₃) | " |
| 13 | " | " | " | −CH₃ |
| 14 | " | " | 2,5-di-OCH₃, 3-CH₃ phenyl (OCH₃, H₃CO, CH₃) | −H |
| 15 | " | " | " | −CH₃ |

TABLE 1-continued
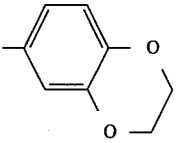
| Compound | —R¹ | —R² | —Z | —R³ |
|---|---|---|---|---|
| 16 | —(CH₂)₂CH₃ | —(CH₂)₂CH₃ | 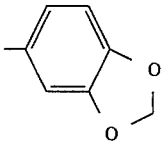 | —H |
| 17 | " | " | " | —CH₃ |
| 18 | " | " | 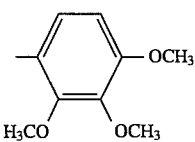 | —H |
| 19 | " | " | " | —CH₃ |
| 20 | " | " | 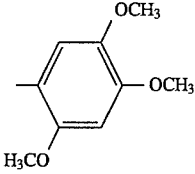 | —H |
| 21 | " | " | " | —CH₃ |
| 22 | " | " | 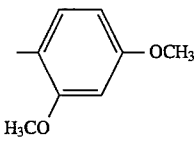 | —H |
| 23 | " | " | " | —CH₃ |
| 24 | " | " | 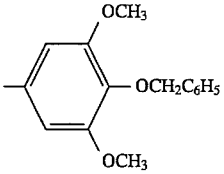 | —H |
| 25 | " | " | " | —CH₃ |
| 26 | " | " | 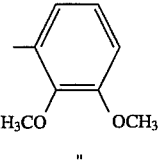 | —H |
| 27 | " | " | " | —CH₃ |
| 28 | " | " |  | —H |
| 29 | " | " | " | —CH₃ |

TABLE 1-continued
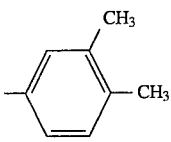
| Compound | —R¹ | —R² | —Z | —R³ |
|---|---|---|---|---|
| 30 | " | " | 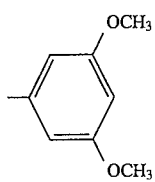 2,5-(CH₃)₂-phenyl | —H |
| 31 | " | " | " | —CH₃ |
| 32 | —(CH₂)₂CH₃ | —(CH₂)₂CH₃ | 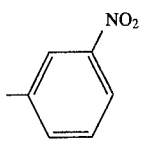 3,5-(OCH₃)₂-phenyl | —H |
| 33 | " | " | " | —CH₃ |
| 34 | " | " | 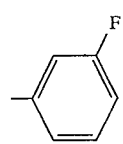 3-NO₂-phenyl | —H |
| 35 | " | " | " | —CH₃ |
| 36 | " | " | 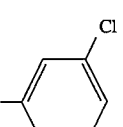 3-F-phenyl | —H |
| 37 | " | " | " | —CH₃ |
| 38 | " | " | 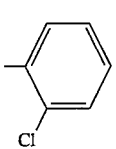 3-Cl-phenyl | —H |
| 39 | " | " | " | —CH₃ |
| 40 | " | " | 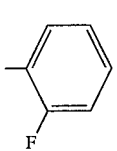 2-Cl-phenyl | —H |
| 41 | " | " | " | —CH₃ |
| 42 | " | " | 2-F-phenyl | —H |
| 43 | " | " | " | —CH₃ |

TABLE 1-continued

Structure:

R¹—N, R², R³ substituents on a pyrimidine-imidazole core with vinyl-Z group

| Compound | —R¹ | —R² | —Z | —R³ |
|---|---|---|---|---|
| 44 | " | " | 2,5-dimethyl-4-methoxyphenyl (CH₃, OCH₃, H₃C) | —H |
| 45 | " | " | " | —CH₃ |
| 46* | " | " | R⁴ = trans-CH=CH–(3,4-dimethoxyphenyl) (H₃CO, OCH₃) | " |

*: An about 6:4 mixture with Compound 1

| Compound | —R¹ | —R² | —Z | —R³ |
|---|---|---|---|---|
| 47 | —(CH₂)₂CH₃ | —(CH₂)₂CH₃ | 4-OCH₂CH₃-phenyl | —H |
| 48 | " | " | " | —CH₃ |
| 49 | " | " | 4-O(CH₂)₂CH₃-phenyl | —H |
| 50 | " | " | " | —CH₃ |
| 51 | " | " | 4-O(CH₂)₃CH₃-phenyl | —H |
| 52 | " | " | " | —CH₃ |
| 53 | " | " | 3,4-dihydroxyphenyl (OH, OH) | " |
| 54 | " | " | 3,4-bis(ethoxy)phenyl (OCH₂CH₂, OCH₂CH₃) | " |
| 55 | " | " | 3-bromo-4-methoxyphenyl (OCH₃, Br) | —H |

TABLE 1-continued

| Compound | —R¹ | —R² | —Z | —R³ |
|---|---|---|---|---|
| 56 | " | " | " | —CH₃ |
| 57 | " | " | 5-bromo-2,3-dimethoxyphenyl (Br para to bond, OCH₃ at 2,3-positions shown) | —H |
| 58 | " | " | " | —CH₃ |
| 59 | " | " | 3-bromo-4,5-dimethoxyphenyl | —H |
| 60 | " | " | " | —CH₃ |
| 61 | " | " | 4-methoxy-1-naphthyl | —H |
| 62 | " | " | " | —CH₃ |
| 63 | " | " | 3-hydroxy-4-methoxyphenyl | " |
| 64 | —CH₂CH₃ | —CH₂CH₃ | 3,4-dimethoxyphenyl | —H |
| 65 | " | " | " | —CH₃ |
| 66 | " | " | 2,3-dimethoxyphenyl | —H |
| 67 | " | " | " | —CH₃ |
| 68 | " | " | 2,4-dimethoxyphenyl (H₃CO and OCH₃ on ring) | —H |

TABLE 1-continued
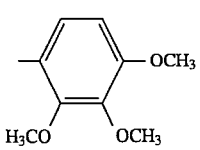
| Compound | —R¹ | —R² | —Z | —R³ |
|---|---|---|---|---|
| 69 | " | " | " | —CH₃ |
| 70 | " | " | 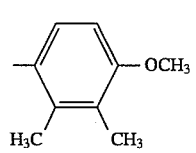 | —H |
| 71 | " | " | " | —CH₃ |
| 72 | " | " | 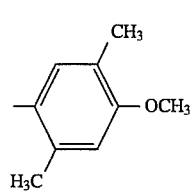 | —H |
| 73 | " | " | " | —CH₃ |
| 74 | " | " | 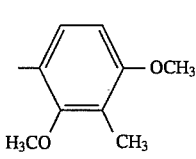 | —H |
| 75 | " | " | " | —CH₃ |
| 76 | " | " | 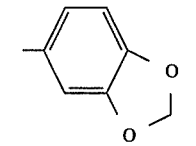 | —H |
| 77 | " | " | " | —CH₃ |
| 78 | —CH₂CH₃ | —CH₂CH₃ | 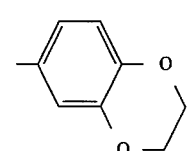 | —H |
| 79 | " | " | " | —CH₃ |
| 80 | " | " | 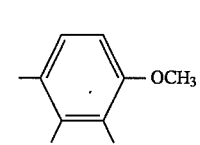 | —H |
| 81 | " | " | " | —CH₃ |
| 82 | —CH₃ | —CH₃ | 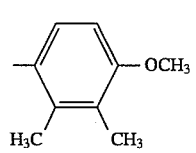 | —H |
| 83 | " | " | " | —CH₃ |

TABLE 1-continued
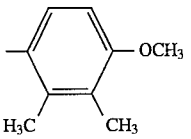
| Compound | —R¹ | —R² | —Z | —R³ |
|---|---|---|---|---|
| 84 | " | " | 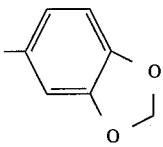 | —H |
| 85 | " | " | " | —CH₃ |
| 86 | " | " | 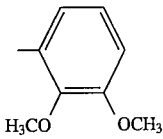 | —H |
| 87 | " | " | " | —CH₃ |
| 88 | " | " | 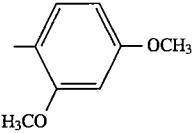 | —H |
| 89 | " | " | " | —CH₃ |
| 90 | " | " | 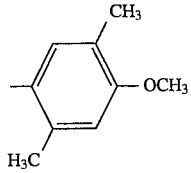 | —H |
| 91 | " | " | " | —CH₃ |
| 92 | " | " | 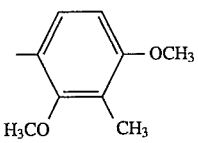 | —H |
| 93 | " | " | " | —CH₃ |
| 94 | " | " | 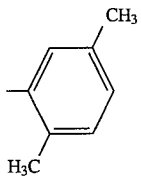 | —H |
| 95 | " | " | " | —CH₃ |
| 96 | —CH₂CH₃ | —CH₂CH₃ |  | —H |
| 97 | " | " | " | —CH₃ |

TABLE 1-continued

Structure: imidazo-pyrimidinedione core with R¹, R², R³ substituents and vinyl-Z group

| Compound | −R¹ | −R² | −Z | −R³ |
|---|---|---|---|---|
| 98 | " | " | 4-(OCH₂CH₃)-C₆H₄− | −H |
| 99 | " | " | " | −CH₃ |
| 100 | " | " | 4-(O(CH₂)₂CH₃)-C₆H₄− | −H |
| 101 | " | " | " | −CH₃ |
| 102 | " | " | 3-(OCH₃)-C₆H₄− | −H |
| 103 | " | " | " | −CH₃ |
| 104 | " | " | 4-(O(CH₂)₃CH₃)-C₆H₄− | −H |
| 105 | " | " | " | −CH₃ |
| 106 | " | " | 4-CH₃-C₆H₄− | −H |
| 107 | " | " | " | −CH₃ |
| 108 | " | " | 2-(OCH₃)-C₆H₄− | −H |
| 109 | " | " | " | −CH₃ |
| 110 | " | " | 3-CH₃-4-OCH₃-C₆H₃− | −H |
| 111 | " | " | " | −CH₃ |
| 112 | " | " | 4-Cl-2,3-(OCH₃)₂-C₆H₂− | −H |
| 113 | " | " | " | −CH₃ |
| 114 | −CH₃ | −CH₃ | " | −H |
| 115 | " | " | " | −CH₃ |

TABLE 1-continued
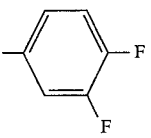
| Compound | —R¹ | —R² | —Z | —R³ |
|---|---|---|---|---|
| 116 | —CH₂CH₃ | —CH₂CH₃ | 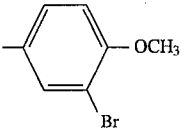 | —H |
| 117 | " | " | " | —CH₃ |
| 118 | —CH₂CH₃ | —CH₂CH₃ | 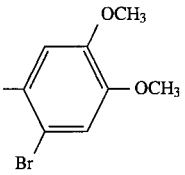 | —H |
| 119 | " | " | " | —CH₃ |
| 120 | —CH₃ | —CH₃ | " | —H |
| 121 | " | " | " | —CH₃ |
| 122 | —CH₂CH₃ | —CH₂CH₃ | 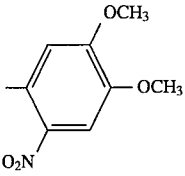 | —H |
| 123 | " | " | " | —CH₃ |
| 124 | " | " | 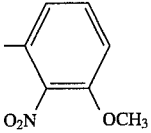 | —H |
| 125 | " | " | " | —CH₃ |
| 126 | " | " | 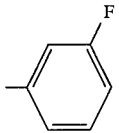 | —H |
| 127 | " | " | " | —CH₃ |
| 128 | " | " |  | —H |
| 129 | " | " | " | —CH₃ |

TABLE 1-continued

| Compound | —R¹ | —R² | —Z | —R³ |
|---|---|---|---|---|
| 130 | " | " | 3,5-dimethoxyphenyl (OCH₃ at two positions) | —H |
| 131 | " | " | " | —CH₃ |
| 132 | " | " | 3-chlorophenyl | —H |
| 133 | " | " | " | —CH₃ |
| 134 | —CH₂CH₃ | —CH₂CH₃ | R⁴=CH₃, phenyl (with H) | —H |
| 135 | " | " | " | —CH₃ |
| 136 | " | " | 4-CF₃-phenyl | —H |
| 137 | " | " | " | —CH₃ |
| 138 | " | " | R⁴=F, phenyl (with H) | —H |
| 139 | " | " | " | —CH₃ |
| 140 | " | " | 4-Br-phenyl | —H |
| 141 | " | " | " | —CH₃ |
| 142 | " | " | 3-OCF₃-phenyl | —H |
| 143 | " | " | " | —CH₃ |
| 144 | " | " | 4-OCH₂OCH₃-phenyl | —H |
| 145 | " | " | " | —CH₃ |

TABLE 1-continued

| Compound | —R¹ | —R² | —Z | —R³ |
|---|---|---|---|---|
| 146 | " | " | 4-F-C₆H₄ | —H |
| 147 | " | " | " | —CH₃ |
| 148 | " | " | 3,5-(CF₃)₂-C₆H₃ | —H |
| 149 | " | " | " | —CH₃ |
| 150 | " | " | 3,5-F₂-C₆H₃ | —H |
| 151 | " | " | " | —CH₃ |
| 152 | —CH₂CH₃ | —CH₂CH₃ | 3-NO₂-C₆H₄ | —H |
| 153 | " | " | " | —CH₃ |
| 154 | " | " | 3-Br-C₆H₄ | —H |
| 155 | " | " | " | —CH₃ |
| 156 | " | " | 3-CF₃-C₆H₄ | —H |
| 157 | " | " | " | —CH₃ |
| 158 | " | " | 5-Br-3,4-(OCH₂O)-C₆H₂ | —H |
| 159 | " | " | " | —CH₃ |

TABLE 1-continued
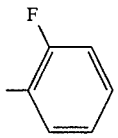
| Compound | −R¹ | −R² | −Z | −R³ |
|---|---|---|---|---|
| 160 | " | " | 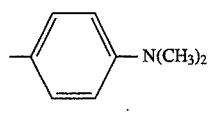 (2-F-phenyl) | −H |
| 161 | " | " | " | −CH₃ |
| 162 | " | " | 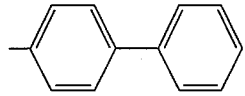 (4-N(CH₃)₂-phenyl) | −H |
| 163 | " | " | 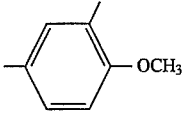 (biphenyl) | " |
| 164 | " | " | " | −CH₃ |
| 165 | " | " | 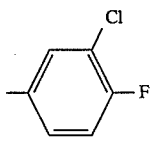 (3-F-4-OCH₃-phenyl) | −H |
| 166 | " | " | " | −CH₃ |
| 167 | " | " | 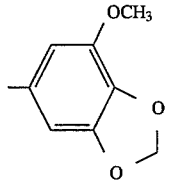 (3-Cl-4-F-phenyl) | −H |
| 168 | " | " | " | −CH₃ |
| 169 | −CH₂CH₃ | −CH₂CH₃ | 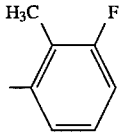 (methylenedioxy-OCH₃-phenyl) | −H |
| 170 | " | " | " | −CH₃ |
| 171 | " | " | 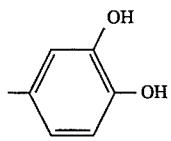 (2-CH₃-6-F-phenyl) | −H |
| 172 | " | " | " | −CH₃ |
| 173 | " | " | (3,4-diOH-phenyl) | " |

TABLE 1-continued

[Structure diagram: R¹-N, R², R³, Z on imidazole-pyrimidinedione core with vinyl-Z substituent]

| Compound | —R¹ | —R² | —Z | —R³ |
|---|---|---|---|---|
| 174 | " | " | phenyl with OH and OCH₃ | " |
| 175 | " | " | phenyl with OH | " |
| 176 | " | " | phenyl with OCH₂C₆H₅ | " |
| 177 | " | " | phenyl with O(CH₂)₄Br | " |
| 178 | " | " | phenyl with O(CH₂)₄N₃ | " |
| 179 | " | " | phenyl with O(CH₂)₄NH₂ | " |
| 180 | " | " | phenyl with OCH₂CO₂C₂H₅ | " |
| 181 | " | " | phenyl with OCH₂CO₂H | " |
| 182 | " | " | phenyl with O-phenyl | —H |
| 183 | " | " | " | —CH₃ |
| 184 | " | " | phenyl with OH | —H |
| 185 | " | " | phenyl with OH and two CH₃ (H₃C, CH₃) | —CH₃ |

TABLE 1-continued

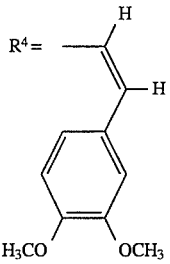

| Compound | —R¹ | —R² | —Z | —R³ |
|---|---|---|---|---|
| 186 | —(CH₂)₂CH₃ | —(CH₂)₂CH₃ | R⁴= (structure: trans-CH=CH-aryl with H₃CO and OCH₃ substituents) | —CH₃ |
| 187 | " | " | (3,4-dimethoxyphenyl) | —C₂H₅ |
| 188 | " | " | " | —CH₂C≡CH |
| 189 | " | " | (3,4-bis(OCH₂OCH₃)phenyl) | —CH₃ |
| 190 | —CH₂—CH=CH₂ | —CH₂—CH=CH₂ | (3,4-dimethoxyphenyl) | —H |
| 191 | " | " | " | —CH₃ |
| 192* | —(CH₂)₂CH₃ | —(CH₂)₂CH₃ | " | —H |
| 193* | " | " | " | —CH₃ |
| 194 | " | " | (4-OCH₂OCH₃, 3-OCH₃ phenyl) | —H |
| 195 | " | " | " | —CH₃ |
| 196 | " | " | (4-OH, 3-OCH₃ phenyl) | —H |
| 197 | " | " | " | —CH₃ |

*: 2位チオ体

The pharmacological activities of Compounds (I) are shown below by experimental examples.

EXPERIMENTAL EXAMPLE 1

Acute Toxicity Test

Test compounds were orally administered to groups of dd-strain male mice weighing 20±1 g, each group consisting of three mice. Seven days after the administration, minimum lethal dose (MLD) of each compound was determined by observing the mortality.

The results are shown in Table 2.

TABLE 2

| Compound | MLD (mg/kg) | Compound | MLD (mg/kg) |
|---|---|---|---|
| 1 | >300 | 94 | >100 |
| 2 | >300 | 95 | >100 |
| 3 | >300 | 96 | >300 |
| 4 | >300 | 97 | >300 |
| 5 | >300 | 98 | >100 |
| 6 | >300 | 99 | >300 |
| 7 | >300 | 100 | >100 |
| 8 | >300 | 101 | >300 |
| 9 | >300 | 102 | >100 |
| 10 | >300 | 103 | >300 |
| 11 | >300 | 104 | >100 |
| 12 | >300 | 105 | >100 |
| 13 | >300 | 106 | >100 |
| 14 | >100 | 107 | >100 |
| 15 | >300 | 108 | >100 |
| 16 | >300 | 109 | >100 |
| 17 | >300 | 110 | >100 |
| 18 | >300 | 111 | >100 |
| 19 | >300 | 112 | >100 |
| 20 | >300 | 113 | >300 |
| 21 | >300 | 114 | >100 |
| 22 | >300 | 115 | >300 |
| 23 | >300 | 116 | >300 |
| 24 | >100 | 117 | >300 |
| 25 | >300 | 118 | >100 |
| 26 | >100 | 119 | >100 |
| 27 | >100 | 120 | >100 |
| 28 | >100 | 121 | >300 |
| 29 | >300 | 122 | >100 |
| 30 | >100 | 123 | >100 |
| 31 | >300 | 124 | >100 |
| 32 | >100 | 125 | >300 |
| 33 | >300 | 126 | >300 |
| 34 | >100 | 127 | >100 |
| 35 | >100 | 128 | >100 |
| 36 | >100 | 129 | >300 |
| 37 | >300 | 130 | >100 |
| 38 | >100 | 131 | >300 |
| 39 | >300 | 132 | >100 |
| 40 | >100 | 133 | >300 |
| 41 | >100 | 134 | >100 |
| 42 | >100 | 135 | >300 |
| 43 | >100 | 136 | >100 |
| 44 | >300 | 137 | >300 |
| 45 | >300 | 138 | >100 |
| 46 | >300 | 139 | >100 |
| 47 | >100 | 140 | >100 |
| 48 | >300 | 141 | >100 |
| 49 | >100 | 142 | >100 |
| 50 | >300 | 143 | >100 |
| 51 | >100 | 144 | >100 |
| 52 | >300 | 145 | >100 |
| 53 | >100 | 146 | >100 |
| 54 | >100 | 147 | >100 |
| 55 | >100 | 148 | >100 |
| 56 | >100 | 149 | >100 |
| 57 | >300 | 150 | >100 |
| 58 | >300 | 151 | >100 |
| 59 | >300 | 152 | >100 |
| 60 | >100 | 153 | >100 |
| 61 | >100 | 154 | >100 |
| 62 | >300 | 155 | >100 |
| 63 | >100 | 156 | >100 |
| 64 | >300 | 157 | >100 |
| 65 | >300 | 158 | >100 |
| 66 | >300 | 159 | >100 |
| 67 | >300 | 160 | >100 |
| 68 | >100 | 161 | >100 |
| 69 | >300 | 162 | >100 |
| 70 | >300 | 163 | >100 |
| 71 | >300 | 164 | >100 |
| 72 | >300 | 165 | >100 |
| 73 | >300 | 166 | >100 |
| 74 | >300 | 167 | >100 |
| 75 | >300 | 168 | >100 |
| 76 | >300 | 169 | >100 |
| 77 | >300 | 170 | >100 |
| 78 | >300 | 171 | >100 |
| 79 | >300 | 172 | >100 |
| 80 | >100 | 173 | >100 |
| 81 | >300 | 174 | >100 |
| 82 | >300 | 175 | >100 |
| 83 | >300 | 176 | >100 |
| 84 | >100 | 177 | >100 |
| 85 | >100 | 178 | >100 |
| 86 | >300 | 179 | >100 |
| 87 | >300 | 180 | >100 |
| 88 | >100 | 181 | >100 |
| 89 | >300 | 182 | >100 |
| 90 | >100 | 183 | >100 |
| 91 | >300 | 184 | >100 |
| 92 | >100 | 185 | >100 |
| 93 | >100 | 186 | >300 |
|  |  | 187 | >300 |
|  |  | 188 | >300 |
|  |  | 189 | >100 |
|  |  | 190 | >100 |
|  |  | 191 | >100 |
|  |  | 192 | >100 |
|  |  | 193 | >300 |
|  |  | 194 | >100 |
|  |  | 195 | >100 |
|  |  | 196 | >100 |
|  |  | 197 | >100 |

As shown in Table 2, the MLD value of all the compounds are greater than 100 mg/kg or 300 mg/kg, indicating that the toxicity of the compounds is weak. Therefore, these compounds can be safely used in a wide range of doses.

EXPERIMENTAL EXAMPLE 2

Adenosine Receptor Antagonistic Activity

1) Adenosine $A_1$ Receptor Binding Test

The test was conducted according to the method of Bruns et al. [Proc. Natl. Acad. Sci., 77, 5547 (1980)] with slight modification.

Cerebrum of a guinea pig was suspended in ice-cooled 50 mM Tris hydroxymethyl aminomethane hydrochloride (Tris HCl) buffer (pH 7.7) by using Polytron homogenizer (manufactured by Kinematicas Co.). The suspension was centrifuged (50,000×g, 10 minutes), and the precipitate was suspended again in the same amount of 50 mM Tris HCl buffer. The suspension was centrifuged under the same conditions, and the final precipitate was suspended once again in 50 mM Tris HCl buffer to give a tissue concentration of 100 mg (wet weight)/ml. The tissue suspension was incubated at 37° C. for 30 minutes in the presence of 0.02 unit/mg tissue of adenosine deaminase (manufactured by Sigma Co.). The tissue suspension was then centrifuged (50,000×g, 10 minutes), and 50 mM Tris HCl buffer was added to the precipitate to adjust the concentration of tissue to 10 mg (wet weight)/ml.

To 1 ml of the tissue suspension thus prepared were added 50 μl of cyclohexyladenosine labeled with tritium ($^3$H-CHA: 27 Ci/mmol, manufactured by New England Nuclear Co.) (final concentration: 1.1 nM) and 50 μl of a test compound. The mixture solution was allowed to stand at 25° C. for 90 minutes and then rapidly filtered by suction through a glass fiber filter (GF/C manufactured by Whatman Co.). The filter was immediately washed three times with 5 ml each of ice-cooled 50 mM Tris HCl buffer, and transferred to a vial, and a scintillator (EX-H by Wako Pure Chemical Industries, Ltd.) was added thereto. The radioactivity on the filter was determined with a liquid scintillation counter (manufactured by Packard Instrument Co.).

The inhibition rate of the test compound against the binding of $A_1$ receptor ($^3$H-CHA binding) was calculated by the following equation:

$$\text{Inhibition Rate (\%)} = \left(1 - \frac{[B] - [N]}{[T] - [N]}\right) \times 100$$

[Notes]
1. "B" means the amount of radioactivity of $^3$H-CHA bound in the presence of a test compound at a concentration shown in Table 3.
2. "T" means the amount of radioactivity of $^3$H-CHA bound in the absence of a test compound.
3. "N" means the amount of radioactivity of $^3$H-CHA bound in the presence of 10 μM $N^6$-(L-2-phenylisopropyl)-adenosine (manufactured by Sigma Co.).

The results are shown in Table 3. The inhibition constant (Ki value) shown in the table was calculated by the Cheng-Prusoff's equation.

TABLE 3

| | $A_1$ Receptor | | |
|---|---|---|---|
| | Inhibition (%) | | $K_i$ |
| Compound | $10^{-5}$M | $10^{-4}$M | (nM) |
| 64 | 84 | 86 | |
| 65 | 67 | 62 | |
| 67 | 55 | 70 | |
| 70 | 34 | 49 | >10,000 |
| 71 | 89 | 94 | |
| 72 | 14 | 26 | >100,000 |
| 73 | 57 | 56 | |
| 76 | 59 | 71 | |
| 77 | 84 | 86 | |
| 78 | 25 | 35 | >100,000 |
| 79 | 53 | 72 | |
| 80 | 23 | 31 | >100,000 |
| 81 | 56 | 66 | |
| 82 | 10 | 31 | >100,000 |
| 83 | 11 | 1 | >100,000 |
| 84 | 36 | 40 | >100,000 |
| 85 | 1 | 1 | >100,000 |
| 86 | 32 | 38 | >100,000 |
| 87 | −4 | −25 | >100,000 |

2) Adenosine $A_2$ Receptor Binding Test

The test was conducted according to the method of Bruns et al. [Mol. Pharmacol., 29, 331 (1986)] with slight modification.

The similar procedure as in the above-described adenosine $A_1$ receptor binding test was repeated using rat corpus striatum to obtain the final precipitate of the tissue thereof. The precipitate was suspended in 50 mM Tris HCl buffer containing 10 mM magnesium chloride and 0.02 unit/mg tissue of adenosine deaminase (manufactured by Sigma Co.) to give a tissue concentration of 5 mg (wet weight)/ml.

To 1 ml of the tissue suspension thus prepared were added 50 μl of a mixture of N-ethylcarboxamidoadenosine labeled with tritium ($^3$H-NECA: 26 Ci/mmol, manufactured by Amersham Co.) (final concentration: 3.8 nM) and cyclopentyladenosine (CPA, manufactured by Sigma Co.) (final concentration: 50 nM), and 50 μl of a test compound. The mixture solution was allowed to stand at 25° C. for 120 minutes and then treated in the same manner as in the adenosine $A_1$ receptor binding test to determine the radioactivity bound to the $A_2$ receptors.

The inhibition rate of the test compound against the binding of $A_2$ receptor ($^3$H-NECA binding) was calculated by the following equation:

$$\text{Inhibition Rate (\%)} = \left(1 - \frac{[B] - [N]}{[T] - [N]}\right) \times 100$$

[Notes]
1. "B" means the amount of radioactivity of $^3$H-NECA bound in the presence of a test compound at a concentration shown in Table 4.
2. "T" means the amount of radioactivity of $^3$H-NECA bound in the absence of a test compound.
3. "N" means the amount of radioactivity of $^3$H-NECA bound in the presence of 100 μM CPA.

The similar procedure as above was repeated to determine the radioactivity bound to the $A_2$ receptors using 50 μl of CGS 21680 labeled with tritium [$^3$H-2-[p-(2-carboxyethyl)-phenethylamino] -5'-(N-ethylcarboxamide)adenosine: 40 Ci/mmol, manufactured by New England Nuclear Co. (J. Pharmacol. Exp. Ther., 251, 888 (1989)] (final concentration: 4.0 nM) in place of 50 Bl of the mixture of N-ethylcarboxamidoadenosine labeled with tritium ($^3$H-NECA: 26 Ci/mmol, manufactured by Amersham Co.) (final concentration: 3.8 nM) and cyclopentyladenosine (CPA, manufactured by Sigma Co.) (final concentration: 50 nM).

The inhibition rate of the test compound against the binding of $A_2$ receptors ($^3$H-CGS 21680 binding) was calculated by the following equation:

$$\text{Inhibition Rate (\%)} = \left(1 - \frac{[B] - [N]}{[T] - [N]}\right) \times 100$$

[Notes]
1. "B" means the amount of radioactivity of $^3$H-CGS 21680 bound in the presence of a test compound at a concentration shown in Table 4.
2. "T" means the amount of radioactivity of $^3$H-CGS 21680 bound in the absence of a test compound.
3. "N" means the amount of radioactivity of $^3$H-CGS 21680 bound in the presence of 100 μM CPA.

The results are shown in Table 4. The Ki value ($^3$H-NECA binding) shown in the table was calculated by the following equation:

$$Ki = \frac{IC_{50}}{1 + \frac{L}{Kd} + \frac{C}{Kc}}$$

[Notes]
$IC_{50}$: Concentration at which the inhibition rate is 50%
L: Concentration of $^3$H-NECA
Kd: Dissociation constant of $^3$H-NECA
C: Concentration of CPA
Kc: Inhibition constant of CPA

TABLE 4

| | $A_2$ Receptor | | | | | Ratio |
|---|---|---|---|---|---|---|
| | Inhibition (%) | | | | $K_i$ | |
| Compd. | $10^{-7}$M | $10^{-6}$M | $10^{-5}$M | $10^{-4}$M | (nM) | ($A_1/A_2$) |
| 64 | 53 | 86 | 98 | 100 | 23 | |
| 65 | 67 | 79 | 94 | 92 | 12 | |
| 67 | 57 | 84 | 88 | 90 | 33 | |
| 70 | 65 | 88 | 75 | 83 | 15 | >670 |
| 71 | 80 | 99 | 95 | 74 | 3.9 | |

TABLE 4-continued

| Compd. | | | | | | |
|---|---|---|---|---|---|---|
| 72 | 79 | 84 | 73 | 86 | 3.1 | >32,000 |
| 73 | 91 | 94 | 90 | 93 | 2.0 | |
| 76 | 77 | 84 | 88 | 95 | 9.5 | |
| 77 | 85 | 91 | 96 | 98 | 1.6 | |
| 78 | 53 | 64 | 70 | 70 | 15 | |
| 79 | 80 | 96 | 88 | 93 | 6.1 | |
| 80 | 70 | 69 | 80 | 80 | 6.3 | >16,000 |
| 81 | 84 | 90 | 104 | 98 | 1.5 | |
| 82 | 65 | 87 | 92 | 91 | 310 | >320 |
| 83 | 51 | 83 | 90 | 88 | 50 | >2,000 |
| 84 | 56 | 68 | 83 | 79 | 22 | |
| 85 | 78 | 85 | 78 | 81 | 3.0 | >33,000 |
| 86 | 38 | 60 | 90 | 81 | | |
| 87 | 62 | 57 | 75 | 85 | 26 | >3,800 |

| | $A_2$ Receptor Inhibition (%) | | | |
|---|---|---|---|---|
| Compd. | $10^{-7}$M | $10^{-6}$M | $10^{-5}$M | $10^{-4}$M |
| 88 | | | 76 | 70 |
| 89 | 27 | 59 | 75 | 79 |
| 90 | | | 89 | 90 |
| 91 | 46 | 80 | 86 | 99 |
| 94 | 74 | 82 | 89 | 79 |
| 95 | 83 | 84 | 82 | 98 |
| 96 | | | 93 | 92 |
| 97 | 86 | 93 | 90 | 94 |
| 112 | 73 | 76 | 108 | 112 |
| 113 | 88 | 95 | 88 | 93 |
| 114 | | | 88 | 91 |
| 115 | 78 | 88 | 81 | 83 |
| 117 | 63 | 94 | 95 | 96 |
| 118 | 56 | 65 | 77 | 81 |
| 119 | 74 | 92 | 97 | 99 |
| 121 | | | 84 | 78 |
| 123 | | | 75 | 84 |
| 126 | | | 74 | 79 |

| | $A_2$ Receptor Inhibition (%) | | | $A_2$ Receptor Inhibition (%) | |
|---|---|---|---|---|---|
| Compd. | $10^{-7}$M | $10^{-6}$M | Compd. | $10^{-7}$M | $10^{-6}$M |
| 98 | 54 | 71 | 149 | 29* | 73* |
| 99 | 71 | 101 | 150 | 59* | 66* |
| 100 | 56 | 60 | 152 | 59* | 78* |
| 101 | 71 | 94 | 153 | 85* | 94* |
| 102 | 80* | 88* | 154 | 9* | 51* |
| 103 | 88* | 98* | 155 | 93* | 103* |
| 104 | 27* | 52* | 156 | 53* | 85* |
| 105 | 46* | 87* | 157 | 71* | 98* |
| 106 | 68* | 70* | 158 | 75* | 89* |
| 107 | 64* | 103* | 159 | 84* | 101* |
| 110 | 67* | 92* | 160 | 66* | 87* |
| 111 | 83* | 99* | 161 | 92* | 95* |
| 127 | 89* | 94* | 162 | 25 | 64 |
| 128 | 64 | 64 | 164 | 36* | 76* |
| 129 | 78 | 93 | 165 | 70* | 94* |
| 130 | 73 | 73 | 166 | 75* | 102* |
| 131 | 81 | 88 | 168 | 76* | 96* |
| 133 | 76 | 84 | 169 | 83* | 94* |
| 137 | 59* | 87* | 170 | 93* | 84* |
| 139 | 30 | 69 | 171 | 87* | 94* |
| 140 | 54* | 54* | 172 | 97* | 96* |
| 141 | 68* | 89* | 173 | 61* | 96* |
| 142 | 53* | 79* | 175 | 79* | 95* |
| 143 | 72* | 86* | 176 | 34* | 68* |
| 144 | 78* | 95* | 177 | 23* | 87* |
| 145 | 86* | 98* | 178 | 34* | 79* |
| 146 | 75* | 70* | 183 | 89* | 75* |
| 147 | 82* | 100* | | | |

*; [$^3$H]CGS 21680 was used.

As shown in Tables 3 and 4, Compounds (I) and pharmaceutically acceptable salts thereof exhibit an extremely potent affinity especially for adenosine $A_2$ receptors.

EXPERIMENTAL EXAMPLE 3

Effect on Locomotor Activity in Parkinson's Disease Model in Mice

1-Methyl-4-phenyl-1,2,3,6-tetrahydropyridine (MPTP) is known to cause an acute Parkinson's syndrome (parkinsonism) when administered to humans. The syndrome resembles spontaneous parkinsonism in terms of cardinal symptoms (muscular rigidity, bradycinesia, and resting tremor) and pathological phenomena (extensive degeneration of the nigrostriatal dopamine system) [Science, 219, 979 (1983)]. MPTP-treated mice also exhibit the syndrome similar to parkinsonism [Science, 224, 1451 (1984)].

Especially, MPTP-treated C57BL/6 mice have been reported to serve as a suitable model for Parkinson's disease. In this strain of mice, striatal dopamine is remarkably decreased and locomotor activity is profoundly depressed [Brain Res., 528, 181 (1990)].

The experiment was performed by using several groups of 7-weeks-old male C57BL/6 mice (weighing 20 to 24 g, Japan SLC), each group consisting of 8 mice. MPTP (Aldrich Chemical Co., Inc.) dissolved in a physiological saline solution (Otsuka Pharmaceutical Co., Ltd.) was intraperitoneally administered to each mouse once a day for five consecutive days at a dose of 30 mg/kg. A test compound was suspended in injectable distilled water (Otsuka Phamaceutical Co., Ltd.) containing Tween 80 [polyoxyethylene (20) sorbitan monooleate]. L-DOPA (Kyowa Hakko Kogyo Co., Ltd.) was suspended in 0.3% CMC (sodium carboxylmethylcellulose) and bromocriptine was suspended in injectable distilled water. Thirty minutes after the final MPTP administration, the test compound suspensions and the control suspension [injectable distilled water (Otsuka Pharmaceutical Co., Ltd.) containing Tween 80] containing no test compound were orally administered to separate groups of the mice (0.1 ml per 10 g of body weight). The amount of active movements (horizontal activity) of each mouse was measured by using Automex-II (Columbus Instruments International Corp.) for the period of 30 minutes starting 30 minutes after the administration of the test compound. Bromocriptine was administerd 3 hours proir to the final MPTP treatment, and the amount of active movements was measured for the period of 30 minutes from 1 hour after the MPTP treatment. The effect of the compounds was evaluated by comparing the average counts of the active movements of the test compound-administered groups with those of the control groups. Statistical comparison of the values was carried out by Student's t-test.

The results are shown in Table 5.

TABLE 5-1

| Group | Administration | | Dose of Test Compound (mg/kg) | Amount of Active Movements (average count ± S.E.M) |
|---|---|---|---|---|
| Normal | MPTP | (−) | — | 1875 ± 77.7 |
| Control | Test Compound | (−) | | |
| MPTP | MPTP | (+) | — | 207 ± 85.5## |
| | Test Compound | (−) | | |
| Compound 1 | MPTP | (+) | 10 | 628 ± 174.5* |
| | Compound 1 | (+) | | |
| Compound 2 | MPTP | (+) | 10 | 1134 ± 267.0* |
| | Compound 2 | (+) | | |

TABLE 5-1-continued

| Group | Administration | Dose of Test Compound (mg/kg) | Amount of Active Movements (average count ± S.E.M) |
|---|---|---|---|

: p < 0.01 (comparison with normal control group)
*: p < 0.05 (comparison with MPTP-treated group)

TABLE 5-2

| Group | Administration | | Dose of Test Compound (mg/kg) | Amount of Active Movements (average count ± S.E.M) |
|---|---|---|---|---|
| Normal Control | MPTP Test Compound | (−) (−) | — | 2185 ± 156.2 |
| MPTP | MPTP Test Compound | (+) (−) | — | 38 ± 24.2## |
| Compound 3 | MPTP Compound 3 | (+) (+) | 40 | 228 ± 82.6 |
| Compound 4 | MPTP Compound 4 | (+) (+) | 10 | 961 ± 164.7* |

: p < 0.01 (comparison with normal control group)
*: p < 0.05 (comparison with MPTP-treated group)

TABLE 5-3

| Group | Administration | | Dose of Test Compound (mg/kg) | Amount of Active Movements (average count ± S.E.M) |
|---|---|---|---|---|
| Normal Control | MPTP Test Compound | (−) (−) | — | 2255 ± 203.1 |
| MPTP | MPTP Test Compound | (+) (−) | — | 17 ± 4.9## |
| Compound 5 | MPTP Compound 5 | (+) (+) | 10 | 24 ± 6.5 |
| Compound 6 | MPTP Compound 6 | (+) (+) | 10 | 34 ± 12.1 |
| Compound 7 | MPTP Compound 7 | (+) (+) | 10 | 78 ± 48.3 |

: p < 0.01 (comparison with normal control group)

TABLE 5-4

| Group | Administration | | Dose of Test Compound (mg/kg) | Amount of Active Movements (average count ± S.E.M) |
|---|---|---|---|---|
| Normal Control | MPTP Test Compound | (−) (−) | — | 2032 ± 167.4 |
| MPTP | MPTP Test Compound | (+) (−) | — | 55 ± 16.8## |
| Compound 5 | MPTP Compound 5 | (+) (+) | 40 | 217 ± 84.2 |
| Compound 6 | MPTP Compound 6 | (+) (+) | 40 | 458 ± 153.7* |
| Compound 7 | MPTP Compound 7 | (+) (+) | 40 | 310 ± 119.5 |

: p < 0.01 (comparison with normal control group)
*: p < 0.05 (comparison with MPTP-treated group)

TABLE 5-5

| Group | Administration | | Dose of Test Compound (mg/kg) | Amount of Active Movements (average count ± S.E.M) |
|---|---|---|---|---|
| Normal Control | MPTP Test Compound | (−) (−) | — | 2252 ± 210.1 |
| MPTP | MPTP Test Compound | (+) (−) | — | 18 ± 8.4## |
| Compound 9 | MPTP Compound 9 | (+) (+) | 40 | 41 ± 18.0 |
| Compound 10 | MPTP Compound 10 | (+) (+) | 40 | 32 ± 21.2 |
| Compound 11 | MPTP Compound 11 | (+) (+) | 40 | 20 ± 7.1 |
| Compound 8 | MPTP Compound 8 | (+) (+) | 40 | 43 ± 28.3 |

: p < 0.01 (comparison with normal control group)

TABLE 5-6

| Group | Administration | | Dose of Test Compound (mg/kg) | Amount of Active Movements (average count ± S.E.M) |
|---|---|---|---|---|
| Normal Control | MPTP Test Compound | (−) (−) | — | 2210 ± 101.1 |
| MPTP | MPTP Test Compound | (+) (−) | — | 45 ± 10.7## |
| Compound 65 | MPTP Compound 65 | (+) (+) | 10 | 637 ± 160.0* |
| Compound 71 | MPTP Compound 71 | (+) (+) | 10 | 924 ± 219.5** |

: p < 0.01 (comparison with normal control group)
*: p < 0.05;
**: p < 0.01 (comparison with MPTP-treated group)

TABLE 5-7

| Group | Administration | | Dose of Test Compound (mg/kg) | Amount of Active Movements (average count ± S.E.M) |
|---|---|---|---|---|
| Normal Control | MPTP Test Compound | (−) (−) | — | 2205 ± 232.3 |
| MPTP | MPTP Test Compound | (+) (−) | — | 60 ± 20.8## |
| Compound 65 | MPTP Compound 65 | (+) (+) | 2.5 | 1265 ± 316.9** |
| Compound 71 | MPTP Compound 71 | (+) (+) | 2.5 | 800 ± 156.8** |

: p < 0.01 (comparison with normal control group)
**: p < 0.01 (comparison with MPTP-treated group)

TABLE 5-8

| Group | Administration | | Dose of Test Compound (mg/kg) | Amount of Active Movements (average count ± S.E.M) |
|---|---|---|---|---|
| Normal Control | MPTP Test Compound | (−) (−) | — | 2078 ± 180.2 |
| MPTP | MPTP Test Compound | (+) (−) | — | 132 ± 65.3## |
| Compound 65 | MPTP Compound 65 | (+) (+) | 0.63 | 610 ± 147.9* |

TABLE 5-8-continued

| Group | Administration | Dose of Test Compound (mg/kg) | Amount of Active Movements (average count ± S.E.M) |
|---|---|---|---|

: $p < 0.01$ (comparison with normal control group)
*: $p < 0.05$ (comparison with MPTP-treated group)

TABLE 5-9

| Group | Administration | Dose of Test Compound (mg/kg) | Amount of Active Movements (average count ± S.E.M) |
|---|---|---|---|
| Normal Control | MPTP | (−) | |
| | Test Compound | (−) | 2326 ± 147.1 |
| MPTP | MPTP | (+) | |
| | Test Compound | (−) | 71 ± 37.2## |
| Compound 73 | MPTP | (+) | |
| | Compound 73 | (+) | 10 | 754 ± 174.2** |
| Compound 77 | MPTP | (+) | |
| | Compound 77 | (+) | 10 | 817 ± 163.1** |

: $p < 0.01$ (comparison with normal control group)
**: $p < 0.01$ (comparison with MPTP-treated group)

TABLE 5-10

| Group | Administration | Dose of Test Compound (mg/kg) | Amount of Active Movements (average count ± S.E.M) |
|---|---|---|---|
| Normal Control | MPTP | (−) | |
| | Test Compound | (−) | 2574 ± 165.9 |
| MPTP | MPTP | (+) | |
| | Test Compound | (−) | 21 ± 5.1## |
| Compound 97 | MPTP | (+) | |
| | Compound 97 | (+) | 10 | 157 ± 25.0** |

: $p < 0.01$ (comparison with normal control group)
**: $p < 0.01$ (comparison with MPTP-treated group)

TABLE 5-11

| Group | Administration | Dose of Test Compound (mg/kg) | Amount of Active Movements (average count ± S.E.M) |
|---|---|---|---|
| Normal Control | MPTP | (−) | |
| | Test Compound | (−) | 2349 ± 121.7 |
| MPTP | MPTP | (+) | |
| | Test Compound | (−) | 44 ± 14.4## |
| Compound 83 | MPTP | (+) | |
| | Compound 83 | (+) | 2.5 | 937 ± 189.5** |
| Compound 170 | MPTP | (+) | |
| | Compound 170 | (+) | 2.5 | 604 ± 192.6 |
| Compound 195 | MPTP | (+) | |
| | Compound 195 | (+) | 10 | 922 ± 208.2** |

: $p < 0.01$ (comparison with normal control group)
**: $p < 0.05$;
**: $p < 0.01$ (comparison with MPTP-treated group)

TABLE 5-12

| Group | Administration | Dose of Test Compound (mg/kg) | Amount of Active Movements (average count ± S.E.M) |
|---|---|---|---|
| Normal Control | MPTP | (−) | |
| | Test Compound | (−) | 1875 ± 77.7 |
| MPTP | MPTP | (+) | |
| | Test Compound | (−) | 207 ± 85.5## |
| L-DOPA | MPTP | (+) | |
| | L-DOPA | (+) | 300 | 561 ± 271.01[1)] |

: $p < 0.01$ (comparison with normal control group)
[1)]: no significant difference as compared with MPTP-treated group

TABLE 5-13

| Group | Administration | Dose of Test Compound (mg/kg) | Amount of Active Movements (average count ± S.E.M) |
|---|---|---|---|
| Normal Control | MPTP | (−) | |
| | Test Compound | (−) | 1984 ± 122.3 |
| MPTP | MPTP | (+) | |
| | Test Compound | (−) | 41 ± 14.3## |
| Bromocriptine | MPTP | (+) | |
| | Bromocriptine | (+) | 40 | 1739 ± 494.9** |

: $p < 0.01$ (comparison with normal control group)
**: $p < 0.01$ (comparison with MPTP-treated group)

TABLE 5-14

| Group | Administration | Dose of Test Compound (mg/kg) | Amount of Active Movements (average count ± S.E.M) |
|---|---|---|---|
| Normal Control | MPTP | (−) | |
| | Test Compound | (−) | 2574 ± 165.9 |
| MPTP | MPTP | (+) | |
| | Test Compound | (−) | 21 ± 5.1## |
| Bromocriptine | MPTP | (+) | |
| | Bromocriptine | (+) | 10 | 66 ± 35.4[1)] |

: $p < 0.01$ (comparison with normal control group)
[1)]: no significant difference as compared with MPTP-treated group

EXPERIMENTAL EXAMPLE 4

Effect on Haloperidol-Induced Catalepsy

Parkinson's disease is a clinical syndrome caused by degeneration of nigrostriatal dopaminergic neurons. Systemic administration of haloperidol (dopamine $D_1/D_2$ antagonist) induces catalepsy resulting from the blockade of postsynaptic dopamine $D_2$ receptors. It is generally accepted that this haloperidol-induced catalepsy is a classical model of parkinsonism in humans [Eur. J. Pharmacol., 182, 327 (1990)].

The experiment was performed by using several groups of 5-weeks-old male ddY mice (weighing 22 to 24 g, Japan SLC), each group consisting of 5 mice. Haloperidol (Janssen Pharmaceutica) suspended in 0.3% CMC was intraperitoneally administered to each mouse at a dose of 1.0 mg/kg.

Test compounds were suspended in 0.3% CMC or in injectable distilled water (Otsuka Pharmaceutical Co., Ltd.) containing Tween 80. L-DOPA (Kyowa Hakko Kogyo Co., Ltd.) and benserazide hydrochloride (Kyowa Hakko Kogyo Co., Ltd.) were suspended in 0.3% CMC. One hour after the haloperidol administration, the test compound suspensions and the control suspension [0.3% CMC or injectable distilled water (Otsuka Pharmaceutical Co., Ltd.) containing Tween 80] containing no test compound were orally administered to separate groups of the mice (0.1 ml per 10 g of body weight). One hour after the administration of the test compound, the forelimbs of each mouse and subsequently the hindlimbs of the same mouse were placed on a 4.5 cm-high, 1.0 cm-wide bar and catalepsy was estimated. All of the test compounds were orally administered at a dose of 10 mg/kg, and L-DOPA (100 mg/kg) and benserazide (25 mg/kg) were intraperitoneally administered together as a control experiment. The catalepsy score and the standard of judgment are shown below.

| score | duration of the cataleptic posture | |
|---|---|---|
| 0: | forelimbs | less than 5 seconds |
|  | hindlimbs | less than 5 seconds |
| 1: | forelimbs | from 5 (inclusive) to 10 (exclusive) seconds |
|  | hindlimbs | less than 5 seconds |
| 2: | forelimbs | 10 seconds or more |
|  | hindlimbs | less than 5 seconds |
| 3: | forelimbs | from 5 (inclusive) to 10 (exclusive) seconds |
|  | hindlimbs | from 5 (inclusive) to 10 (exclusive) seconds; |
|  | or forelimbs | less than 5 seconds |
|  | hindlimbs | 5 seconds or more |
| 4: | forelimbs | 10 seconds or more |
|  | hindlimbs | from 5 (inclusive) to 10 (exclusive) seconds; |
|  | or forelimbs | from 5 (inclusive) to 10 (exclusive) seconds |
|  | hindlimbs | 10 seconds or more |
| 5: | forelimbs | 10 seconds or more |
|  | hindlimbs | 10 seconds or more |

The effect of the compounds was evaluated by the total of the catalepsy scores of five mice in each group (25 points at the full). The groups wherein the total score was not more than 20 points were estimated to be effective. The number of the animals showing remission against catalepsy is the number of the mice for which the catalepsy score was not more than 4 points. The remission rate shows the rate of decrease in total score based on that of the control group.

The ED50 (50% effective dose) values were determined using ten mice at each dose. A test compound was judged to be effective at the dose where the catalepsy score was 3 or less than 3. The ED50 values were calculated by Probit analysis.

The results are shown in Table 6.

TABLE 6

| Compound | Total Score | Number of the Animals Showing Remission | Remission Rate (%) | $ED_{50}$ (mg/kg) |
|---|---|---|---|---|
| 0.3% CMC (Control) | 25 | 0 | 0 | |
| L-DOPA + benserazide | 20 | 3 | 20 | |
| 1 | 13 | 5 | 48 | 2.7 |

TABLE 6-continued

| Compound | Total Score | Number of the Animals Showing Remission | Remission Rate (%) | $ED_{50}$ (mg/kg) |
|---|---|---|---|---|
| 2 | 11 | 5 | 56 | 0.13 |
| 3 | 20 | 4 | 20 | |
| 4 | 20 | 4 | 20 | |
| 5 | 18 | 4 | 28 | 3.6 |
| 6 | 19 | 3 | 24 | |
| 7 | 13 | 4 | 48 | 0.38 |
| 11 | 20 | 3 | 20 | |
| L-DOPA + benserazide | 18 | 4 | 28 | 107.5 |
| 13 | 5 | 5 | 80 | 3.0 |
| 15 | 19 | 4 | 24 | |
| 16 | 20 | 4 | 20 | |
| 18 | 20 | 4 | 20 | |
| 19 | 19 | 3 | 24 | |
| 20 | 19 | 3 | 24 | |
| 23 | 18 | 4 | 28 | |
| 24 | 19 | 4 | 24 | |
| 0.3% Tween 80 (Control) | 25 | 0 | 0 | |
| L-DOPA + benserazide | 18 | 4 | 28 | 107.5 |
| 9 | 15 | 5 | 40 | |
| 17 | 7 | 5 | 72 | 7.0 |
| 21 | 2 | 5 | 92 | 1.2 |
| 25 | 12 | 5 | 52 | 6.6 |
| 31 | 18 | 4 | 28 | |
| 33 | 16 | 5 | 36 | |
| 48 | 6 | 5 | 76 | 1.1 |
| 50 | 19 | 3 | 24 | |
| 53 | 20 | 4 | 20 | |
| 59 | 19 | 5 | 24 | |
| 0.3% Tween 80 (Control) | 25 | 0 | 0 | |
| L-DOPA + benserazide | 18 | 4 | 28 | 107.5 |
| 65 | 2 | 5 | 80 | 0.03 |
| 69 | 6 | 5 | 76 | 1.7 |
| 71 | 2 | 5 | 92 | 0.23 |
| 73 | 8 | 5 | 68 | 0.24 |
| 75 | 12 | 5 | 52 | 2.7 |
| 77 | 1 | 5 | 92 | 0.6 |
| 79 | 4 | 5 | 84 | 0.76 |
| 81 | 4 | 5 | 84 | 1.9 |
| 83 | 7 | 5 | 72 | 0.35 |
| 84 | 19 | 4 | 24 | |
| 85 | 20 | 3 | 20 | |
| 94 | 16 | 4 | 36 | |
| 95 | 17 | 4 | 32 | |
| 97 | 8 | 5 | 68 | 2.6 |
| 99 | 6 | 5 | 76 | 1.5 |
| 101 | 8 | 4 | 68 | 2.5 |
| 103 | 3 | 5 | 88 | |
| 107 | 17 | 3 | 32 | |
| 113 | 19 | 4 | 24 | 3.8 |
| 115 | 10 | 5 | 60 | 1.7 |
| 0.3% Tween 80 (Control) | 25 | 0 | 0 | |
| L-DOPA + benserazide | 18 | 4 | 28 | 107.5 |
| 117 | 18 | 5 | 28 | |
| 119 | 14 | 5 | 44 | |
| 126 | 17 | 3 | 32 | |
| 127 | 16 | 4 | 36 | |
| 130 | 9 | 5 | 64 | |
| 131 | 5 | 5 | 80 | |
| 133 | 14 | 4 | 44 | |
| 139 | 15 | 4 | 40 | |
| 141 | 18 | 3 | 28 | |
| 145 | 9 | 5 | 64 | |
| 147 | 17 | 4 | 32 | |
| 149 | 16 | 3 | 36 | |
| 153 | 14 | 4 | 44 | |
| 155 | 12 | 4 | 52 | |
| 166 | 16 | 3 | 36 | |

TABLE 6-continued

| Compound | Total Score | Number of the Animals Showing Remission | Remission Rate (%) | $ED_{50}$ (mg/kg) |
|---|---|---|---|---|
| 170 | 3 | 5 | 92 | 0.01 |
| 172 | 4 | 5 | 84 | |
| 173 | 20 | 3 | 20 | |
| 175 | 4 | 5 | 84 | |
| 176 | 19 | 3 | 24 | |
| 188 | 19 | 3 | 24 | |
| 189 | 13 | 3 | 48 | |
| 191 | 2 | 5 | 92 | 0.02 |
| 193 | 12 | 4 | 52 | |

EXPERIMENTAL EXAMPLE 5

Augmentation of the Contralateral Rotation in Rats with a 6-Hydroxydopamine-Induced Unilateral Lesion of the Nigrostriatal Dopamine Pathway When a unilateral lesion of the nigrostriatal pathway is induced by 6-hydroxydopamine in rodents, the sensitivity of dopamine receptors in the denervated striatum is enhanced. Administration of a dopamine agonist to the rodents in such a condition induces a rotational behavior to the side contralateral to the lesioned side [Acta Physiol. Scand., 367, 69 (1971)]. This model has been used for a long time as a model for the study of Parkinson's disease and in the screening of drugs for this disease [Neurol. Neurobiol., 33, 1 (1987)].

Male Sprague-Dawley rats (weighing 200 to 240 g, Japan SLC) were pretreated with desipramine hydrochloride (25 mg/kg, i.p., Sigma Co.) 30 minutes before surgery to protect noradrenergic neurons. Then, the animals were anesthetized with sodium pentobarbital (30 mg/kg, i.p., Dainippon Pharm. Co., Ltd.) and the nigrostriatal pathway was lesioned by injection of 6-hydroxydopamine hydrobromide (8 μg, Sigma Co.) into the left medial forebrain bundle. 6-Hydroxydopamine hydrobromide was dissolved in physiological saline containing 0.05% L-ascorbic acid (Wako Pure Chem. Industries, Ltd.) to make 2 μl of solution and injected over 3 minutes.

More than 10 days after surgery, each rat was placed in a plastic bowl (30 cm in diameter). Apomorphine (0.1 mg/kg, Sandoz, AG) was injected subcutaneously and the rats which showed a rotational behavior to the side contralateral to the lesioned side at a frequency of more than 600 counts/60 minutes after apomorphine administration were used for screening. The number of rotations was counted with an automated rotometer, in which each 180° turn was counted as a rotation.

Test compounds were suspended in 0.3% sodium carboxymethylcellulose and administered orally at a dose of 1 mg/kg 30 minutes before the injection of apomorphine (0.1 mg/kg, s.c.). The counts of rotations were summed up every 5 minutes for 150 minutes after apomorphine administration. The total rotation counts induced by apomorphine (0.1 mg/kg, s.c.) with and without a test compound were statistically compared, using the same animals. Rats were allowed to rest more than 5 days between each experiment. Statistical comparison of the values was carried out by Sign-Wilcoxon test.

The results are shown in Table 7.

TABLE 7

| | total amount of rotations (average count ± S.E.M.) | |
|---|---|---|
| Compd. | apomorphine | test compound + apomorphine |
| 65 | 1102 ± 94 | 1584 ± 196* |
| 71 | 1003 ± 84 | 1406 ± 155* |
| 73 | 1097 ± 147 | 1637 ± 127* |
| 77 | 1006 ± 81 | 1378 ± 216* |
| 170 | 1041 ± 51 | 1490 ± 146* |

*: $p < 0.05$

As described above, Compounds (I) and pharmaceutically acceptable salts thereof exhibit anti-Parkinson's syndrome effects. Thus, they are effective as therapeutic agents for Parkinson's disease. Compounds (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol and fructose, glycols such as polyethylene glycol and propylene glycol, oils such as sesame oil, olive oil and soybean oil, preservatives such as p-hydroxybenzoates, flavors such as strawberry flavor and peppermint, and the like. Powders, pills, capsules and tablets can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like. Tablets and capsules are most useful oral unit dose forms because of the readiness of administration. For preparing tablets and capsules, solid pharmaceutical carriers are used.

Injectable preparations can be prepared using a carrier such as distilled water, a salt solution, a glucose solution or a mixture of a salt solution and a glucose solution. The preparations can be prepared in the form of solution, suspension or dispersion according to a conventional method by using a suitable auxiliary.

Compounds (I) and pharmaceutically acceptable salts thereof can be administered orally in the said dosage forms or parenterally as injections. The effective dose and the administration schedule vary depending upon mode of administration, age, body weight and conditions of a patient, etc. However, generally, Compound (I) or a pharmaceutically acceptable salt thereof is administered in a daily dose of 0.01 to 25 mg/kg in 3 to 4 parts.

Certain embodiments of the invention are illustrated in the following examples.

EXAMPLE 1

(E)-8-[2-(1,4-Benzodioxan-6-yl)vinyl]-1,3-dipropyl-xanthine (Compound 16)

Substantially the same procedure as in Reference Example 1 was repeated using 1.35 g (5.96 mmol) of 5,6-diamino-1,3-dipropyluracil and 1.35 g (6.55 mmol) of 3-(1,4-benzodioxan-6-yl)acrylic acid. Then, the resultant crude crystals were recrystallized from ethanol/water to give 1.54 g (yield 65%) of Compound 16 as white needles.

Melting Point: >275° C.; Elemental Analysis: $C_{21}H_{24}N_4O_4$, Calcd. (%): C, 63.62; H, 6.10; N, 14.13; Found (%): C, 63.57; H, 6.24; N, 14.36; IR (KBr) $v_{max}$ (cm$^{-1}$): 1693, 1636, 1582, 1511; NMR (DMSO-d$_6$; 270 MHz)δ(ppm): 12.52(1H, brs), 7.63 (1H, d, J=16.2 Hz), 7.10–7.06(2H, m), 6.95–6.86(2H, m), 4.29 (4H, s), 4.15–4.10 (4H, m), 1.90–1.65 (4H, m), 1.05–0.95 (6H, m).

EXAMPLE 2

(E)-8-[2-(1,4-Benzodioxan-6-yl)vinyl]-7-methyl-1,3-dipropylxanthine (Compound 17)

Substantially the same procedure as in Reference Example 1 was repeated using 1.0 g (2.52 mmol) of Compound 16 obtained in Example 1 in place of Compound B. Then, the resultant crude crystals were recrystallized from ethanol to give 840 mg (yield 81%) of Compound 17 as pale yellow needles.

Melting Point: 181.9°–182.3° C.; Elemental Analysis: $C_{22}H_{26}N_4O_4$, Calcd. (%): C, 64.37; H, 6.38; N, 13.64; Found (%): C, 64.56; H, 6.63; N, 13.92; IR (KBr) $v_{max}$ (cm$^{-1}$): 1693, 1651, 1510, 1288; NMR (CDCl$_3$; 270 MHz)δ(ppm): 7.67(1H, d, J=15.5 Hz), 7.10 (2H, m), 6.88 (1H, d, J=8.3 Hz), 6.74 (1H, d, J=15.5 Hz), 4.30(4H, m), 4.13–3.95(4H, m), 4.03(3H, s), 1.88–1.65(4H, m), 1.03–0.94(6H, m).

EXAMPLE 3

(E)-8-(3,4-Methylenedioxystyryl)-1,3-dipropylxanthine (Compound 18)

Substantially the same procedure as in Reference Example 1 was repeated using 4.25 g (18.8 mmol) of 5,6-diamino-1,3-dipropyluracil and 4.33 g (22.6 mmol) of 3,4-methylenedioxycinnamic acid. Then, the resultant crude crystals were recrystallized from dioxane to give 4.92 g (yield 69%) of Compound 18 as a pale yellow powder.

Melting Point: >270° C.; Elemental Analysis: $C_{20}H_{22}N_4O_4 \cdot 0.75H_2O$, Calcd. (%): C, 60.50; H, 5.72; N, 14.43; Found (%): C, 60.67; H, 5.98; N, 14.15; IR (KBr) $v_{max}$ (cm$^{-1}$): 1688, 1648, 1499; NMR (DMSO-d$_6$; 270 MHz)δ(ppm): 13.49(1H, brs), 7.56 (1H, d, J=16.3 Hz), 7.30 (1H, s), 7.07 (1H, d, J=8.4 Hz), 6.97–6.89 (2H, m), 6.07 (2H, s), 3.98 (2H, t, J=7.2 Hz), 3.85(2H, t, J=7.3 Hz), 1.75–1.35(4H, m), 0.95–0.80(6H, m).

EXAMPLE 4

(E)-7-Methyl-8-(3,4-methylenedioxystyryl)-1,3-dipropylxanthine (Compound 19)

Substantially the same procedure as in Reference Example 1 was repeated using 3.0 g (7.85 mmol) of Compound obtained in Example 3 in place of Compound B. Then, the resultant crude crystals were recrystallized from toluene/cyclohexane to give 2.33 g (yield 75%) of Compound as a pale green powder.

Melting Point: 151.7°–155.4° C.; Elemental Analysis: $C_{21}H_{24}N_4O_4 \cdot 0.25H_2O$, Calcd. (%): C, 62.91; H, 6.16; N, 13.97; Found (%): C, 62.88; H, 6.25; N, 13.72; IR (KBr) $v_{max}$ (cm$^{-1}$): 1689, 1650, 1498, 1443 NMR (CDCl$_3$; 270 MHz)δ(ppm): 7.70(1H, d, J=15.6 Hz), 7.10–6.95(2H, m), 6.84(1H, d, J=7.9 Hz), 6.72 (1H, d, J=15.6 Hz), 6.02(2H, s), 4.10(2H, t, J=7.3 Hz), 4.04(3H, s), 3.97(2H, t, J=7.3 Hz), 1.90–1.65(4H, m), 1.05–0.90 (6H, m).

EXAMPLE 5

(E)-8-[2-(4-Methoxynaphthyl)vinyl]-1,3-dipropylxanthine (Compound 61)

Substantially the same procedure as in Reference Example 1 was repeated using 3.0 g (13.3 mmol) of 5,6-diamino-1,3-dipropyluracil and 3.33 g (14.6 mmol) of 3-(4-methoxynaphthyl)acrylic acid. Then, the resultant crude crystals were recrystallized from dioxane/water to give 3.12 g (yield 56%) of Compound 61 as yellow needles.

Melting Point: >280° C.; Elemental Analysis: $C_{24}H_{26}N_4O_3$, Calcd. (%): C, 68.88; H, 6.26; N, 13.39; Found (%): C, 68.90; H, 6.38; N, 13.49; IR (KBr) $v_{max}$ (cm$^{-1}$): 1699, 1649, 1486, 1273; NMR (DMSO-d$_6$; 270 MHz)δ(ppm): 13.58 (1H, brs), 8.43 (1H, d, J=16.5 Hz), 8.36(1H, d, J=8.6 Hz), 8.24(1H, d, J=8.6 Hz), 7.98 (1H, d, J=7.8 Hz), 7.70–7.54 (2H, m), 7.12–7.06 (2H, m), 4.03 (3H, s), 4.02–3.86 (4H, m), 1.79–1.56(4H, m), 0.92(3H, s), 0.89(3H, s).

EXAMPLE 6

(E)-8-[2-(4-Methoxynaphthyl)vinyl]-7-methyl-1,3-dipropylxanthine (Compound 62)

Substantially the same procedure as in Reference Example 1 was repeated using 1.6 g (3.82 mmol) of Compound 61 obtained in Example 5 in place of Compound B. Then, the resultant crude crystals were recrystallized from ethyl acetate to give 1.25 g (yield 76%) of Compound 62 as pale yellow plates.

Melting Point: 212.6°–213.9° C.; Elemental Analysis: $C_{25}H_{28}N_4O_3$, Calcd. (%): C, 69.43; H, 6.52; N, 12.95; Found (%): C, 69.46; H, 6.68; N, 12.95; IR (KBr) $v_{max}$ (cm$^{-1}$): 1701, 1650, 1486, 1439, 1267; NMR (CDCl$_3$; 270 MHz)δ(ppm): 8.52(1H, d, J=15.5 Hz), 8.34(1H, d, J=8.3 Hz), 8.23(1H, d, J=8.6 Hz), 7.77 (1H, d, J=8.3 Hz), 7.66–7.52(2H, m), 6.89(1H, d, J=15.5 Hz), 6.87(1H, d, J=8.3 Hz), 4.18–4.11(2H, m), 4.07(3H, s), 4.06(3H, s), 4.02–3.97(2H, m), 1.95–1.64(4H, m), 1.03(3H, t, J=7.3 Hz), 0.98(3H, t, J=7.3 Hz).

EXAMPLE 7

(E)-8-(3,4-Dimethoxystyryl)-1,3-diethylxanthine (Compound 64)

3,4-Dimethoxycinnamic acid (1.39 g, 6.67 mmol) and 3-(3-diethylaminopropyl)-1-ethylcarbodiimide hydrochloride (1.74 g, 9.09 mmol) were added to a mixture of dioxane (40 ml) and water (20 ml) containing 5,6-diamino-1,3-diethyluracil [J. Am. Chem. Soc., 75, 114 (1953)] (1.20 g, 6.06 mmol). The resultant solution was stirred at room temperature for 2 hours at pH 5.5. After neutralization, the reaction solution was extracted three times with 50 ml of chloroform. The combined extract was washed with a saturated aqueous solution of sodium chloride and dried over anhydrous sodium sulfate, followed by evaporation under reduced pressure.

To the residue were added 10 ml of dioxane and 15 ml of an aqueous 1N sodium hydroxide solution, followed by heating under reflux for 20 minutes. After cooling, the solution was neutralized and 20 ml of chloroform was added thereto. The organic layer was separated and the aqueous layer was extracted twice with 20 ml of chloroform. The combined extract was washed with a saturated aqueous solution of sodium chloride and dried over anhydrous sodium sulfate, followed by evaporation under reduced pressure. The residue was purified by silica gel column chromatography (eluent: 2% methanol/chloroform), followed by recrystallization from toluene to give 1.06 g (yield 47%) of Compound 64 as pale yellow needles.

Melting Point: 268.8°–269.1° C.; Elemental Analysis: $C_{19}H_{22}N_4O_4$, Calcd. (%): C, 61.61; H, 5.98; N, 15.12; Found (%): C, 61.99; H, 6.00; N, 14.91; IR (KBr) $v_{max}$ ($cm^{-1}$): 1694, 1641, 1514, 1492; NMR (270 MHz; DMSO-$d_6$)δ(ppm): 13.35(1H, brs), 7.59 (1H, d, J=16.2 Hz), 7.27(1H, d, J=1.4 Hz), 7.14(1H, dd, J=1.4, 8.2 Hz), 6.99(1H, d, J=8.2 Hz), 6.96(1H, d, J=16.2 Hz), 4.06(2H, q, J=7.0 Hz), 3.91(2H, q, J=7.0 Hz), 3.83(3H, s), 3.79(3H, s), 1.26(3H, t, J=7.0 Hz), 1.14 (3H, t, J=7.0 Hz).

EXAMPLE 8

(E)-8-(3,4-Dimethoxystyryl)-1,3-diethyl-7-methylxanthine (Compound 65)

Compound 64 (1.20 g, 3.24 mmol) obtained in Example 7 was dissolved in 25 ml of dimethylformamide. To the solution were added 1.12 g (8.10 mmol) of potassium carbonate and subsequently 0.40 ml (6.49 mmol) of methyl iodide, and the resultant mixture was stirred at 50° C. for 30 minutes. After cooling, insoluble matters were filtered off, and 100 ml of water was added to the filtrate. The mixture was extracted three times with 50 ml of chloroform. The extract was washed twice with water and once with a saturated aqueous solution of sodium chloride, and dried over anhydrous sodium sulfate, followed by evaporation under reduced pressure. The obtained crude crystals were purified by silica gel column chromatography (eluent: 40% ethyl acetate/hexane), followed by recrystallization from isopropanol to give 840 mg (yield 68%) of Compound 65 as pale yellow needles.

Melting Point: 190.4°–191.3° C.; Elemental Analysis: $C_{20}H_{24}N_4O_4$, Calcd. (%): C, 62.48; H, 6.29; N, 14.57; Found (%): C, 62.52; H, 6.53; N, 14.56; IR (KBr) $v_{max}$ ($cm^{-1}$): 1697, 1655, 1518; NMR (270 MHz; $CDCl_3$)δ(ppm): 7.74(1H, d, J=15.5 Hz), 7.18(1H, dd, J=1.9, 8.3 Hz), 7.08(1H, d, J=1.9 Hz), 6.89(1H, d, J=8.3 Hz), 6.77(1H, d, J=15.5 Hz), 4.21 (2H, q, J=6.9 Hz), 4.09(2H, q, J=6.9 Hz), 4.06(3H, s), 3.96(3H, s), 3.93(3H, s), 1.39(3H, t, J=6.9 Hz), 1.27 (3H, t, J=6.9 Hz).

EXAMPLE 9

(E)-8-(2,3-Dimethoxystyryl)-1,3-diethylxanthine (Compound 66)

Substantially the same procedure as in Example 7 was repeated using 2.0 g (10.1 mmol) of 5,6-diamino-1,3-diethyluracil and 2.52 g (12.1 mmol) of 2,3dimethoxycinnamic acid. Then, the resultant crude crystals were recrystallized from dimethylsulfoxide/water to give 1.72 g (yield 46%) of Compound 66 as a white powder.

Melting Point: 287.5°–289.4° C.; Elemental Analysis: $C_{19}H_{22}N_4O_4$, Calcd. (%): C, 61.61; H, 5.98; N, 15.12; Found (%): C, 61.56; H, 6.11; N, 14.83; IR (KBr) $v_{max}$ ($cm^{-1}$): 1697, 1656, 1500; NMR (270 MHz; DMSO-$d_6$)δ(ppm): 13.64(1H, brs), 7.84 (1H, d, J=16.8 Hz), 7.29(1H, dd, J=1.7, 7.6 Hz), 7.15–7.00(3H, m), 4.07(2H, q, J=7.0 Hz), 3.94(2H, q, J=7.0 Hz), 3.83(3H, s), 3.79(3H, s), 1.26(3H, t, J=7.0 Hz), 1.14 (3H, t, J=7.0 Hz).

EXAMPLE 10

(E)-8-(2,3-Dimethoxystyryl)-1,3-diethyl-7-methylxanthine (Compound 67)

Substantially the same procedure as in Example 8 was repeated using 1.60 g (4.32 mmol) of Compound 66 obtained in Example 9 in place of Compound 64. Then, the resultant crude crystals were recrystallized from cyclohexane/toluene to give 1.21 g (yield 73%) of Compound 67 as a pale yellow powder.

Melting Point: 194.9°–195.6° C.; Elemental Analysis: $C_{20}H_{24}N_4O_4$, Calcd. (%): C, 62.48; H, 6.29; N, 14.57; Found (%): C, 62.67; H, 6.48; N, 14.31; IR (KBr) $v_{max}$ ($cm^{-1}$): 1694, 1660, 1272; NMR (270 MHz; $CDCl_3$)δ(ppm): 8.00(1H, d, J=16.8 Hz), 7.19(1H, dd, J=1.3, 7.9 Hz), 7.15–7.00(2H, m), 6.93 (1H, dd, J=1.3, 7.9 Hz), 4.26(2H, q, J=6.9 Hz), 4.09 (2H, q, J=6.9 Hz), 4.05 (3H, s), 3.91 (3H, s), 3.90 (3H, s), 1.39(3H, t, J=6.9 Hz), 1.27 (3H, t, J=6.9 Hz).

EXAMPLE 11

(E)-8-(2,4-Dimethoxystyryl)-1,3-diethylxanthine (Compound 68)

Substantially the same procedure as in Example 7 was repeated using 2.50 g (12.6 mmol) of 5,6-diamino-1,3diethyluracil and 2.89 g (13.9 mmol) of 2,4-dimethoxycinnamic acid. Then, the resultant crude crystals were recrystallized from dimethylformamide/ethanol to give 0.92 g (yield 20%) of Compound 68 as yellow crystals.

Melting Point: 278.7°–279.8° C.; Elemental Analysis: $C_{19}H_{22}N_4O_4$, Calcd. (%): C, 61.61; H, 5.98; N, 15.12; Found (%): C, 61.65; H, 5.95; N, 14.74; IR (KBr) $v_{max}$ ($cm^{-1}$): 1698, 1640, 1509, 1292; NMR (270 MHz; DMSO-$d_6$)δ(ppm): 13.43(1H, brs), 7.77 (1H, d, J=16.8 Hz), 7.54(1H, d, J=8.4 Hz), 6.95(1H, d, J=16.8 Hz), 6.63 (1H, d, J=2.5 Hz), 6.60 (1H, dd, J=2.5, 8.4 Hz), 4.06(2H, q, J=6.9 Hz), 3.93(2H, q, J=6.9 Hz), 3.89(3H, s), 3.82(3H, s), 1.25(3H, t, J=6.9 Hz), 1.13 (3H, t, J=6.9 Hz).

EXAMPLE 12

(E)-8-(2,4-Dimethoxystyryl)-1,3-diethyl-7-methylxanthine (Compound 69)

Substantially the same procedure as in Example 8 was repeated using 400 mg (1.08 mmol) of Compound 68 obtained in Example 11 in place of Compound 64. Then, the resultant crude crystals were recrystallized from hexane/ethyl acetate to give 335 mg (yield 81%) of Compound as yellow needles.

Melting Point: 195.9°–196.7° C.; Elemental Analysis: $C_{20}H_{24}N_4O_4$, Calcd. (%): C, 62.48; H, 6.29; N, 14.57; Found (%): C, 62.29; H, 6.51; N, 14.66; IR (KBr) $v_{max}$ ($cm^{-1}$): 1693, 1654, 1603, 1294; NMR (270 MHz; $CDCl_3$)δ(ppm): 7.93(1H, d, J=15.8 Hz), 7.48(1H, d, J=8.3 Hz), 6.97(1H, d, J=15.8 Hz), 6.53 (1H, dd, J=2.0, 8.3 Hz), 6.49(1H, d, J=2.0 Hz), 4.22 (2H, q, J=6.9 Hz), 4.08(2H, q, J=6.9 Hz), 4.02(3H, s), 3.92(3H, s), 3.86(3H, s), 1.38(3H, t, J=6.9 Hz), 1.26 (3H, t, J=6.9 Hz).

EXAMPLE 13

(E)-1,3-Diethyl-8-(2,3,4-trimethoxystyryl)xanthine (Compound 70)

Substantially the same procedure as in Example 7 was repeated using 2.5 g (12.6 mmol) of 5,6-diamino-1,3-diethyluracil and 2.3 g (13.9 mmol) of 2,3,4-trimethoxycinnamic acid. Then, the resultant crude crystals were recrystallized from dioxane/water to give 2.85 g (yield of Compound 70 as white crystals.

Melting Point: 276.3°–277.0° C.; Elemental Analysis: $C_{20}H_{24}N_4O_5$, Calcd. (%): C, 59.99; H, 6.04; N, 13.99; Found (%): C, 60.26; H, 6.24; N, 14.28; IR (KBr) $v_{max}$ (cm$^{-1}$): 1696, 1655, 1500; NMR (270 MHz; CDCl$_3$)δ(ppm): 12.39(1H, brs), 7.88(1H, d, J=16.3 Hz), 7.30(1H, d, J=8.4 Hz), 7.09(1H, d, J=16.3 Hz), 6.73(1H, d, J=8.4 Hz), 4.26(2H, q, J=6.9 Hz), 4.20 (2H, q, J=6.9 Hz), 3.96 (3H, s), 3.92 (3H, s), 3.91(3H, s), 1.41(3H, t, J=6.9 Hz), 1.29 (3H, t, J=6.9 Hz).

EXAMPLE 14

(E)-1,3-Diethyl-7-methyl-8-(2,3,4-trimethoxystyryl)xanthine (Compound 71)

Substantially the same procedure as in Example 8 was repeated using 1.5 g (3.75 mmol) of Compound 70 obtained in Example 13 in place of Compound 64. Then, the resultant crude crystals were recrystallized from hexane/ethyl acetate to give 1.32 g (yield 85%) of Compound 71 as colorless needles.

Melting Point: 152.9°–154.3° C.; Elemental Analysis: $C_{21}H_{26}N_4O_5$, Calcd. (%): C, 60.86; H, 6.32; N, 13.52; Found (%): C, 61.04; H, 6.44; N, 13.79; IR (KBr) $v_{max}$ (cm$^{-1}$): 1695, 1655, 1498, 1289; NMR (270 MHz; CDCl$_3$)δ(ppm): 7.88(1H, d, J=15.8 Hz), 7.28(1H, d, J=8.9 Hz), 7.01(1H, d, J=15.8 Hz), 6.72 (1H, d, J=8.9 Hz), 4.22(2H, q, J=6.9 Hz), 4.09(2H, q, J=6.9 Hz), 4.04 (3H, s), 3.97 (3H, s), 3.91 (3H, s), 3.90(3H, s), 1.38(3H, t, J=6.9 Hz), 1.27(3H, t, J=6.9 Hz).

EXAMPLE 15

(E)-1,3-Diethyl-8-(4-methoxy-2,3-dimethylstyryl)xanthine (Compound 72)

Substantially the same procedure as in Example 7 was repeated using 2.5 g (12.6 mmol) of 5,6-diamino-1,3-diethyluracil and 2.9 g (13.9 mmol) of 4-methoxy-2,3-dimethylcinnamic acid. Then, the resultant crude crystals were recrystallized from ethanol/water to give 0.80 g (yield of Compound 72 as white crystals.

Melting Point: >280.0° C.; Elemental Analysis: $C_{20}H_{24}N_4O_3$, Calcd. (%): C, 65.20; H, 6.56; N, 15.21; Found (%): C, 65.24; H, 6.61; N, 15.29; IR (KBr) $v_{max}$ (cm$^{-1}$): 1697, 1642, 1496, 1270; NMR (270 MHz; DMSO-d$_6$)δ(ppm): 13.52 (1H, brs), 7.93 (1H, d, J=15.8 Hz), 7.56(1H, d, J=8.2 Hz), 6.89(1H, d, J=8.2 Hz), 6.82 (1H, d, J=15.8 Hz), 4.06(2H, q, J=6.9 Hz), 3.94 (2H, q, J=6.9 Hz), 3.81(3H, s), 2.33 (3H, s), 2.13 (3H, s), 1.26 (3H, t, J=6.9 Hz), 1.14 (3H, t, J=6.9 Hz).

EXAMPLE 16

(E)-1,3-Diethyl-8-(4-methoxy-2,3-dimethylstyryl)-7-methylxanthine (Compound 73)

Substantially the same procedure as in Example 8 was repeated using 500 mg (1.36 mmol) of Compound 72 obtained in Example 15 in place of Compound 64. Then, the resultant crude crystals were recrystallized from hexane/ethyl acetate to give 493 mg (yield 95%) of Compound 73 as pale yellow needles.

Melting Point: 207.7°–208.3° C.; Elemental Analysis: $C_{21}H_{26}N_4O_3$, Calcd. (%): C, 65.95; H, 6.85; N, 14.65; Found (%): C, 66.24; H, 6.99; N, 14.69; IR (KBr) $v_{max}$ (cm$^{-1}$): 1698, 1651, 1267; NMR (270 MHz; CDCl$_3$)δ(ppm): 8.08(1H, d, J=15.2 Hz), 7.46(1H, d, J=8.9 Hz), 6.77(1H, d, J=8.9 Hz), 6.67 (1H, d, J=15.2 Hz), 4.22(2H, q, J=6.9 Hz), 4.09(2H, q, J=6.9 Hz), 4.03(3H, s), 3.86(3H, s), 2.40(3H, s), 2.21(3H, s), 1.39(3H, t, J=6.9 Hz), 1.26(3H, t, J=6.9 Hz).

EXAMPLE 17

(E)-1,3-Diethyl-8-(4-methoxy-2,5-dimethylstyryl)xanthine (Compound 74)

Substantially the same procedure as in Example 7 was repeated using 2.5 g (12.6 mmol) of 5,6-diamino-1,3-diethyluracil and 2.9 g (13.9 mmol) of 4-methoxy-2,5-dimethylcinnamic acid. Then, the resultant crude crystals were recrystallized from dioxane/water to give 2.43 g (yield 52%) of Compound 74 as white crystals.

Melting Point: >280.0° C.; Elemental Analysis: $C_{20}H_{24}N_4O_3$, Calcd. (%): C, 65.20; H, 6.56; N, 15.21; Found (%): 64.83; H, 6.56; N, 15.43; IR (KBr) $v_{max}$ (cm$^{-1}$): 1690, 1646, 1510, 1265; NMR (270 MHz; DMSO-d$_6$)δ(ppm): 13.52 (1H, brs), 7.82 (1H, d, J=16.3 Hz), 7.54 (1H, s), 6.86 (1H, d, J=16.3 Hz), 6.82 (1H, s), 4.06(2H, q, J=6.9 Hz), 3.94 (2H, q, J=6.9 Hz), 3.81(3H, s), 2.41(3H, s), 2.14 (3H, s), 1.25 (3H, t, J=6.9 Hz), 1.14 (3H, t, J=6.9 Hz).

EXAMPLE 18

(E)-1,3-Diethyl-8-(4-methoxy-2,5-dimethylstyryl)-7-methylxanthine (Compound 75)

Substantially the same procedure as in Example 8 was repeated using 1.10 g (2.98 mmol) of Compound 74 obtained in Example 17 in place of Compound 64. Then, the resultant crude crystals were recrystallized from ethyl acetate to give 0.76 g (yield 67%) of Compound 75 as yellow needles.

Melting Point: 235.4°–236.1° C.; Elemental Analysis: $C_{21}H_{26}N_4O_3$, Calcd. (%): C, 65.95; H, 6.85; N, 14.65; Found (%): C, 65.56; H, 6.93; N, 14.64; IR (KBr) $v_{max}$ (cm$^{-1}$): 1689, 1657, 1510, 1263; NMR (270 MHz; CDCl$_3$)δ(ppm): 7.97(1H, d, J=15.5 Hz), 7.42(1H, s), 6.71(1H, d, J=15.5 Hz), 6.66(1H, s), 4.22(2H, q, J=6.9 Hz), 4.09(2H, q, J=6.9 Hz), 4.05 (3H, s), 3.86 (3H, s), 2.48 (3H, s), 2.23 (3H, s), 1.38(3H, t, J=6.9 Hz), 1.26(3H, t, J=6.9 Hz).

EXAMPLE 19

(E)-8-(2,4-Dimethoxy-3-methylstyryl)-1,3-diethylxanthine (Compound 76)

Substantially the same procedure as in Example 7 was repeated using 2.0 g (10.1 mmol) of 5,6-diamino-1,3-diethyluracil and 2.04 g (9.19 mmol) of 2,4-dimethoxy-3- methylcinnamic acid. Then, the resultant crude crystals were recrystallized from dioxane/water to give 1.22 g (yield of Compound 76 as a yellow powder.

Melting Point: >275.0° C.; Elemental Analysis: $C_{20}H_{24}N_4O_4$, Calcd. (%): C, 62.48; H, 6.29; N, 14.57; Found (%): C, 62.28; H, 6.42; N, 14.22; IR (KBr) $v_{max}$ (cm$^{-1}$): 1696, 1635, 1592, 1499; NMR (270 MHz; DMSO-$d_6$)δ(ppm): 7.75 (1H, d, J=16.5 Hz), 7.58(1H, d, J=8.8 Hz), 6.99(1H, d, J=16.5 Hz), 6.85 (1H, d, J=8.8 Hz), 4.04(2H, q, J=6.9 Hz), 3.95(2H, q, J=6.9 Hz), 3.83(3H, s), 3.70(3H, s), 2.09(3H, s), 1.26(3H, t, J=6.9 Hz), 1.14(3H, t, J=6.9 Hz).

EXAMPLE 20

(E)-8-(2,4-Dimethoxy-3-methylstyryl)-1,3-diethyl-7-methylxanthine (Compound 77)

Substantially the same procedure as in Example 8 was repeated using 700 mg (1.82 mmol) of Compound 76 obtained in Example 19 in place of Compound 64. Then, the resultant crude crystals were recrystallized from cyclohexane/toluene to give 610 mg (yield 84%) of Compound as pale yellow needles.

Melting Point: 196.1°–196.8° C.; Elemental Analysis: $C_{21}H_{26}N_4O_4$, Calcd. (%): C, 63.30; H, 6.57; N, 14.06; Found (%): C, 63.32; H, 6.74; N, 14.13; IR (KBr) $v_{max}$ (cm$^{-1}$): 1695, 1649, 1498 NMR (270 MHz; CDCl$_3$)δ(ppm): 7.81(1H, d, J=15.8 Hz), 7.78(1H, d, J=8.6 Hz), 7.23(1H, d, J=15.8 Hz), 6.87 (1H, d, J=8.6 Hz), 4.07(2H, q, J=6.9 Hz), 4.01(3H, s), 3.92(2H, q, J=6.9 Hz), 3.85(3H, s), 3.70(3H, s), 2.10 (3H, s), 1.27 (3H, t, J=6.9 Hz), 1.13 (3H, t, J=6.9 Hz).

EXAMPLE 21

(E)-1,3-Diethyl-8-(3,4-methylenedioxystyryl)xanthine (Compound 78)

Substantially the same procedure as in Example 7 was repeated using 2.0 g (10.1 mmol) of 5,6-diamino-1,3-diethyluracil and 2.33 g (12.1 mmol) of 3,4methylenedioxycinnamic acid. Then, the resultant crude crystals were recrystallized from dimethylformamide/water to give 1.34 g (yield 38%) of Compound 78 as a yellowish green powder.

Melting Point: >275.0° C.; Elemental Analysis: $C_{18}H_{18}N_4O_4$, Calcd. (%): C, 61.01; H, 5.11; N, 15.81; Found (%): C, 61.16; H, 5.03; N, 15.80; IR (KBr) $v_{max}$ (cm$^{-1}$): 1685, 1638, 1499; NMR (270 MHz; DMSO-$d_6$)δ(ppm): 7.55(1H, d, J=16.3 Hz), 7.30(1H, s), 7.08(1H, d, J=8.9 Hz), 6.96(1H, d, J=8.9 Hz), 6.90 (1H, d, J=16.3 Hz), 6.07 (2H, s), 4.05 (2H, q, J=6.9 Hz), 3.93 (2H, q, J=6.9 Hz), 1.25 (3H, t, J=6.9 Hz), 1.10 (3H, t, J=6.9 Hz).

EXAMPLE 22

(E)-1,3-Diethyl-7-methyl-8-(3,4-methylenedioxystyryl)xanthine (Compound 79)

Substantially the same procedure as in Example 8 was repeated using 1.35 g (3.81 mmol) of Compound 78 obtained in Example 21 in place of Compound 64. Then, the resultant crude crystals were recrystallized from cyclohexane/toluene to give 940 mg (yield 67%) of Compound 79 as yellow needles.

Melting Point: 219.4°–219.6° C.; Elemental Analysis: $C_{19}H_{20}N_4O_4$, Calcd. (%): C, 61.94; H, 5.47; N, 15.20; Found (%): C, 62.09; H, 5.41; N, 15.16; IR (KBr) $v_{max}$ (cm$^{-1}$): 1687, 1657, 1569, 1498, 1443; NMR (270 MHz; CDCl$_3$)δ(ppm): 7.70 (1H, d, J=15.5 Hz), 7.10 (1H, d, J=1.6 Hz), 7.06(1H, dd, J=1.6, 8.0 Hz), 6.84 (1H, d, J=8.0 Hz), 6.73 (1H, d, J=15.5 Hz), 6.02 (2H, s), 4.21 (2H, q, J=6.9 Hz), 4.09 (2H, q, J=6.9 Hz), 4.04 (3H, s), 1.38 (3H, t, J=6.9 Hz), 1.26 (3H, t, J=6.9 Hz).

EXAMPLE 23

(E)-8-[2-(1,4-Benzodioxan-6-yl)vinyl]-1,3-diethylxanthine (Compound 80)

Substantially the same procedure as in Example 7 was repeated using 2.85 g (14.4 mmol) of 5,6-diamino-1,3diethyluracil and 2.70 g (13.1 mmol) of 3-(1,4-benzodioxan-6-yl)acrylic acid. Then, the resultant crude crystals were recrystallized from dioxane/water to give 2.45 g (yield 51%) of Compound 80 as a pale yellow powder.

Melting Point: >300° C.; Elemental Analysis: $C_{19}H_{20}N_4O_4$, Calcd. (%): C, 61.94; H, 5.47; N, 15.20; Found (%): C, 61.97; H, 5.62; N, 15.07; IR (KBr) $v_{max}$ (cm$^{-1}$): 1682, 1637, 1511, 1310; NMR (270 MHz; DMSO-$d_6$)δ(ppm): 7.51(1H, d, J=16.2 Hz), 7.10–7.03(2H, m), 6.89(1H, d, J=7.9 Hz), 6.87(1H, d, J=16.2 Hz), 4.27(4H, s), 4.05(2H, q, J=6.9 Hz), 3.93(2H, q, J=6.9 Hz), 1.22(3H, t, J=6.9 Hz), 1.13 (3H, t, J=6.9 Hz).

EXAMPLE 24

(E)-8-[2-(1,4-Benzodioxan-6-yl) vinyl]-1,3-diethyl-7-methylxanthine (Compound 81)

Substantially the same procedure as in Example 8 was repeated using 2.00 g (5.43 mmol) of Compound 80 obtained in Example 23 in place of Compound 64. Then, the resultant crude crystals were recrystallized from ethanol/isopropanol to give 1.58 g (yield 76%) of Compound 81 as yellow needles.

Melting Point: 233.1°–233.6° C.; Elemental Analysis: $C_{20}H_{22}N_4O_4$, Calcd. (%): C, 62.81; H, 5.79; N, 14.65; Found (%): C, 62.55; H, 5.80; N, 14.60; IR (KBr) $v_{max}$ (cm$^{-1}$): 1689, 1654, 1509; NMR (270 MHz; CDCl$_3$)δ(ppm): 7.67(1H, d, J=15.8 Hz), 7.15–7.05(2H, m), 6.88(1H, d, J=8.3 Hz), 6.75(1H, d, J=15.8 Hz), 4.30 (4H, s), 4.21 (2H, q, J=6.9 Hz), 4.08 (2H, q, J=6.9 Hz), 4.03 (3H, s), 1.39 (3H, t, J=6.9 Hz), 1.35 (3H, t, J=6.9 Hz).

EXAMPLE 25

(E)-8-(2,3,4-Trimethoxystyryl)theophylline (Compound 82)

Substantially the same procedure as in Example 7 was repeated using 5.00 g (29.4 mmol) of 5,6-diamino-1,3-dimethyluracil and 7.71 g (32.4 mmol) of 2,3,4-trimethoxycinnamic acid. Then, the resultant crude crystals were recrystallized from isopropanol/water to give 3.78 g (yield 35%) of Compound 82 as an ocher powder.

Melting Point: 264.8°–266.1° C.; Elemental Analysis: $C_{18}H_{20}N_4O_5$, Calcd. (%): C, 58.05; H, 5.41; N, 15.04; Found (%): C, 58.28; H, 5.38; N, 15.20; IR (KBr) $v_{max}$ (cm$^{-1}$): 1697, 1651, 1505, 1297; NMR (270 MHz; CDCl$_3$)δ(ppm): 12.78(1H, s), 7.91(1H, d, J=16.8 Hz), 7.28(1H, d, J=9.4 Hz), 7.13(1H, d, J=16.8 Hz), 6.73(1H, d, J=9.4 Hz), 3.95(3H, s), 3.92 (3H, s), 3.90(3H, s), 3.69(3H, s), 3.54(3H, s).

EXAMPLE 26

(E)-8-(2,3, 4-Trimethoxystyryl) caffeine (Compound 83)

Substantially the same procedure as in Example 8 was repeated using 2.00 g (5.38 mmol) of Compound 82 obtained in Example 25 in place of Compound 64. Then, the resultant crude crystals were recrystallized from cyclohexane/toluene to give 1.68 g (yield 81%) of Compound 83 as a pale yellow powder.

Melting Point: 186.7°–187.9° C.; Elemental Analysis: $C_{19}H_{22}N_4O_5$, Calcd. (%): C, 59.06; H, 5.74; N, 14.50; Found (%): C, 59.27; H, 5.72; N, 14.60; IR (KBr) $v_{max}$ (cm$^{-1}$): 1694, 1655, 1596, 1544, 1501, 1295; NMR (270 MHz; CDCl$_3$)δ(ppm): 7.90 (1H, d, J=16.3 Hz), 7.28(1H, d, J=7.9 Hz), 7.01(1H, d, J=16.3 Hz), 6.72 (1H, d, J=7.9 Hz), 4.04 (3H, s), 3.97 (3H, s), 3.91 (3H, s), 3.90 (3H, s), 3.64 (3H, s), 3.42 (3H, s).

EXAMPLE 27

(E)-8-(4-Methoxy-2,3-dimethylstyryl)theophylline (Compound 84)

Substantially the same procedure as in Example 7 was repeated using 1.74 g (10.2 mmol) of 5,6-diamino-1,3-dimethyluracil and 2.42 g (11.8 mmol) of 4-methoxy-2, 3dimethylcinnamic acid. Then, the resultant crude crystals were recrystallized from acetonitrile to give 750 mg (yield 22%) of Compound 84 as a white powder.

Melting Point: >275° C.; Elemental Analysis: $C_{18}H_{20}N_4O_3$, Calcd. (%): C, 63.51; H, 5.92; N, 16.46; Found (%): C, 63.56; H, 5.82; N, 16.30; IR (KBr) $v_{max}$ (cm$^{-1}$): 1703, 1634, 1593; NMR (270 MHz; DMSO-d$_6$)δ(ppm): 13.45(1H, s), 7.93(1H, d, J=16.2 Hz), 7.53(1H, d, J=8.9 Hz), 6.88(1H, d, J=8.9 Hz), 6.79(1H, d, J=16.2 Hz), 3.80(3H, s), 3.75 (3H, s), 3.25(3H, s), 2.32(3H, s), 2.12(3H, s).

EXAMPLE 28

(E)-8-(4-Methoxy-2,3-dimethylstyryl)caffeine (Compound 85)

Substantially the same procedure as in Example 8 was repeated using 500 mg (1.47 mmol) of Compound 84 obtained in Example 27 in place of Compound 64. Then, the resultant crude crystals were recrystallized from toluene to give 280 mg (yield 54%) of Compound 85 as a pale yellow powder.

Melting Point: >275° C.; Elemental Analysis: $C_{19}H_{22}N_4O_3$, Calcd. (%): C, 64.39; H, 6.25; N, 15.80; Found (%): C, 64.44; H, 6.27; N, 16.11; IR (KBr) $v_{max}$ (cm$^{-1}$): 1694, 1650, 1544, 1491, 1435; NMR (270 MHz; CDCl$_3$)δ(ppm): 7.96(1H, d, J=15.5 Hz), 7.73 (1H, d, J=8.6 Hz), 7.07 (1H, d, J=15.5 Hz), 6.90 (1H, d, J=S.6Hz), 4.02(3H, s), 3.82(3H, s), 3.48 (3H, s), 3.29(3H, s), 2.32(3H, s), 2.13(3H, s).

EXAMPLE 29

(E)-8-(3,4-Methylenedioxystyryl)theophylline (Compound 86)

Substantially the same procedure as in Example 7 was repeated using 5.0 g (29.4 mmol) of 5,6-diamino-1,3 -dimethyluracil and 6.78 g (35.3 mmol) of 3,4-methylenedioxycinnamic acid. Then, the resultant crude crystals were recrystallized from dimethylformamide/water to give 1.20 g (yield 13%) of Compound 86 as a pale yellow powder.

Melting Point: >275° C.; Elemental Analysis: $C16H14N_4O_4$, Calcd. (%): C, 58.99; H, 4.32; N, 17.16; Found (%): C, 58.84; H, 4.30; N, 16.97; IR (KBr) $v_{max}$ (cm$^{-1}$): 1692, 1642, 1499; NMR (270 MHz; DMSO-d$_6$)δ(ppm): 7.57(1H, d, J=16.1 Hz), 7.09(1H, s), 7.07(1H, d, J=7.9 Hz), 6.92(1H, d, J=7.9 Hz), 6.88(1H, d, J=16.1 Hz), 6.07(2H, s), 3.47 (3H, s), 3.30(3H, s).

EXAMPLE 30

(E)-8-(3,4-Methylenedioxystyryl)caffeine (Compound 87)

Substantially the same procedure as in Example 8 was repeated using 2.32 g (7.13 mmol) of Compound 86 obtained in Example 29 in place of Compound 64. Then, the resultant crude crystals were recrystallized from dioxane to give 1.54 g (yield 64%) of Compound 87 as yellow needles.

Melting Point: >300° C.; Elemental Analysis: $C17H16N_4O_4$, Calcd. (%): C, 59.99; H, 4.73; N, 16.46; Found (%): C, 59.98; H, 4.66; N, 16.38; IR (KBr) $v_{max}$ (cm$^{-1}$): 1702, 1663, 1545, 1506; NMR (270 MHz; CDCl$_3$)δ(ppm): 7.72(1H, d, J=15.3 Hz), 7.10(1H, d, J=1.5 Hz), 7.06(1H, dd, J=1.5, 7.9 Hz), 6.84(1H, d, J=7.9Hz), 6.73(1H, d, J=15.3 Hz), 6.03 (2H, s), 4.05(3H, s), 3.63(3H, s), 3.42(3H, s).

EXAMPLE 31

(E)-8-(2,3-Dimethoxystyryl)theophylline (Compound 88)

Substantially the same procedure as in Example 7 was repeated using 2.50 g (14.7 mmol) of 5,6-diamino-1,3-dimethyluracil and 3.37 g (16.2 mmol) of 2,3-dimethoxycinnamic acid. Then, the resultant crude crystals were recrystallized from ethanol/water to give 1.03 g (yield of Compound 88 as pale yellow needles.

Melting Point: 289.2°–290.5° C.; Elemental Analysis: $C_{17}H_{18}N_4O_4$, Calcd. (%): C, 59.64; H, 5.29; N, 16.36; Found (%): C, 59.42; H, 5.12; N, 16.65; IR (KBr) $v_{max}$ (cm$^{-1}$): 1700, 1649, 1499, 1476, 1273; NMR (270 MHz; DMSO-d$_6$)δ(ppm): 13.60(1H, brs), 7.84 (1H, d, J=16.8 Hz), 7.26(1H, d, J=6.9 Hz), 7.15–7.00 (3H, m), 3.83(3H, s), 3.79(3H, s), 3.48(3H, s), 3.26 (3H, s).

EXAMPLE 32

(E)-8-(2,3-Dimethoxystyryl)caffeine (Compound 89)

Substantially the same procedure as in Example 8 was repeated using 1.10 g (3.22 mmol) of Compound 88 obtained in Example 31 in place of Compound 64. Then, the resultant crude crystals were recrystallized from toluene to give 570 mg (yield 50%) of Compound 89 as yellow needles.

Melting Point: 233.6°–236.7° C.; Elemental Analysis: $C_{18}H_{20}N_4O_4$, Calcd. (%): C, 60.66; H, 5.65; N, 15.72; Found (%): C, 60.21; H, 5.74; N, 16.13; IR (KBr) $v_{max}$ (cm$^{-1}$): 1688, 1645, 1545, 1480; NMR (270 MHz; DMSO-d$_6$)δ(ppm): 7.91(1H, d, J=16.0 Hz), 7.52 (1H, dd, J=1.7, 7.6 Hz), 7.32 (1H, d, J=16.0 Hz), 7.10–7.05(2H, m), 4.03(3H, s), 3.84 (3H, s), 3.79 (3H, s), 3.48 (3H, s), 3.24(3H, s).

EXAMPLE 33

(E)-8-(2,4-Dimethoxystyryl)theophylline (Compound 90)

Substantially the same procedure as in Example 7 was repeated using 1.0 g (5.88 mmol) of 5,6-diamino-1,3-dimethyluracil and 1.35 g (6.48 mmol) of 2,4-dimethoxycinnamic acid. Then, the resultant crude crystals were recrystallized from dimethylformamide to give 221 mg (yield 11%) of Compound 90 as pale yellow grains.

Melting Point: >280° C.; Elemental Analysis: $C_{17}H_{18}N_4O_4$, Calcd. (%): C, 59.64; H, 5.29; N, 16.36; Found (%): C, 59.51; H, 5.34; N, 16.58; IR (KBr) $v_{max}$ (cm$^{-1}$): 1705, 1650, 1607, 1505; NMR (270 MHz; DMSO-$d_6$)$\delta$(ppm): 13.40(1H, brs), 7.78 (1H, d, J=16.5 Hz), 7.53(1H, d, J=8.3 Hz), 6.93(1H, d, J=16.5 Hz), 6.63(1H, d, J=2.3 Hz), 6.60(1H, dd, J=2.3, 8.3 Hz), 3.89(3H, s), 3.82(3H, s), 3.47(3H, s), 3.25(3H, s).

EXAMPLE 34

(E)-8-(2,4-Dimethoxystyryl)caffeine (Compound 91)

Substantially the same procedure as in Example 8 was repeated using 700 mg (2.05 mmol) of Compound 90 obtained in Example 33 in place of Compound 64. Then, the resultant crude crystals were recrystallized from dioxane to give 621 mg (yield 85%) of Compound 91 as yellow needles.

Melting Point: 241.5°–242.1° C.; Elemental Analysis: $C_{18}H_{20}N_4O_4$, Calcd. (%): C, 60.66; H, 5.65; N, 15.72; Found (%): C, 60.49; H, 5.61; N, 15.69; IR (KBr) $v_{max}$ (cm$^{-1}$): 1685, 1650, 1602, 1434; NMR (270 MHz; CDCl$_3$)$\delta$(ppm): 7.95(1H, d, J=15.8 Hz), 7.48(1H, d, J=8.6 Hz), 6.98(1H, d, J=15.5 Hz), 6.54 (1H, dd, J=2.3, 8.6 Hz), 6.49(1H, d, J=2.3 Hz), 4.03 (3H, s), 3.92(3H, s), 3.86(3H, s), 3.64(3H, s), 3.42 (3H, s).

EXAMPLE 35

(E)-8-(4-Methoxy-2,5-dimethylstyryl)theophylline (Compound 92)

Substantially the same procedure as in Example 7 was repeated using 1.0 g (5.88 mmol) of 5,6-diamino-1,3-dimethyluracil and 1.33 g (6.45 mmol) of 4-methoxy-2,5-dimethylcinnamic acid. Then, the resultant crude crystals were recrystallized from dimethylformamide to give 393 mg (yield 20%) of Compound 92 as pale yellow grains.

Melting Point: >280° C.; Elemental Analysis: $C_{18}H_{20}N_4O_3$, Calcd. (%): C, 63.51; H, 5.92; N, 16.46; Found (%): C, 63.59; H, 6.10; N, 16.23; IR (KBr) $v_{max}$ (cm$^{-1}$): 1703, 1648, 1509, 1260; NMR (270 MHz; DMSO-$d_6$)$\delta$(ppm): 13.48(1H, brs), 7.81 (1H, d, J=16.2 Hz), 7.50(1H, s), 6.82(1H, d, J=16.2 Hz), 6.81(1H, s), 3.81(3H, s), 3.46(3H, s), 3.25(3H, s), 2.40(3H, s), 2.14(3H, s).

EXAMPLE 36

(E)-8-(4-Methoxy-2,5-dimethylstyryl)caffeine (Compound 93)

Substantially the same procedure as in Example 8 was repeated using 300 mg (0.88 mmol) of Compound 92 obtained in Example 35 in place of Compound 64. Then, the resultant crude crystals were recrystallized from dioxane to give 211 mg (yield 68%) of Compound 93 as yellow needles.

Melting Point: >280° C.; MS-EI m/e: 354 (M$^+$), 339 (M+-CH$_3$); IR (KBr) $v_{max}$ (cm$^{-1}$): 1692, 1653, 1508; NMR (270 MHz; CDCl$_3$)$\delta$(ppm): 8.00(1H, d, J=15.3 Hz), 7.42(1H, s), 6.72(1H, d, J=15.3 Hz), 6.66(1H, s), 4.06(3H, s), 3.86(3H, s), 3.64(3H, s), 3.42(3H, s), 2.49 (3H, s), 2.23 (3H, s).

EXAMPLE 37

(E)-8-(2,4-Dimethoxy-3-methylstyryl)theophylline (Compound 94)

Substantially the same procedure as in Example 7 was repeated using 1.0 g (5.88 mmol) of 5,6-diamino-1,3dimethyluracil and 1.44 g (6.45 mmol) of 2,4-dimethoxy-3methylcinnamic acid. Then, the resultant crude crystals were recrystallized from dioxane to give 581 mg (yield 28%) of Compound 94 as pale yellow needles.

Melting Point: >280° C.; Elemental Analysis: $C_{18}H_{20}N_4O_4$, Calcd. (%): C, 60.67; H, 5.65; N, 15.72; Found (%): C, 60.34; H, 5.77; N, 15.64; IR (KBr) $v_{max}$ (cm$^{-1}$): 1695, 1653, 1499, 1270; NMR (270 MHz; DMSO-$d_6$)$\delta$(ppm): 13.52(1H, brs), 7.75 (1H, d, J=16.2 Hz), 7.55(1H, d, J=8.3 Hz), 6.96(1H, d, J=16.2 Hz), 6.84(1H, d, J=8.3 Hz), 3.83(3H, s), 3.70 (3H, s), 3.47(3H, s), 3.25(3H, s), 2.09(3H, s).

EXAMPLE 38

(E)-8-(2,4-Dimethoxy-3-methylstyryl)caffeine (Compound 95)

Substantially the same procedure as in Example 8 was repeated using 300 mg (0.84 mmol) of Compound 94 obtained in Example 37 in place of Compound 64. Then, the resultant crude crystals were recrystallized from methylene chloride/diethyl ether to give 239 mg (yield 77%) of Compound 95 as white needles.

Melting Point: 252.7°–253.5° C.; Elemental Analysis: $C_{19}H_{22}N_4O_4$, Calcd. (%): C, 61.61; H, 5.98; N, 15.13; Found (%): C, 61.40; H, 6.06; N, 15.17; IR (KBr) $v_{max}$ (cm$^{-1}$): 1692, 1651, 1505; NMR (270 MHz; CDCl$_3$)$\delta$(ppm): 7.92(1H, d, J=15.8 Hz), 7.42(1H, d, J=8.9 Hz), 6.99(1H, d, J=15.8 Hz), 6.70 (1H, d, J=8.9 Hz), 4.04 (3H, s), 3.88 (3H, s), 3.78 (3H, s), 3.64 (3H, s), 3.42 (3H, s), 2.19(3H, s)

EXAMPLE 39

(E)-8-(2,5-Dimethylstyryl)-1,3-diethylxanthine (Compound 96)

Substantially the same procedure as in Example 7 was repeated using 3.00 g (15.1 mmol) of 5,6-diamino-1,3-diethyluracil and 3.20 g (18.2 mmol) of 2,5-dimethylcinnamic acid. Then, the resultant crude crystals were recrystallized from ethanol/toluene to give 2.56 g (yield of Compound 96 as white needles.

Melting Point: 281.8°–282.5° C.; Elemental Analysis: $C_{19}H_{22}N_4O_2 \cdot 0.5H_2O$, Calcd. (%): C, 66.46; H, 6.97; N, 15.50; Found (%): C, 66.77; H, 6.82; N, 15.72; IR (KBr) $v_{max}$ (cm$^{-1}$): 1706, 1639, 1503; NMR (270 MHz; DMSO-$d_6$)$\delta$(ppm): 7.84(1H, d, J=16.3 Hz), 7.53(1H, s), 7.13(1H, d, J=7.4 Hz), 7.06(1H, d, J=7.4 Hz), 7.00(1H, d, J=16.3 Hz), 4.06 (2H, q, J=7.1 Hz), 3.94 (2H, q, J=7.1 Hz), 2.37 (3H, s), 2.30 (3H, s), 1.26(3H, t, J=7.1 Hz), 1.14 (3H, t, J=7.1 Hz).

EXAMPLE 40

(E)-8-(2, 5-Dimethylstyryl)-1,3-diethyl-7-methylxanthine (Compound 97)

Substantially the same procedure as in Example 8 was repeated using 2.00 g (5.92 mmol) of Compound 96 obtained in Example 39 in place of Compound 64. Then, the resultant crude crystals were recrystallized from toluene/cyclohexane to give 1.29 g (yield 62%) of Compound as white needles.

Melting Point: 190.3°–190.7° C.; Elemental Analysis: $C_{20}H_{24}N_4O_2$, Calcd. (%): C, 68.16; H, 6.86; N, 15.89; Found (%): C, 68.15; H, 7.02; N, 15.65; IR (KBr) $v_{max}$ (cm$^{-1}$): 1698, 1657; NMR (270 MHz; CDCl$_3$)δ(ppm): 7.86 (1H, d, J=15.8 Hz), 7.71(1H, s), 7.23(1H, d, J=15.8 Hz), 7.15 (1H, d, J=7.9 Hz), 7.09 (1H, d, J=7.9 Hz), 4.11–4.04 (2H, m), 4.04 (3H, s), 3.92 (2H, q, J=6.9 Hz), 2.37(3H, s), 2.32(3H, s), 1.26(3H, t, J=6.9 Hz), 1.13 (3H, t, J=6.9 Hz).

EXAMPLE 41

(E)-8-(4-Ethoxystyryl)-1,3-diethylxanthine (Compound 98)

Substantially the same procedure as in Example 7 was repeated using 3.00 g (15.1 mmol) of 5,6-diamino-1,3-diethyluracil and 3.20 g (16.7 mmol) of 4-ethoxycinnamic acid. Then, the resultant crude crystals were recrystallized from dioxane to give 2.97 g (yield 55%) of Compound 98 as pale yellow needles.

Melting Point: 296.7°–298.6° C.; Elemental Analysis: $C_{19}H_{22}N_4O_3$, Calcd. (%): C, 64.39; H, 6.25; N, 15.81; Found (%): C, 64.54; H, 6.52; N, 15.80; IR (KBr) $v_{max}$ (cm$^{-1}$): 1695, 1647, 1516, 1250; NMR (270 MHz; DMSO-d$_6$)δ(ppm): 13.36 (1H, brs), 7.59 (1H, d, J=16.2 Hz), 7.55 (2H, d, J=8.6 Hz), 6.96 (2H, d, J=8.6 Hz), 6.88(1H, d, J=16.2 Hz), 4.11–4.04(4H, m), 3.94 (2H, q, J=6.9 Hz), 1.34(3H, t, J=6.9 Hz), 1.26 (3H, t, J=6.9 Hz), 1.14 (3H, t, J=6.9 Hz).

EXAMPLE 42

(E)-8-(4-Ethoxystyryl)-1,3-diethyl-7-methylxanthine (Compound 99)

Substantially the same procedure as in Example 8 was repeated using 1.60 g (4.52 mmol) of Compound 98 obtained in Example 41 in place of Compound 64. Then, the resultant crude crystals were recrystallized from ethyl acetate to give 1.47 g (yield 88%) of Compound 99 as pale green needles.

Melting Point: 185.3°–185.7° C.; Elemental Analysis: $C_{20}H_{24}N_4O_3$, Calcd. (%): C, 65.20; H, 6.56; N, 15.21; Found (%): C, 65.28; H, 6.85; N, 15.18; IR (KBr) $v_{max}$ (cm$^{-1}$): 1693, 1666, 1515, 1248; NMR (270 MHz; CDCl$_3$)δ(ppm): 7.74 (1H, d, J=15.8 Hz), 7.52 (2H, d, J=8.6 Hz), 6.92 (2H, d, J=8.6 Hz), 6.77 (1H, d, J=15.8 Hz), 4.21(2H, q, J=6.9 Hz), 4.12–4.01 (4H, m), 4.04 (3H, s), 1.44 (3H, t, J=6.9 Hz), 1.38 (3H, t, J=7.6 Hz), 1.26 (3H, t, J=6.9 Hz).

EXAMPLE 43

(E)-1,3-Diethyl-8-(4-propoxystyryl)xanthine (Compound 100)

Substantially the same procedure as in Example 7 was repeated using 3.00 g (15.1 mmol) of 5,6-diamino-1,3-diethyluracil and 3.43 g (16.6 mmol) of 4-propoxycinnamic acid. Then, the resultant crude crystals were recrystallized from dioxane/water to give 3.02 g (yield 54%) of Compound 100 as pale yellow needles.

Melting Point: >270° C.; Elemental Analysis: $C_{20}H_{24}N_4O_3$, Calcd. (%): C, 65.20; H, 6.56; N, 15.21; Found (%): C, 64.91; H, 6.79; N, 15.14; IR (KBr) $v_{max}$ (cm$^{-1}$): 1695, 1656, 1515, 1250 NMR (270 MHz; DMSO-d$_6$)δ(ppm): 13.38(1H, brs), 7.59 (1H, d, J=16.5 Hz), 7.55 (2H, d, J=8.6Hz), 6.97 (2H, d, J=8.6 Hz), 6.87 (1H, d, J=16.5 Hz), 4.07 (2H, q, J=7.3 Hz), 4.00–3.90(4H, m), 1.81–1.67 (2H, m), 1.26 (3H, t, J=6.9 Hz), 1.14 (3H, t, J=6.9 Hz), 0.98 (3H, t, J=7.3 Hz).

EXAMPLE 44

(E)-1,3-Diethyl-7-methyl-8-(4-propoxystyryl)xanthine (Compound 101)

Substantially the same procedure as in Example 8 was repeated using 1.70 g (4.61 mmol) of Compound 100 obtained in Example 43 in place of Compound 64. Then, the resultant crude crystals were recrystallized from hexane/ethyl acetate to give 1.37 g (yield 78%) of Compound 101 as pale yellow needles.

Melting Point: 155.7°–156.5° C.; Elemental Analysis: $C_{21}H_{26}N_4O_3$, Calcd. (%): C, 65.92; H, 6.85; N, 14.65; Found (%): C, 65.72; H, 7.05; N, 14.59; IR (KBr) $v_{max}$ (cm$^{-1}$): 1696, 1665, 1513, 1246; NMR (270 MHz; CDCl$_3$)δ(ppm): 7.74(1H, d, J=15.8 Hz), 7.52 (2H, d, J=8.6Hz), 6.92 (2H, d, J=8.6 Hz), 6.77 (1H, d, J=15.8 Hz), 4.21(2H, q, J=6.9 Hz), 4.09(2H, q, J=6.9 Hz), 4.04 (3H, s), 3.97 (2H, t, J=6.6 Hz), 1.90–1.77 (2H, m), 1.38 (3H, t, J=6.9 Hz), 1.26 (3H, t, J=6.9 Hz), 1.05(3H, t, J=7.3 Hz).

EXAMPLE 45

(E)-1,3-Diethyl-8-(3-methoxystyryl)xanthine (Compound 102)

Substantially the same procedure as in Example 7 was repeated using 2.50 g (12.6 mmol) of 5,6-diamino-1,3-diethyluracil and 2.48 g (13.9 mmol) of 3-methoxycinnamic acid. Then, the resultant crude crystals were recrystallized from dimethylformamide/water to give 2.10 g (yield 49%) of Compound 102 as a white powder.

Melting Point: 270.6°–272.5° C.; Elemental Analysis: $C_{18}H_{20}N_4O_3$, Calcd. (%): C, 63.52; H, 5.92; N, 16.46; Found (%): C, 63.20; H, 6.01; N, 16.34; IR (KBr) $v_{max}$ (cm$^{-1}$): 1686, 1634, 1500; NMR (270 MHz; DMSO-d$_6$)δ(ppm): 7.61(1H, d, J=16.4 Hz), 7.34(1H, t, J=7.9 Hz), 7.20–7.18(2H, m), 7.07(1H, d, J=16.4 Hz), 6.92(1H, d, J=8.6 Hz), 4.06(2H, q, J=7.0 Hz), 3.94(2H, q, J=6.8 Hz), 1.26(3H, t, J=7.0 Hz), 1.14 (3H, t, J=6.8 Hz).

EXAMPLE 46

(E)-1,3-Diethyl-8-(3-methoxystyryl)-7-methylxanthine (Compound 103)

Substantially the same procedure as in Example 8 was repeated using 1.70 g (5.00 mmol) of Compound 102 obtained in Example 45 in place of Compound 64. Then, the resultant crude crystals were recrystallized from toluene/cyclohexane to give 1.10 g (yield 62%) of Compound 103 as pale yellow needles.

Melting Point: 153.4°–154.8° C.; Elemental Analysis: $C_{19}H_{22}N_4O_3$, Calcd. (%): C, 64.39; H, 6.26; N, 15.81; Found (%): C, 64.34; H, 6.38; N, 15.82; IR (KBr) $v_{max}$ (cm$^{-1}$): 1692, 1656, 1541; NMR (270 MHz; DMSO-d$_6$)δ(ppm): 7.64 (1H, d, J=15.8 Hz), 7.40–7.30(4H, m), 6.97–6.92(1H, m), 4.31–4.05(2H, m), 4.05(3H, s), 3.92(2H, q, J=7.0 Hz), 1.26(3H, t, J=7.1 Hz), 1.13(3H, t, J=7.0 Hz).

EXAMPLE 47

(E)-8-(4-Butoxystyryl)-1,3-diethylxanthine
(Compound 104)

Substantially the same procedure as in Example 7 was repeated using 3.00 g (15.1 mmol) of 5,6-diamino-1,3-diethyluracil and 3.67 g (16.7 mmol) of 4-butoxycinnamic acid. Then, the resultant crude crystals were recrystallized from dioxane/water to give 3.04 g (yield 53%) of Compound 104 as pale yellow needles.

Melting Point: 257.9°–261.3° C.; Elemental Analysis: C$_{21}$H$_{26}$N$_4$O$_3$, Calcd. (%): C, 65.95; H, 6.85; N, 14.65; Found (%): C, 65.90; H, 7.21; N, 14.60; IR (KBr) ν$_{max}$ (cm$^{-1}$): 1695, 1645, 1515, 1248; NMR (270 MHz; DMSO-d$_6$)δ(ppm): 13.32 (1H, brs), 7.59 (1H, d, J=b 16.5Hz), 7.55 (2H, d, J=8.9 Hz), 6.97 (2H, d, J=8.9 Hz), 6.87 (1H, d, J=16.5 Hz), 4.10–3.90(6H, m), 1.76–1.66(2H, m), 1.51–1.40(2H, m), 1.26(3H, t, J=6.9 Hz), 1.14 (3H, t, J=6.9Hz), 0.94 (3H, t, J=7.3 Hz).

EXAMPLE 48

(E)-8-(4-Butoxystyryl)-1,3-diethyl-7-methylxanthine
(Compound 105)

Substantially the same procedure as in Example 8 was repeated using 1.50 g (3.92 mmol) of Compound 104 obtained in Example 47 in place of Compound 64. Then, the resultant crude crystals were recrystallized from hexane/ethyl acetate to give 982 mg (yield 63%) of Compound 105 as pale yellow needles.

Melting Point: 123.4°–123.6° C.; Elemental Analysis: C$_{22}$H$_{28}$N$_4$O$_3$, Calcd. (%): C, 66.65; H, 7.11; N, 14.13; Found (%): C, 66.81; H, 7.31; N, 14.01; IR (KBr) ν$_{max}$ (cm$^{-1}$): 1693, 1665, 1513, 1251; NMR (270 MHz; CDCl$_3$)δ(ppm): 7.74(1H, d, J=15.8 Hz), 7.52 (2H, d, J=8.9 Hz), 6.92 (2H, d, J=8.9 Hz), 6.76 (1H, d, J=15.8 Hz), 4.21(2H, q, J=6.9 Hz), 4.09(2H, q, J=6.9 Hz), 4.04(3H, s), 4.02(2H, q, J=6.6 Hz), 1.84–1.74(2H, m), 1.58–1.44(2H, m), 1.38(3H, t, J=6.9 Hz), 1.26 (3H, t, J=6.9 Hz), 0.99 (3H, t, J=7.3 Hz).

EXAMPLE 49

(E)-1,3-Diethyl-8-(4-methylstyryl)xanthine
(Compound 106)

Substantially the same procedure as in Example 7 was repeated using 3.00 g (15.1 mmol) of 5,6-diamino-1,3-diethyluracil and 2.70 g (16.7 mmol) of 4-methylcinnamic acid. Then, the resultant crude crystals were recrystallized from dioxane to give 2.64 g (yield 54%) of Compound 106 as pale yellow needles.

Melting Point: >280° C.; Elemental Analysis: C$_{18}$H$_{20}$N$_4$O$_2$, Calcd. (%): C, 66.65; H, 6.21; N, 17.27; Found (%): C, 66.53; H, 6.27; N, 17.14; IR (KBr) ν$_{max}$ (cm$^{-1}$): 1692, 1644, 1518, 1490; NMR (270 MHz; DMSO-d$_6$)δ(ppm): 13.53 (1H, brs), 7.62 (1H, d, J=16.5 Hz), 7.52(2H, d, J=7.9 Hz), 7.24(2H, d, J=7.9 Hz), 6.98(1H, d, J=16.5 Hz), 4.07(2H, q, J=6.9 Hz), 3.94 (2H, q, J=6.9 Hz), 2.33 (3H, s), 1.26 (3H, t, J=6.9 Hz), 1.14(3H, t, J=6.9 Hz).

EXAMPLE 50

(E)-1,3-Diethyl-7-methyl-8-(4-methylstyryl)xanthine
(Compound 107)

Substantially the same procedure as in Example 8 was repeated using 1.50 g (4.62 mmol) of Compound 106 obtained in Example 49 in place of Compound 64. Then, the resultant crude crystals were recrystallized from dioxane/water to give 1.39 g (yield 89%) of Compound 107 as yellow needles.

Melting Point: 170.8°–171.5° C.; Elemental Analysis: C$_{19}$H$_{22}$N$_4$O$_2$, Calcd. (%): C, 67.44; H, 6.55; N, 16.56; Found (%): C, 67.58; H, 6.65; N, 16.68; IR (KBr) ν$_{max}$ (cm$^{-1}$): 1687, 1650, 1542, 1516; NMR (270 MHz; CDCl$_3$)δ(ppm): 7.77(1H, d, J=15.8 Hz), 7.48(2H, d, J=8.3 Hz), 7.21(2H, d, J=8.3 Hz), 6.87 (1H, d, J=15.8 Hz), 4.22(2H, q, J=6.9 Hz), 4.09(2H, q, J=6.9 Hz), 4.05(3H, s), 2.39(3H, s), 1.38(3H, t, J=6.9 Hz), 1.26 (3H, t, J=6.9 Hz).

EXAMPLE 51

(E)-1,3-Diethyl-8-(2-methoxystyryl)xanthine
(Compound 108)

Substantially the same procedure as in Example 7 was repeated using 2.5 g (12.6 mmol) of 5,6-diamino-1,3-diethyluracil and 2.48 g (13.9 mmol) of 2-methoxycinnamic acid. Then, the resultant crude crystals were recrystallized from tetrahydrofuran/water to give 990 mg (yield 24%) of Compound 108 as yellow grains.

Melting Point: >270° C.; Elemental Analysis: C$_{18}$H$_{20}$N$_4$O$_3$, Calcd. (%): C, 63.52; H, 5.92; N, 16.46; Found (%): C, 63.28; H, 5.86; N, 16.43; IR (KBr) ν$_{max}$ (cm$^{-1}$): 1694, 1640, 1501; NMR (270 MHz; DMSO-d$_6$)δ(ppm): 7.85 (1H, d, J=16.8 Hz), 7.62 (1H, d, J=7.6 Hz), 7.34 (1H, t, J=7.6 Hz), 7.11– 6.98(3H, m), 4.07(2H, q, J=7.0 Hz), 3.97–3.89(2H, m), 3.89(3H, s), 1.26(3H, t, J=7.0 Hz), 1.14(3H, t, J=6.9Hz).

EXAMPLE 52

(E)-1,3-Diethyl-8-(2-methoxystyryl)-7-methylxanthine
(Compound 109)

Substantially the same procedure as in Example 8 was repeated using 1.5 g (4.41 mmol) of Compound 108 obtained in Example 51 in place of Compound 64. Then, the resultant crude crystals were recrystallized from ethanol/water to give 800 mg (yield 51%) of Compound 109 as yellow needles.

Melting Point: 189.6°–190.0° C.; Elemental Analysis: C$_{19}$H$_{22}$N$_4$O$_3$, Calcd. (%): C, 64.39; H, 6.26; N, 15.81; Found (%): C, 64.18; H, 6.25; N, 15.77; IR (KBr) ν$_{max}$ ($^{cm-1}$): 1697, 1649; NMR (270 MHz; DMSO-d$_6$)δ(ppm): 7.94 (1H, d, J=15.8 Hz), 7.88 (1H, dd, J=7.9, 1.5 Hz), 7.41–7.34 (1H, m), 7.31 (1H, d, J=15.8 Hz), 7.10 (1H, d, J=7.9 Hz), 7.02 (1H, t, J=7.4 Hz), 4.11–4.02 (2H, m), 4.02(3H, s), 3.96t, 3.90 (2H, m), 3.90(3H, s), 1.29(3H, t, J=7.2 Hz), 1.13 (3H, t, J=7.2 Hz).

EXAMPLE 53

(E)-1,3-Diethyl-8-(4-methoxy-3-methylstyryl)xanthine
(Compound 110)

Substantially the same procedure as in Example 7 was repeated using 2.50 g (12.6 mmol) of 5,6-diamino-1,3-diethyluracil and 3.00 g (13.9 mmol) of 4-methoxy-3- methylcinnamic acid. Then, the resultant crude crystals were recrystallized from dimethylsulfoxide/water to give 1.70 g (yield 36%) of Compound 110 as white flocculent precipitates.

Melting Point: >270° C.; Elemental Analysis: $C_{19}H_{22}N_4O_3$, Calcd. (%): C, 64.39; H, 6.23; N, 15.81; Found (%): C, 64.05; H, 6.34; N, 15.74; IR (KBr) $v_{max}$ ($cm^{-1}$): 1689, 1644, 1510, 1459; NMR (270 MHz; DMSO-$d_6$)δ(ppm): 7.56(1H, d, J=16.3 Hz), 7.45(1H, s), 7.44(1H, d, J=8.2 Hz), 6.98(1H, d, J=8.2 Hz), 6.87 (1H, d, J=t6.3 Hz), 4.06 (2H, q, J=7.1 Hz), 3.93(2H, q, J=7.0 Hz), 3.82(3H, s), 2.18 (3H, s), 1.25 (3H, t, J=7.1 Hz), 1.13 (3H, t, J=7.0 Hz).

EXAMPLE 54

(E)-1,3-Diethyl-8-(4-methoxy-3-methylstyryl)-7-methylxanthine (Compound 111)

Substantially the same procedure as in Example 8 was repeated using 1.27 g (3.36 mmol) of Compound 110 obtained in Example 53 in place of Compound 64. Then, the resultant crude crystals were recrystallized from toluene/cyclohexane to give 1.01 g (yield 82%) of Compound 111 as yellow needles.

Melting Point: 176.5°–177.6° C.; Elemental Analysis: $C_{20}H_{24}N_4O_3$, Calcd. (%): C, 65.20; H, 6.57; N, 15.21; Found (%): C, 65.22; H, 6.75; N, 15.22; IR (KBr) $v_{max}$ ($cm^{-1}$): 1687, 1648, 1542, 1505, 1434; NMR (270 MHz; DMSO-$d_6$)δ(ppm): 7.65(1H, s), 7.58(1H, d, J=15.8 Hz), 7.57–7.53 (1H, m), 7.16 (1H, d, J=15.8 Hz), 6.97(1H, d, J=8.9 Hz), 4.10–4.01(2H, m), 4.01(3H, s), 3.91(2H, q, J=6.9 Hz), 3.88(3H, s), 2.19 (3H, s), 1.25 (3H, t, J=6.9 Hz), 1.12 (3H, t, J=6.9 Hz).

EXAMPLE 55

(E)-8-(2-Bromo-4,5-methylenedioxystyryl)-1,3-diethylxanthine (Compound 158)

Substantially the same procedure as in Example 7 was repeated using 2.50 g (12.6 mmol) of 5,6-diamino-1,3-diethyluracil and 3.77 g (13.9 mmol) of 2-bromo-4,5-methylenedioxycinnamic acid. Then, the resultant crude crystals were recrystallized from dimethylsulfoxide/water to give 2.01 g (yield 38%) of Compound 158 as a yellow powder.

Melting Point: >270° C.; Elemental Analysis: $C_{18}H_{17}BrN_4O_4 \cdot 0.25H_2O$, Calcd. (%): C, 49.39; H, 4.03; N, 12.80; Found (%): C, 49.42; H, 3.75; N, 12.67; IR (KBr) $v_{max}$ ($cm^{-1}$): 1691, 1651, 1497; NMR (270 MHz; DMSO-$d_6$)δ(ppm): 7.78(1H, d, J=8.2 Hz), 7.48(1H, s), 7.30(1H, s), 6.97(1H, d, J=8.2 Hz), 6.13(2H, s), 4.05(2H, q, J=6.9 Hz), 3.93(2H, q, J=6.9 Hz), 1.24(3H, t, J=6.9 Hz), 1.13(3H, t, J=6.9 Hz).

EXAMPLE 56

(E)-8-(2-Bromo-4,5-methylenedioxystyryl)-1,3-diethyl-7-methylxanthine (Compound 159)

Substantially the same procedure as in Example 8 was repeated using 2.20 g (5.08 mmol) of Compound 158 obtained in Example 55 in place of Compound 64. Then, the resultant crude crystals were recrystallized from toluene/cyclohexane to give 1.17 g (yield 52%) of Compound as a pale yellow powder.

Melting Point: 255.1°–256.0° C.; Elemental Analysis: $C_{19}H_{19}BrN_4O_4$, Calcd. (%): C, 51.02; H, 4.28; N, 12.53; Found (%): C, 50.94; H, 4.15; N, 12.39; IR (KBr) $v_{max}$ ($cm^{-1}$): 1693, 1651; NMR (270 MHz; DMSO-$d_6$)δ(ppm): 7.87(1H, d, J=15.8 Hz), 7.77 (1H, s), 7.30 (1H, d, J=15.8 Hz), 7.32 (1H, s), 6.15 (2H, s), 4.10–4.03 (2H, m), 4.03 (3H, s), 3.92 (2H, q, J=6.8 Hz), 1.26(3H, t, J=7.2 Hz), 1.13(3H, t, J=6.8 Hz).

EXAMPLE 57

(E)-1,3-Diethyl-8-(3-methoxy-4,5-methylenedioxystyryl)xanthine (Compound 169)

Substantially the same procedure as in Example 7 was repeated using 2.50 g (12.6 mmol) of 5,6-diamino-1,3-diethyluracil and 3.31 g (14.9 mmol) of 3-methoxy-4,5-methylenedioxycinnamic acid. Then, the resultant crude crystals were recrystallized from tetrahydrofuran/water to give 600 mg (yield 53%) of Compound 169 as a white powder.

Melting Point: >270° C.; Elemental Analysis: $C_{19}H_{20}N_4O_5$, Calcd. (%): C, 59.37; H, 5.24; N, 14.58; Found (%): C, 59.41; H, 5.26; N, 14.66; IR (KBr) $v_{max}$ ($cm^{-1}$): 1689, 1654, 1640, 1506; NMR (270 MHz; DMSO-$d_6$)δ(ppm): 7.54(1H, d, J=16.6 Hz), 6.94 (2H, s), 6.93 (1H, d, J=16.6 Hz), 6.04 (2H, s), 4.05 (2H, q, J=6.9 Hz), 3.97–3.88 (2H, m), 3.88 (3H, s), 1.25(3H, t, J=7.2 Hz), 1.13(3H, t, J=7.2 Hz).

EXAMPLE 58

(E)-1,3-Diethyl-8-(3-methoxy-4,5-methylenedioxystyryl)-7-methylxanthine (Compound 170)

Substantially the same procedure as in Example 8 was repeated using 2.00 g (5.20 mmol) of Compound 169 obtained in Example 57 in place of Compound 64. Then, the resultant crude crystals were recrystallized from 2-propanol to give 730 mg (yield 35%) of Compound 170 as a yellow powder.

Melting Point: 201.5°–202.3° C.; Elemental Analysis: $C_{20}H_{22}N_4O_5$, Calcd. (%): C, 60.29; H, 5.57; N, 14.06; Found (%): C, 60.18; H, 5.72; N, 13.98; IR (KBr) $v_{max}$ ($cm^{-1}$): 1694, 1650, 1543, 1512, 1433; NMR (270 MHz; DMSO-$d_6$)δ(ppm): 7.58(1H, d, J=15.8 Hz), 7.23(1H, d, J=15.8 Hz), 7.20(1H, d, J=1.0 Hz), 7.09 (1H, d, J=1.0 Hz), 6.05 (2H, s), 4.09–4.02 (2H, m), 4.02(3H, s), 3.94–3.89(2H, m), 3.89(3H, s), 1.25 (3H, t, J=7.2 Hz), 1.13(3H, t, J=6.9 Hz).

EXAMPLE 59

Tablets

Tablets having the following composition were prepared in a conventional manner.

Compound 1 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined, thus obtaining granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter. The composition of each tablet thus prepared is shown below.

| Composition of One Tablet | |
|---|---|
| Compound 191 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 60

Fine Granules

Fine granules having the following composition were prepared in a conventional manner.

Compound 2 (20 g) was mixed with 655 g of lactose and 285 g of corn starch, followed by addition of 400 g of a 10% aqueous solution of hydroxypropylcellulose. The resultant mixture was kneaded, granulated, and then dried by a conventional method, thus obtaining fine granules containing 20 g of the active ingredient in 1,000 g. The composition of one pack of the fine granules is shown below.

| Composition of One Pack of Fine Granules | |
|---|---|
| Compound 83 | 20 mg |
| Lactose | 655 mg |
| Corn Starch | 285 mg |
| Hydroxypropylcellulose | 40 mg |
| | 1,000 mg |

EXAMPLE 61

Capsules

Capsules having the following composition were prepared in a conventional manner.

Compound 1 (200 g) was mixed with 995 g of Avicel and 5 g of magnesium stearate. The mixture was put in hard capsules No. 4 each having a capacity of 120 mg by using a capsule filler (Model LZ-64, Zanashi), thus obtaining capsules each containing 20 mg of the active ingredient. The composition of one capsule thus prepared is shown below.

| Composition of One Capsule | |
|---|---|
| Compound 1 | 20 mg |
| Avicel | 99.5 mg |
| Magnesium Stearate | 0.5 mg |
| | 120 mg |

EXAMPLE 62

Injections

Injections having the following composition were prepared in a conventional manner.

Compound 2 (1 g) was dissolved in 100 g of purified soybean oil, followed by addition of 12 g of purified egg yolk lecithin and 25 g of glycerine for injection. The resultant mixture was made up to 1,000 ml with distilled water for injection, thoroughly mixed, and emulsified by a conventional method. The resultant dispersion was subjected to aseptic filtration by using 0.2 μm disposable membrane filters, and then aseptically put into glass vials in 2 ml portions, thus obtaining injections containing 2 mg of the active ingredient per vial. The composition of one injection vial is shown below.

| Composition of One Injection Vial | |
|---|---|
| Compound 2 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

EXAMPLE 63

Tablets

Tablets having the following composition were prepared in a conventional manner.

| Composition of One Tablet | |
|---|---|
| Compound 65 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 64

Fine Granules

Fine granules having the following composition were prepared in a conventional manner.

| Composition of On Pack of Fine Granules | |
|---|---|
| Compound 170 | 20 mg |
| Lactose | 655 mg |
| Corn Starch | 285 mg |
| Hydroxypropylcellulose | 40 mg |
| | 1,000 mg |

EXAMPLE 65

Capsules

Capsules having the following composition were prepared in a conventional manner.

| Composition of One Capsule | |
|---|---|
| Compound 71 | 20 mg |
| Avicel | 99.5 mg |
| Magnesium Stearate | 0.5 mg |
| | 120 mg |

EXAMPLE 66

Injections

Injections having the following composition were prepared in a conventional manner.

| Composition of One Injection Vial | |
|---|---|
| Compound 73 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

EXAMPLE 67

Syrup Preparations

Syrup Preparations having the following composition were prepared in a conventional manner.

| Composition of One Syrup Preparation | |
|---|---|
| Compound 77 | 20 mg |
| Refined Sugar | 30 mg |
| Ethyl p-Hydroxybenzoate | 40 mg |
| Propyl p-Hydroxybenzoate | 10 mg |
| Strawberry Flavor | 0.1 ml |
| Water | 99.8 ml |
| | 100 ml |

REFERENCE EXAMPLE 1

(E)-8-(3,4-Dimethoxystyryl)-7-methyl-1,3-dipropylxanthine (Compound 1)

3,4-Dimethoxycinnamic acid (2.03 g, 9.74 mmol) and 3-(3-diethylaminopropyl)-1-ethylcarbodiimide hydrochloride (2.54 g, 13.3 mmol) were added to a mixture of water (60 ml) and dioxane (30 ml) containing 5,6-diamino-1,3dipropyluracil (U.S. Patent No. 2,602,795) (2.00 g, 8.85 mmol). The resultant solution was stirred at room temperature for 2 hours at pH 5.5. After neutralization, the reaction solution was extracted three times with 50 ml of chloroform. The combined extract was washed with a saturated aqueous solution of sodium chloride and dried over anhydrous sodium sulfate, followed by evaporation under reduced pressure. The residue was purified by silica gel column chromatography (eluent: 2% methanol/chloroform) to give 3.47 g (yield 94%) of (E)-6-amino-5-(3,4 -dimethoxycinnamoyl)amino-1,3-dipropyluracil (Compound A) as an amorphous substance.

NMR (CDCl$_3$; 90 MHz)$\delta$(ppm): 7.84(1H, brs), 7.50(1H, d, J=15.9 Hz), 7.10–6.65 (3H, m), 6.53 (1H, d, J=15.9 Hz), 5.75 (2H, brs), 4.00–3.50 (4H, m), 3.85(6H, brs), 2.00–1.40(4H, m), 1.10–0.80(6H, m).

To 3.38 g (8.13 mmol) of Compound A were added 40 ml of dioxane and 80 ml of an aqueous 1N sodium hydroxide solution, followed by heating under reflux for 10 minutes. After cooling, the solution was neutralized, and deposited crystals were collected by filtration. Then, the collected crystals were recrystallized from dimethylsulfoxide/water to give 2.49 g (yield 77%) of (E)-8-(3,4-dimethoxystyryl)-1, 3-dipropylxanthine (Compound B) as white crystals.

Melting Point: 260.0°–263.8° C.; Elemental Analysis: C$_{12}$H$_{26}$N$_4$O$_4$, Calcd. (%): C, 63.30; H, 6.57; N, 14.06; Found (%): C, 63.29; H, 6.79; N, 14.21; IR (KBr) $v_{max}$ (cm$^{-1}$): 1701, 1640; NMR (DMSO-d$_6$; 270 MHz)$\delta$(ppm): 13.39(1H, brs), 7.59 (1H, d, J=16.7 Hz), 7.26(1H, d, J=1.8 Hz), 7.13(1H, dd, J=1.8, 8.6 Hz), 6.98 (1H, d, J=8.6 Hz), 6.95 (1H, d, J=16.7 Hz), 3.99(2H, t), 4.00–3.85(2H, t), 3.83(3H, s), 3.80(3H, s), 1.80–1.55(4H, m), 1.00– 0.85 (6H, m).

Compound B (1.20 g, 3.02 mmol) was dissolved in 20 ml of dimethylformamide. To the solution were added 1.04 g (7.55 mmol) of potassium carbonate and subsequently 0.38 ml (6.04 mmol) of methyl iodide, and the resultant mixture was stirred at 50° C. for 30 minutes. After cooling, insoluble matters were filtered off, and 400 ml of water was added to the filtrate. The mixture was extracted three times with 100 ml of chloroform. The extract was washed twice with water and once with a saturated aqueous solution of sodium chloride, and dried over anhydrous sodium sulfate, followed by evaporation under reduced pressure. The residue was purified by silica gel column chromatography (eluent: 1% methanol/chloroform), followed by recrystallization from propanol/water to give 1.22 g (yield 98%) of Compound 1 as white needles.

Melting Point: 164.1°–166.3° C.; Elemental Analysis: C$_{22}$H$_{28}$N$_4$O$_4$, Calcd. (%): C, 64.06; H, 6.84; N, 13.58; Found (%): C, 64.06; H, 6.82; N, 13.80; IR (KBr) $v_{max}$ (cm$^{-1}$): 1692, 1657; NMR (DMSO-d$_6$; 270 MHz)$\delta$(ppm): 7.60(1H, d, J=15.8 Hz), 7.40 (1H, d, 2.0 Hz), 7.28 (1H, dd, J=2.0, 8.4 Hz), 7.18(1H, d, J=15.8 Hz), 6.99(1H, d, J=8.4 Hz), 4.02(3H, s), 3.99(2H, t), 3.90–3.80(2H, m), 3.85(3H, s), 3.80(3H, s), 1.80–1.55(4H, m), 1.00– 0.85 ( 6H, m)

REFERENCE EXAMPLE 2

(E)-7-Methyl-1,3-dipropyl-8-styrylxanthine (Compound 3)

5,6-Diamino-1,3-dipropyluracil (U.S. Pat. No. 2,602,795) (6.0 g, 26.5 mmol) was slowly added to a mixture of methanol (360 ml) and acetic acid (15 ml) containing cinnamaldehyde (3.34 ml, 26.5 mmol) under ice cooling. The resultant mixture was stirred at room temperature for 30 minutes, followed by evaporation under reduced pressure to give 6.30 g (yield 70%) of (E)-6-amino-5-(3-phenyl-3 -propenylidene)-1,3-dipropyluracil (Compound C) as an amorphous substance.

Melting Point: 159.5°–161.0° C.; IR (KBr) $v_{max}$ (cm$^{-1}$): 1687, 1593; NMR (CDCl$_3$; 90 MHz)$\delta$(ppm): 9.75–9.60(1H, m), 7.60– 7.25(5H, m), 7.00–6.80(2H, m), 5.70(brs, 2H), 4.00–3.70(4H, m), 2.00–1.40(4H, m), 1.10–0.75 (6H, m); MS m/e (relative intensity): 340(100, M$^+$), 130(86).

To 6.30 g (18.5 mmol) of Compound C was added 240 ml of ethanol, and the mixture was heated under reflux for 2 hours in the presence of 4.32 g (26.5 mmol) of ferric chloride. After cooling, deposited crystals were collected by filtration to give 3.61 g (yield 61%) of (E)-1,3 -dipropyl-8-styrylxanthine (Compound D) as white crystals.

Melting Point: 259.3°–261.0° C. (recrystallized from ethanol); Elemental Analysis: C$_{19}$H$_{22}$N$_4$O$_2$, Calcd. (%): C, 67.43; H, 6.55; N, 16.56; Found (%): C, 67.40; H, 6.61; N, 16.71; IR (KBr) $v_{max}$ (cm$^{-1}$): 1700, 1650, 1505; NMR (DMSO-d$_6$)$\delta$(ppm): 13.59(1H, brs), 7.70–7.55 (3H, m), 7.50–7.30(3H, m), 7.06(1H, d, J= 16.5 Hz), 3.99(2H, t), 3.86(2H, t), 2.80–2.50(4H, m), 0.95–0.80 (6H, m).

Subsequently, the same procedure as in Reference Example 1 was repeated using Compound D in place of Compound B to give 1.75 g (yield 84%) of Compound 3 as white needles.

Melting Point: 162.8°–163.2° C.; Elemental Analysis: $C_{20}H_{24}N_4O_2$, Calcd. (%): C, 68.16; H, 6.86; N, 15.90; Found (%): C, 67.94; H, 6.96; N, 16.15; IR (KBr) $v_{max}$ (cm$^{-1}$): 1690, 1654, 1542, 1450, 1437; NMR (CDCl$_3$)δ(ppm): 7.79(1H, d, J=15.8 Hz), 7.65–7.55(2H, m), 7.48–7.35(3H, m), 6.92(1H, d, J=15.8 Hz), 4.11 (2H, t), 4.06 (3H, s), 3.98 (2H, t), 2.00–1.60 (4H, m), 1.08–0.95 (6H, m).

REFERENCE EXAMPLE 3

(E)-1,3-Dipropyl-8-(3,4,5-trimethoxystyryl)xanthine (Compound 9)

3,4,5-Trimethoxycinnamic acid (5.78 g, 24.3 mmol) and 6.36 g (33.2 mmol) of 3-(3-diethylaminopropyl)-1-ethylcarbodiimide hydrochloride were added to a mixture of dioxane (150 ml) and water (75 ml) containing 5.00 g (22.1 mmol) of 5,6-diamino-1,3-dipropyluracil. The resultant solution was stirred at room temperature at pH 5.5 for one hour. After the reaction, the solution was adjusted to pH 7 and extracted three times with chloroform. The combined extract was washed with a saturated aqueous solution of sodium chloride and dried over anhydrous sodium sulfate, followed by evaporation under reduced pressure. The residue was purified by silica gel column chromatography (eluent: 3% methanol/chloroform) to give 8.06 g (yield 82%) of (E)-6-amino-1,3-dipropyl-5-(3,4,5-trimethoxycinnamoyl)aminouracil (Compound E) as an amorphous substance.

NMR (CDCl$_3$; 90 MHz)δ(ppm): 7.85(1H, brs), 7.48(1H, d, J=15.6 Hz), 6.67 (2H, s), 6.56 (1H, d, J=15.6 Hz), 5.80(2H, brs), 4.00–3.70(4H, m), 3.89(9H, s), 1.80–1.45(4H, m), 1.15–0.80(6H, m).

To 10.02 g (22.5 mmol) of Compound E were added 100 ml of dioxane and 100 ml of an aqueous 2N sodium hydroxide solution, and the solution was heated under reflux for 10 minutes. After cooling, the solution was neutralized, and deposited crystals were collected by filtration. Then, the collected crystals were recrystallized from dioxane/water to give 6.83 g (yield 91%) of (E)-1,3-dipropyl-8-(3,4,5-trimethoxystyryl)xanthine (Compound 9) as white crystals.

Melting Point: 161.8°–162.6° C.; Elemental Analysis: $C_{22}H_{28}N_4O_5$, Calcd. (%): C, 61.66; H, 6.58; N, 13.07; Found (%): C, 61.73; H, 6.37; N, 13.08; IR (KBr) $v_{max}$ (cm$^{-1}$): 1702, 1643; NMR (CDCl$_3$; 90 MHz)δ(ppm): 12.87 (1H, brs), 7.72 (1H, d, J=16.3 Hz), 6.96 (1H, d, J=16.3 Hz), 6.81 (2H, s), 4.30–3.95(4H, m), 3.92(6H, s), 3.90(3H, s), 2.10–1.50 (4H, m), 1.02 (2H, t), 0.90 (2H, t).

REFERENCE EXAMPLE 4

(E)-7-Methyl-1,3-dipropyl-8-(3,4,5-trimethoxystyryl)xanthine (Compound 5)

The same procedure as in Reference Example 1 was repeated using Compound 9 in place of Compound B to give 1.75 g (yield 84%) of Compound 5 as white needles.

Melting Point: 168.4–169.1° C. (recrystallized from ethanol/water); Elemental Analysis: $C_{23}H_{30}N_4O_5$, Calcd. (%): C, 62.42; H, 6.83; N, 12.66; Found (%): C, 62.48; H, 6.60; N, 12.70; IR (KBr) $v_{max}$ (cm$^{-1}$): 1698, 1659; NMR (CDCl$_3$; 90 MHz)δ(ppm): 7.71(1H, d, J=15.8 Hz), 6.86(2H, s), 6.78(1H, d, J=15.8 Hz), 4.30–3.95(4H, m), 4.07(3H, s), 3.93(6H, s), 3.90(3H, s), 2.05–1.50 (4H, m), 1.20–0.85 (6H, m).

REFERENCE EXAMPLE 5

(E)-8-(4-Methoxystyryl)-7-methyl-1,3-dipropylxanthine (Compound 6)

Substantially the same procedure as in Reference Example 1 was repeated using 2.00 g (8.85 mmol) of 5,6-diamino-1,3-dipropyluracil and 1.73 g (9.74 mmol) of 4-methoxycinnamic acid to give 2.29 g (overall yield 68%) of Compound 6.

Melting Point: 159.8°–161.3° C. (recrystallized from ethanol/water); Elemental Analysis: $C_{21}H_{26}N_4O_3$, Calcd. (%): C, 65.94; H, 6.85; N, 14.64; Found (%): C, 65.92; H, 6.90; N, 14.88; IR (KBr) $v_{max}$ (cm$^{-1}$): 1695, 1658; NMR (DMSO-d$_6$)δ(ppm): 7.72(2H, d, J=8.8 Hz), 7.61(1H, d, J=15.8 Hz), 7.16(1H, d, J=15.8 Hz), 4.05–3.95 (2H, m), 4.00 (3H, s), 3.83 (2H, t), 3.80(3H, s), 1.85–1.50(4H, m), 1.00–0.85(6H, m).

REFERENCE EXAMPLE 6

(E)-1,3-Diallyl-8-(3,4,5-trimethoxystyryl)xanthine (Compound 11)

Substantially the same procedure as in Reference Example 3 was repeated using 3.0 g (13.5 mmol) of 1,3-diallyl-5,6-diaminouracil and 3.55 g (14.9 mmol) of 3,4,5-trimethoxycinnamic acid to give 4.48 g (yield 75%) of (E)-1,3-diallyl-6-amino-5-(3,4,5-trimethoxycinnamoyl)aminouracil (Compound F) as an amorphous substance.

NMR (CDCl$_3$; 90 MHz)δ(ppm): 7.90(1H, brs), 7.56(1H, d, J=16.0 Hz), 6.71(2H, s), 6.57(1H, d, J=16.0 Hz), 6.15–5.60 (4H, m), 5.50–5.05 (4H, m), 4.75–4.45 (4H, m), 3.90 (9H, s).

Substantially the same procedure as in Reference Example 3 was repeated using 4.34 g (9.82 mmol) of Compound F in place of Compound E to give 2.81 g (yield 68%) of Compound 11 as a pale yellowish green powder.

Melting Point: 253.1°–255.4° C. (recrystallized from dioxane); Elemental Analysis: $C_{22}H_{24}N_4O_5 \cdot \frac{1}{2}H_2O$, Calcd. (%): C, 60.96; H, 5.81; N, 12.93; Found (%): C, 61.05; H, 5.60; N, 12.91; IR (KBr) $v_{max}$ (cm$^{-1}$): 1704, 1645, 1583, 1510; NMR (CDCl$_3$)δ(ppm): 12.94(1H, brs), 7.73(1H, d, J=16.3 Hz), 7.05(1H, d, J=16.3 Hz), 6.81(2H, s), 6.12–5.92 (2H, m), 5.37–5.22 (4H, m), 4.83–4.76 (4H, m), 3.91(6H, s), 3.90(3H, s).

REFERENCE EXAMPLE 7

(E)-1,3-Diallyl-7-methyl-8-(3,4,5-trimethoxystyryl)xanthine (Compound 7)

Substantially the same procedure as in Reference Example 1 was repeated using 1.13 g (2.67 mmol) of Compound 11 in place of Compound B to give 620 mg (yield 53%) of Compound 7 as pale yellow needles.

Melting Point: 189.0°–191.1° C. (recrystallized from ethyl acetate); Elemental Analysis: $C_{23}H_{26}N_4O_5$, Calcd. (%): C, 63.00; H, 5.97; N, 12.77; Found (%): C, 63.00; H, 6.05; N, 12.85; IR (KBr) $v_{max}$ (cm$^{-1}$): 1699, 1660; NMR (CDCl$_3$; 90 MHz)δ(ppm): 7.78(1H, d, J=16.0 Hz), 6.85 (2H, s), 6.84 (1H, d, J=16.0 Hz), 6.30–5.75 (2H, m), 5.45–5.10 (4H, m), 4.85–4.55 (4H, m), 4.07 (3H, s), 3.92 (6H, s), 3.90 (3H, s).

REFERENCE EXAMPLE 8

(E)-1,3-Dibutyl-7-methyl-8-(3,4,5-trimethoxystyryl)xanthine (Compound 8)

Substantially the same procedure as in Reference Example 1 was repeated using 4.75 g (18.7 mmol) of 5,6-diamino-1,3-dibutyluracil and 4.90 g (20.6 mmol) of 3,4,5-trimethoxycinnamic acid to give 5.49 g (overall yield 63%) of Compound 8 as a pale green powder.

Melting Point: 136.8°–137.3° C. (recrystallized from ethanol/water); Elemental Analysis: $C_{25}H_{34}N_4O_5$, Calcd. (%): C, 63.81; H, 7.28; N, 11.91; Found (%): C, 63.63; H, 6.93; N, 11.99; IR (KBr) $\nu_{max}$ (cm$^{-1}$): 1692, 1659; NMR (CDCl$_3$; 90 MHz)δ(ppm): 7.68 (1H, d, J=15.8 Hz), 6.80 (2H, s), 6.79(1H, d, J=15.8 Hz), 4.30–3.90 (4H, m), 4.03 (3H, s), 3.95 (6H, s), 3.91(3H, s), 1.90

1.10(8H, m), 1.05–0.80 (6H, m).

REFERENCE EXAMPLE 9

(E)-8-(4-Methoxy-2,3-dimethylstyryl)-1,3-dipropylxanthine (Compound 12)

Substantially the same procedure as in Reference Example 1 was repeated using 2.31 g (10.24 mmol) of 5,6-diamino-1,3-dipropyluracil and 2.42 g (15.4 mmol) of 4-methoxy-2,3-dimethylcinnamic acid. Then, the resultant crude crystals were recrystallized from dioxane/water to give 1.96 g (yield 48%) of Compound 12 as a white powder.

Melting Point: 270.7°–271.3° C.; Elemental Analysis: $C_{22}H_{28}N_4O_3$, Calcd. (%): C, 66.64; H, 7.11; N, 14.13; Found (%): C, 66.68; H, 7.20; N, 14.04; IR (KBr) $\nu_{max}$ (cm$^{-1}$): 1704, 1650, 1591, 1269; NMR (DMSO-d$_6$; 270 MHz)δ(ppm): 7.93(1H, d, J=16.3 Hz), 7.57(1H, d, J=8.9 Hz), 6.88(1H, d, J=8.9 Hz), 6.82(1H, d, J=16.3 Hz), 3.98(2H, t, J=7.1 Hz), 3.86(2H, t, J=7.3 Hz), 3.81(3H, s), 2.32(3H, s), 2.09(3H, s), 1.80–1.55(4H, m), 0.95–0.80(6H, m).

REFERENCE EXAMPLE 10

(E)-8-(4-Methoxy-2,3-dimethylstyryl)-7-methyl-1,3dipropylxanthine (Compound 13)

Substantially the same procedure as in Reference Example 1 was repeated using 4.00 g (5.10 mmol) of Compound 12 obtained in Reference Example 9 in place of Compound B to give 1.73 g (yield 83%) of Compound 13 as yellow needles.

Melting Point: 171.0°–173.5° C.; Elemental Analysis: $C_{23}H_{30}N_4O_3$, Calcd. (%): C, 67.29; H, 7.36; N, 13.64; Found (%): C, 66.87; H, 7.67; N, 13.51; IR (KBr) $\nu_{max}$ (cm$^{-1}$): 1697, 1659, 1593, 1493; NMR (CDCl$_3$; 270 MHz)δ(ppm): 8.07 (1H, d, J=15.3 Hz), 7.46 (1H, d, J=8.4 Hz), 6.77 (1H, d, J=8.4 Hz), 6.67(1H, d, J=15.3 Hz), 4.12 (2H, t, J=7.3 Hz), 4.03(3H, s), 3.98(2H, t, J=7.3 Hz), 3.86(3H, s), 2.39 (3H, s), 2.26 (3H, s), 1.85–1.50 (4H, m), 1.05–0.90 (6H, m).

REFERENCE EXAMPLE 11

(E)-8-(2,4-Dimethoxy-3-methylstyryl)-1,3-dipropylxanthine (Compound 14)

Substantially the same procedure as in Reference Example 1 was repeated using 1.25 g (5.52 mmol) of 5,6-diamino-1,3-dipropyluracil and 1.35 g (6.08 mmol) of 2,4-dimethoxy-3-methylcinnamic acid. Then, the resultant crude crystals were recrystallized from dioxane/water to give 1.14 g (yield 50%) of Compound 14 as white needles.

Melting Point: 255.2°–256.0° C.; Elemental Analysis: $C_{22}H_{28}N_4O_4$, Calcd. (%): C, 64.06; H, 6.84; N, 13.58; Found (%): C, 63.77; H, 7.01; N, 13.42; IR (KBr) $\nu_{max}$ (cm$^{-1}$): 1694, 1650, 1594, 1495; NMR (DMSO-d$_6$; 270 MHz)δ(ppm): 13.54(1H, brs), 7.76 (1H, d, J=16.5 Hz), 7.59(1H, d, J=8.9 Hz), 6.99(1H, d, J=16.5 Hz), 6.84(1H, d, J=8.9 Hz), 3.99(2H, t, J=7.4 Hz), 3.85(2H, t, J=7.3 Hz), 3.83(3H, s), 3.70 (3H, s), 2.09 (3H, s), 1.80–1.55 (4H, m), 0.95– 0.80 (6H, m).

REFERENCE EXAMPLE 12

(E)-8-(2,4-Dimethoxy-3-methylstyryl)-7-methyl-1,3-dipropylxanthine (Compound 15)

Substantially the same procedure as in Reference Example 1 was repeated using 1.10 g (2.67 mmol) of Compound 14 obtained in Reference Example 11 in place of Compound B. Then, the resultant crude crystals were recrystallized from ethanol/2-propanol to give 620 mg (yield 55%) of Compound 15 as pale yellow grains.

Melting Point: 191.4°–191.8° C.; Elemental Analysis: $C_{23}H_{30}N_4O_4$, Calcd. (%): C, 64.76; H, 7.08; N, 13.13; Found (%): C, 64.84; H, 7.30; N, 12.89; IR (KBr) $\nu_{max}$ (cm$^{-1}$): 1695, 1654, 1274, 1107; NMR (CDCl$_3$; 270 MHz)δ(ppm): 7.91(1H, d, J=15.8 Hz), 7.42(1H, d, J=8.6 Hz), 6.98(1H, d, J=15.8 Hz), 6.69 (1H, d, J=8.6 Hz), 4.11(2H, t, J=7.4 Hz), 4.03(3H, s), 4.03–3.95 (2H, m), 3.87 (3H, s), 3.77 (3H, s), 2.19(3H, s), 1.85–1.55(4H, m), 1.03–0.94(6H, m).

REFERENCE EXAMPLE 13

(E)-1,3-Dipropyl-8-(2,3,4-trimethoxystyryl)xanthine (Compound 20)

Substantially the same procedure as in Reference Example 1 was repeated using 2.00 g (8.85 mmol) of 5,6-diamino-1,3-dipropyluracil and 2.32 g (9.73 mmol) of 2,3,4-trimethoxycinnamic acid. Then, the resultant crude crystals were recrystallized from 2-propanol/water to give 1.84 g (yield 49%) of Compound 20 as pale yellow needles.

Melting Point: 246.5°–246.8° C.; Elemental Analysis: $C_{22}H_{28}N_4O_5$, Calcd. (%): C, 61.66; H, 6.58; N, 13.07; Found (%): C, 61.50; H, 6.89; N, 13.06; IR (KBr) $\nu_{max}$ (cm$^{-1}$): 1703, 1651, 1504; NMR (CDCl$_3$; 270 MHz)δ(ppm): 12.72(1H, brs), 7.92 (1H, d, J=16.5 Hz), 7.31(1H, d, J=8.7 Hz), 7.09(1H, d, J=16.5 Hz), 6.71(1H, d, J=8.7 Hz), 4.25–4.10(4H, m), 3.95(3H, s), 3.91(3H, s), 3.90(3H, s), 2.00– 1.65 (4H, m), 1.10–0.85 (6H, m).

REFERENCE EXAMPLE 14

(E)-7-Methyl-1,3-dipropyl-8-(2,3,4-trimethoxystyryl)xanthine (Compound 21)

Substantially the same procedure as in Reference Example 1 was repeated using 2.50 g (5.84 mmol) of Compound 20 obtained in Reference Example 13 in place of Compound B. Then, the resultant crude crystals were recrystallized from ethanol to give 1.70 g (yield 66%) of Compound 21 as yellow needles.

Melting Point: 153.5°–153.8° C.; Elemental Analysis: $C_{23}H_{30}N_4O_5$, Calcd. (%): C, 62.42; H, 6.83; N, 12.66; Found (%): C, 62.77; H, 7.25; N, 12.65; IR (KBr) $\nu_{max}$ (cm$^{-1}$): 1699, 1657, 1590, 1497, 1439; NMR (CDCl$_3$; 270 MHz)δ(ppm): 7.88 (1H, d, J=15.8 Hz), 7.28 (1H, d, J=8.9 Hz), 7.02(1H, d, J=15.8 Hz), 6.71 (1H, d, J=8.9 Hz), 4.25–3.95 (4H, m), 4.03 (3H, s), 3.97 (3H, s), 3.91 (3H, s), 3.90 (3H, s), 2.00–1.65 (4H, m), 1.10–0.85 (6H, m).

REFERENCE EXAMPLE 15

(E)-1,3-Dipropyl-8-(2,4,5-trimethoxystyryl)xanthine (Compound 22)

Substantially the same procedure as in Reference Example 1 was repeated using 2.00 g (8.85 mmol) of 5,6-diamino-1,3-dipropyluracil and 2.32 g (9.73 mmol) of 2,4,5-trimethoxycinnamic acid. Then, the resultant crude crystals were recrystallized from 2-propanol/water to give 870 mg (yield 23%) of Compound 22 as a pale yellow powder.

Melting Point: 254.5°–255.7° C.; Elemental Analysis: C$_{22}$H$_{28}$N$_4$O$_5$, Calcd. (%): C, 61.66; H, 6.58; N, 13.07; Found (%): C, 61.94; H, 6.97; N, 13.06; IR (KBr) ν$_{max}$ (cm$^{-1}$): 1693, 1650, 1517; NMR (CDCl$_3$; 270 MHz)δ(ppm): 12.53 (1H, brs), 7.97 (1H, d, J=16.5 Hz), 7.10(1H, s), 6.99(1H, d, J=16.5 Hz), 6.54(1H, s), 4.25–4.10(4H, m), 3.95(3H, s), 3.90(6H, s), 1.90–1.65(4H, m), 1.01(3H, t, J=7.6 Hz), 0.86 (3H, t, J=7.6 Hz).

REFERENCE EXAMPLE 16

(E)-7-Methyl-1,3-dipropyl-8-(2,4,5-trimethoxystyryl) xanthine (Compound 23)

Substantially the same procedure as in Reference Example 1 was repeated using 0.5 g (1.17 mmol) of Compound 22 obtained in Reference Example 15 in place of Compound B. Then, the resultant crude crystals were recrystallized from toluene/hexane to give 200 mg (yield 39%) of Compound 23 as a pale yellow powder.

Melting Point: 195.5–196.2° C.; Elemental Analysis: C$_{23}$H$_{30}$N$_4$O$_5$, Calcd. (%): C, 62.42; H, 6.83; N, 12.66; Found (%): C, 62.14; H, 7.12; N, 12.56; IR (KBr)ν$_{max}$ (cm$^{-1}$): 1688, 1653, 1515, 1439, 1214; NMR (CDCl$_3$; 270 MHz)δ(ppm): 7.93(1H, d, J=15.8 Hz), 7.05 (1H, s), 6.94 (1H, d, J=15.8 Hz), 6.54 (1H, s), 4.15–3.90 (4H, m), 4.04 (3H, s), 3.95 (3H, s), 3.93 (3H, s), 3.91(3H, s), 1.90–1.65(4H, m), 1.03–0.94 (6H, m).

REFERENCE EXAMPLE 17

(E)-8-(2,4-Dimethoxystyryl)-1,3-dipropylxanthine (Compound 24)

Substantially the same procedure as in Reference Example 1 was repeated using 3.0 g (13.3 mmol) of 5,6-diamino-1,3-dipropyluracil and 3.04 g (14.60 mmol) of 2,4-dimethoxycinnamic acid. Then, the resultant crude crystals were recrystallized from dioxane/water to give 1.26 g (yield of Compound 24 as white crystals.

Melting Point: 273.1°–273.7° C.; Elemental Analysis: C$_{21}$H$_{26}$N$_4$O$_4$, Calcd. (%): C, 63.30; H, 6.57; N, 14.06; Found (%): C, 62.94; H, 6.78; N, 14.03; IR (KBr) ν$_{max}$ ($^{cm-1}$): 1693, 1645, 1506; NMR (DMSO-d$_6$; 270 MHz)δ(ppm): 13.39(1H, brs), 7.78 (1H, d, J=16.5 Hz), 7.54 (1H, d, J=8.2 Hz), 6.95 (1H, d, J=16.5 Hz), 6.63 (1H, d, J=2.3 Hz), 6.00 (1H, dd, J=8.2, 2.3 Hz), 4.01–3.85(4H, m), 3.89(3H, s), 3.82 (3H, s), 1.79–1.50(4H, m), 0.93–0.87(6H, m).

REFERENCE EXAMPLE 18

(E)-8-(2,4-Dimethoxystyryl)-7-methyl-1,3-dipropylxanthine (Compound 25)

Substantially the same procedure as in Reference Example 1 was repeated using 600 mg (1.51 mmol) of Compound 24 obtained in Reference Example 17 in place of Compound B. Then, the resultant crude crystals were recrystallized from hexane/ethyl acetate to give 556 mg (yield 90%) of Compound 25 as brown needles.

Melting Point: 167.6°–167.9° C.; Elemental Analysis: C$_{22}$H$_{28}$N$_4$O$_4$, Calcd. (%): C, 64.06; H, 6.84; N, 13.58; Found (%): C, 63.98; H, 6.94; N, 13.61; IR (KBr) ν$_{max}$ (cm$^{-1}$): 1691, 1653, 1603, 1437; NMR (CDCl$_3$; 270 MHz)δ(ppm): 7.92(1H, d, J=15.8 Hz), 7.48 (1H, d, J=8.6 Hz), 6.98 (1H, d, J=15.8 Hz), 6.54 (1H, dd, J=8.6, 2.3 Hz), 6.50(1H, d, J=2.3 Hz), 4.14–3.95 (4H, m), 4.02 (3H, s), 3.93 (3H, s), 3.86 (3H, s), 1.91–1.65(4H, m), 1.03–0.94(6H, m).

REFERENCE EXAMPLE 19

(E)-8-(4-Benzyloxy-3,5-dimethoxystyryl)-1,3-dipropylxanthine (Compound 26)

A mixture of 5.0 g (22.3 mmol) of 4-hydroxy-3,5-dimethoxycinnamic acid, 8.0 ml (66.9 mmol) of benzyl bromide, and potassium carbonate was stirred in 50 ml of dimethylformamide at 70° C. for 2 hours. Insoluble matters were filtered off and the filtrate was poured into 500 ml of water. The mixture was extracted three times with 100 ml of chloroform. The extract was washed twice with water and twice with a saturated aqueous solution of sodium chloride, and dried over anhydrous sodium sulfate, followed by evaporation under reduced pressure. To the residue were added 50 ml of an aqueous 2N sodium hydroxide solution and 50 ml of ethanol, followed by heating under reflux for 15 minutes. After cooling, the solution was adjusted to pH 3 with a concentrated hydrochloric acid solution and extracted three times with 50 ml of chloroform. The extract was washed with a saturated aqueous solution of sodium chloride, and dried over anhydrous sodium sulfate, followed by evaporation under reduced pressure. The residue was recrystallized from hexane to give 5.4 g (yield 77%) of (E)-4-benzyloxy-3,5-dimethoxycinnamic acid (Compound G) as pale yellow needles.

Melting Point: 101.8°–102.3° C.; Elemental Analysis: C$_{18}$H$_{18}$O$_5$, Calcd. (%): C, 68.77; H, 5.77; Found (%): C, 68.95; H, 5.79; IR (KBr) ν$_{max}$ (cm$^{-1}$): 2900(br), 1683, 1630, 1579, 1502, 1281, 1129; NMR (CDCl$_3$; 90 MHz)δ(ppm): 7.80(1H, d, J=16 Hz), 7.55– 7.20(5H, m), 6.80(2H, s), 6.30(1H, d, J=16 Hz), 5.08 (2H, s).

Substantially the same procedure as in Reference Example 1 was repeated using 3.30 g (14.5 mmol) of 5,6-diamino-1,3-dipropyluracil and 5.0 g (15.9 mmol) of Compound G. Then, the resultant crude crystals were recrystallized from ethanol/2-propanol to give 5.44 g (yield 74%) of Compound 26 as a white powder.

Melting Point: 221.1°–221.4° C.; Elemental Analysis: C$_{28}$H$_{32}$N$_4$O$_5$, Calcd. (%): C, 66.65; H, 6.39; N, 11.10; Found (%): C, 66.65; H, 6.51; N, 11.01; IR (KBr) ν$_{max}$ (cm$^{-1}$): 1704, 1637, 1582, 1505; NMR (CDCl$_3$; 90 MHz)δ(ppm): 7.69 (1H, d, J=16 Hz), 7.55– 7.20 (5H, m), 6.96 (1H, d, J=16 Hz), 6.80 (2H, s), 5.08(2H, s), 4.25–3.95(4H, m), 3.88(6H, s), 2.10– 1.65 (4H, m), 1.20–0.80 (6H, m).

REFERENCE EXAMPLE 20

(E)-8-(4-Benzyloxy-3,5-dimethoxystyryl)-7-methyl-1,3-dipropylxanthine (Compound 27)

Substantially the same procedure as in Reference Example 1 was repeated using 8.20 g (14.5 mmol) of Compound 26 obtained in Reference Example 19 in place of Compound B. Then, the resultant crude crystals were recrystallized from 2-propanol/water acetate to give 4.78 g (yield 64%) of Compound 27 as a white powder.

Melting Point: 164.7°–165.1° C.; Elemental Analysis: $C_{29}H_{34}N_4O_5$, Calcd. (%): C, 67.16; H, 6.60; N, 10.80; Found (%): C, 67.01; H, 6.61; N, 10.70; IR (KBr) $v_{max}$ (cm$^{-1}$): 1695, 1659, 1580, 1542, 1505, 1455, 1335; (CDCl$_3$; 90 MHz)δ(ppm): 7.70(1H, d, J=16 Hz), 7.55– 7.20 (5H, m), 6.78 (2H, s), 6.72 (1H, d, J=16 Hz), 5.07 (2H, s), 4.25–3.95(4H, m), 4.07(3H, s), 3.89 (6H, s), 2.10–1.65(4H, m), 1.20–0.85(6H, m).

REFERENCE EXAMPLE 21

(E)-8-(2,3-Dimethoxystyryl)-1,3-dipropylxanthine (Compound 28)

Substantially the same procedure as in Reference Example 1 was repeated using 2.0 g (8.85 mmol) of 5,6-diamino-1,3-dipropyluracil and 2.2 g (10.6 mmol) of 2,3-dimethoxycinnamic acid. Then, the resultant crude crystals were recrystallized from chloroform/cyclohexane to give 1.26 g (yield 36%) of Compound 28 as yellow crystals.

Melting Point 236.0°–236.5° C.; Elemental Analysis: $C_{21}H_{26}N_4O_4$, Calcd. (%): C, 63.30; H, 6.57; N, 14.06; Found (%): C, 62.99; H, 6.71; N, 13.83; IR (KBr) $v_{max}$ (cm$^{-1}$): 1701, 1652, 1271; NMR (DMSO-d$_6$; 270 MHz)δ(ppm): 13.63 (1H, brs), 7.84 (1H, d, J=16.8 Hz), 7.28(1H, d, J=6.8 Hz), 7.14–7.05 (3H, m), 4.00 (2H, t, J=7.3 Hz), 3.88–3.78 (2H, m), 3.83 (3H, s), 3.79(3H, s), 1.80–1.50(4H, m), 0.93– 0.85 (6H, m).

REFERENCE EXAMPLE 22

(E)-8-(2,3-Dimethoxystyryl)-7-methyl-1,3-dipropylxanthine (Compound 29)

Substantially the same procedure as in Reference Example 1 was repeated using 1.5 g (3.77 mmol) of Compound 28 obtained in Reference Example 21 in place of Compound B. Then, the resultant crude crystals were recrystallized from toluene/cyclohexane to give 1.22 g (yield 79%) of Compound 29 as pale brown needles.

Melting Point: 163.5°–163.7° C.; Elemental Analysis: $C_{22}H_{28}N_4O_4$, Calcd. (%): C, 64.06; H, 6.84; N, 13.58; Found (%): C, 64.03; H, 7.12; N, 13.42; IR (KBr) $v_{max}$ (cm$^{-1}$): 1695, 1657, 1272; NMR (DMSO-d$_6$; 270 MHz)δ(ppm): 7.88(1H, d, J=15.8 Hz), 7.50(1H, dd, J=1.7, 7.6 Hz), 7.32 (1H, d, J=15.8 Hz), 7.17–7.06 (2H, m), 4.02 (3H, s), 4.02–3.98 (2H, m), 3.86–3.81 (2H, m), 3.84 (3H, s), 3.79 (3H, s), 1.80– 1.65 (2H, m), 1.65–1.50 (2H, m), 0.93–0.84 (6H, m).

REFERENCE EXAMPLE 23

(E)-8-(3,4-Dimethylstyryl)-1,3-dipropylxanthine (Compound 30)

Substantially the same procedure as in Reference Example 1 was repeated using 5.90 g (26.0 mmol) of 5,6-diamino-1,3-dipropyluracil and 5.5 g (31.3 mmol) of 3,4-dimethylcinnamic acid. Then, the resultant crude crystals were recrystallized from dioxane/water to give 7.70 g (yield of Compound 30 as a white powder.

Melting Point: 252.7°–254.0° C.; Elemental Analysis: $C_{21}H_{26}N_4O_2$, Calcd. (%): C, 68.83; H, 7.15; N, 15.29; Found (%): C, 68.43; H, 7.22; N, 15.22; IR (KBr) $v_{max}$ (cm$^{-1}$): 1700, 1648, 1490; NMR (DMSO-d$_6$; 270 MHz)δ(ppm): 7.40(1H, d, J=16.2 Hz), 7.37(1H, s), 7.29(1H, d, J=7.2 Hz), 7.14(1H, d, J=7.2 Hz), 6.95 (1H, d, J=16.2 Hz), 3.95 (2H, t, J=7.2 Hz), 3.83 (2H, t, J=7.4 Hz), 2.25 (3H, s), 2.23 (3H, s), 1.80–1.55(4H, m), 1.00–0.90(6H, m).

REFERENCE EXAMPLE 24

(E)-8-(3,4-Dimethylstyryl)-7-methyl-1,3-dipropylxanthine (Compound 31)

Substantially the same procedure as in Reference Example 1 was repeated using 6.50 g (17.8 mmol) of Compound obtained in Reference Example 23 in place of Compound B. Then, the resultant crude crystals were recrystallized from ethanol/water to give 5.62 g (yield 83%) of Compound 31 as white needles.

Melting Point: 169.3°–170.3° C.; Elemental Analysis: $C_{22}H_{28}N_4O_2$, Calcd. (%): C, 69.45; H, 7.42; N, 14.72; Found (%): C, 69.33; H, 7.42; N, 14.86; IR (KBr) $v_{max}$ (cm$^{-1}$): 1693, 1656; NMR (DMSO-d$_6$; 270 MHz)δ(ppm): 7.59(1H, d, J=15.8 Hz), 7.58(1H, s), 7.49(1H, d, J=7.6 Hz), 7.26(1H, d, J=15.8 Hz), 7.19(1H, d, J=7.6 Hz), 4.02(3H, s), 4.05–3.90(2H, m), 3.84(2H, t, J=7.4 Hz), 2.27(3H, s), 2.25(3H, s), 1.85–1.50(4H, m), 1.00–0.85(6H, m).

REFERENCE EXAMPLE 25

(E)-8-(3,5-Dimethoxystyryl)-1,3-dipropylxanthine (Compound 32)

Substantially the same procedure as in Reference Example 1 was repeated using 3.95 g (17.5 mmol) of 5,6-diamino-1,3-dipropyluracil and 4.0 g (19.2 mmol) of 3,5-dimethoxycinnamic acid. Then, the resultant crude crystals were recrystallized from dimethylformamide/water to give 3.78 g (yield 54%) of Compound 32 as a white powder.

Melting Point: 248.7°–250.3° C.; Elemental Analysis: $C_{21}H_{26}N_4O_4$, Calcd. (%): C, 63.30; H, 6.58; N, 14.06; Found (%): C, 63.02; H, 6.71; N, 14.06; IR (KBr) $v_{max}$ (cm$^{-1}$): 1687, 1631, 1588, 1494; NMR (DMSO-d$_6$; 270 MHz)δ(ppm): 7.56(1H, d, J=16.6 Hz), 7.08 (1H, d, J=16.6 Hz), 6.78 (2H, d, J=2.0 Hz), 6.50 (1H, t, J=2.0 Hz), 3.98(2H, t, J=7.3 Hz), 3.85(2H, t, J=7.3 Hz), 3.79(6H, s), 1.80–1.50(4H, m), 0.92– 0.84 (6H, m).

REFERENCE EXAMPLE 26

(E)-8-(3,5-Dimethoxystyryl)-7-methyl-1,3-dipropylxanthine (Compound 33)

Substantially the same procedure as in Reference Example 1 was repeated using 3.23 g (8.27 mmol) of Compound 32 obtained in Reference Example 25 in place of Compound B. Then, the resultant crude crystals were recrystallized from acetonitrile to give 2.96 g (yield 87%) of Compound 33 as white needles.

Melting Point: 178.0°–178.2° C.; Elemental Analysis: $C_{22}H_{28}N_4O_4$, Calcd. (%): C, 64.06; H, 6.84; N, 13.58; Found (%): C, 63.87; H, 7.11; N, 13.66; IR (KBr) $v_{max}$ (cm$^{-1}$): 1692, 1657, 1592; NMR (DMSO-d$_6$; 270 MHz)δ(ppm): 7.59 (1H, d, J=15.9 Hz), 7.35 (1H, d, J=15.9

Hz), 6.98 (2H, d, J=2.9 Hz), 6.51 (1H, t, J=2.9 Hz), 4.04 (3H, s), 4.10–3.95 (2H, m), 3.90–3.75 (2H, m), 3.80(6H, s), 1.80–1.50(4H, m), 1.00–0.80 (6H, m).

REFERENCE EXAMPLE 27

(E)-8-(3-Nitrostyryl)-1,3-dipropylxanthine (Compound 34)

Substantially the same procedure as in Reference Example 1 was repeated using 4.0 g (17.7 mmol) of 5,6-diamino-1,3-dipropyluracil and 3.8 g (19.5 mmol) of 3-nitrocinnamic acid. Then, the resultant crude crystals were recrystallized from toluene to give 3.86 g (yield 57%) of Compound 34 as pale yellow needles.

Melting Point: 256.5°–256.8° C.; Elemental Analysis: $C_{19}H_{21}N_5O_4 \cdot 0.25C_6H_5CH_3$, Calcd. (%): C, 61.32; H, 5.70; N, 17.23; Found (%): C, 61.64; H, 5.94; N, 17.29; IR (KBr) $v_{max}$ (cm$^{-1}$): 1701, 1649, 1529, 1355; NMR (DMSO-d$_6$; 270 MHz)δ(ppm): 8.42 (1H, s), 8.19 (1H, d, J=8.0 Hz), 8.12 (1H, d, J=7.6 Hz), 7.80–7.65 (2H, m), 7.25 (1H, d, J=16.5 Hz), 4.00(2H, t, J=7.2 Hz), 3.86 (2H, t, J=7.3 Hz), 1.80–1.55 (4H, m), 1.00– 0.80 (6H, m).

REFERENCE EXAMPLE 28

(E)-7-Methyl-8-(3-nitrostyryl)-1,3-dipropylxanthine (Compound 35)

Substantially the same procedure as in Reference Example 1 was repeated using 3.20 g (8.36 mmol) of Compound 34 obtained in Reference Example 27 in place of Compound B. Then, the resultant crude crystals were recrystallized from toluene/cyclohexane to give 2.41 g (yield 73%) of Compound 35 as yellow needles.

Melting Point: 218.2°–218.4° C.; Elemental Analysis: $C_{20}H_{23}N_5O_4$, Calcd. (%): C, 60.44; H, 5.83; N, 17.62; Found (%): C, 59.94; H, 5.97; N, 17.43; IR (KBr) $v_{max}$ (cm$^{-1}$): 1699, 1662, 1521; NMR (DMSO-d$_6$; 270 MHz)δ(ppm): 8.70 (1H, m), 8.24 (1H, d, J=7.9 Hz), 8.19 (1H, dd, J=1.6, 7.6 Hz), 7.78 (1H, d, J=15.9 Hz), 7.71(1H, t, J=7.9 Hz), 7.61(1H, d, J=15.9 Hz), 4.08(3H, s), 4.01(2H, t, J=7.3 Hz), 3.85 (2H, t, J=7.3 Hz), 1.85–1.55(4H, m), 0.91(3H, t, J=7.5 Hz), 0.87(3H, t, J=7.4 Hz).

REFERENCE EXAMPLE 29

(E)-8-(3-Fluorostyryl)-1,3-dipropylxanthine (Compound 36)

Substantially the same procedure as in Reference Example 1 was repeated using 3.95 g (17.5 mmol) of 5,6-diamino-1,3-dipropyluracil and 3.19 g (19.2 mmol) of 3-fluorocinnamic acid. Then, the resultant crude crystals were recrystallized from dimethylformamide/water to give 4.67 g (yield 75%) of Compound 36 as a pale yellow powder.

Melting Point: 265.0°–265.9° C.; Elemental Analysis: $C_{19}H_{21}N_4O_2F$, Calcd. (%): C, 64.03; H, 5.94; N, 15.72; Found (%): C, 64.02; H, 5.96; N, 15.46; IR (KBr) $v_{max}$ (cm$^{-1}$): 1701, 1646; NMR (DMSO-d$_6$; 270 MHz)δ(ppm): 7.63(1H, d, J=16.3 Hz), 7.53–7.41 (3H, m), 7.23–7.15 (1H, m), 7.12 (1H, d, J=16.3 Hz), 3.99 (2H, t, J=7.0 Hz), 3.86 (2H, t, J=7.3 Hz), 1.80–1.50(4H, m), 0.93–0.85(6H, m).

REFERENCE EXAMPLE 30

(E)-8-(3-Fluorostyryl)-7-methyl-1,3-dipropylxanthine (Compound 37)

Substantially the same procedure as in Reference Example 1 was repeated using 2.92 g (8.19 mmol) of Compound 36 obtained in Reference Example 29 in place of Compound B. Then, the resultant crude crystals were recrystallized from toluene/cyclohexane to give 2.67 g (yield 88%) of Compound 37 as pale yellow needles.

Melting Point: 161.9°–162.0° C.; Elemental Analysis: $C_{20}H_{23}N_4O_2F$, Calcd. (%): C, 64.85; H, 6.26; N, 15.12; Found (%): C, 64.61; H, 6.40; N, 14.86; IR (KBr) $v_{max}$ (cm$^{-1}$): 1693, 1656, 1544; NMR (DMSO-d$_6$; 270 MHz)δ(ppm): 7.80–7.60(3H, m), 7.50– 7.38(2H, m), 7.19(1H, dt, J=2.3, 8.3 Hz), 4.04 (3H, s), 4.00 (2H, t, J=7.3 Hz), 3.84 (2H, t, J=7.5 Hz), 1.80–1.55 (4H, m), 1.00–0.80 (6H, m).

REFERENCE EXAMPLE 31

(E)-8-(3-Chlorostyryl)-1,3-dipropylxanthine (Compound 38)

Substantially the same procedure as in Reference Example 1 was repeated using 3.95 g (17.5 mmol) of 5,6-diamino-1,3-dipropyluracil and 3.51 g (19.2 mmol) of 3-chlorocinnamic acid. Then, the resultant crude crystals were recrystallized from dimethylformamide/water to give 4.44 g (yield 67%) of Compound 38 as pale yellow crystals.

Melting Point: 258.9°–259.4° C.; Elemental Analysis: $C_{19}H_{21}N_4O_2Cl$, Calcd. (%): C, 61.21; H, 5.68; N, 15.03; Found (%): C, 61.52; H, 5.73; N, 14.79; IR (KBr) $v_{max}$ (cm$^{-1}$): 1700, 1644, 1588, 1494; NMR (DMSO-d$_6$; 270 MHz)δ(ppm): 13.7 (1H, brs), 7.71– 7.52 (3H, m), 7.48–7.39 (2H, m), 7.12 (1H, d, J=16.3 Hz), 3.99 (2H, t, J=7.0 Hz), 3.86 (2H, t, J=7.0 Hz), 1.80–1.50(4H, m), 0.93–0.84(6H, m).

REFERENCE EXAMPLE 32

(E)-8-(3-Chlorostyryl)-7-methyl-1,3-dipropylxanthine (Compound 39)

Substantially the same procedure as in Reference Example 1 was repeated using 2.85 g (7.66 mmol) of Compound 38 obtained in Reference Example 31 in place of Compound B. Then, the resultant crude crystals were recrystallized from ethanol to give 2.69 g (yield 91%) of Compound 39 as white needles.

Melting Point: 167.7°–167.9° C.; Elemental Analysis: $C_{20}H_{23}N_4O_2Cl$, Calcd. (%): C, 62.09; H, 5.99; N, 14.48; Found (%): C, 62.00; H, 6.08; N, 14.27; IR (KBr) $v_{max}$ (cm$^{-1}$): 1691, 1657, 1543; NMR (DMSO-d$_6$; 270 MHz)δ(ppm): 7.99(1H, s), 7.72 (1H, d, J=6.6 Hz), 7.63(1H, d, J=15.8 Hz), 7.50– 7.30 (3H, m), 4.05(3H, s), 4.00(2H, t, J=7.5 Hz), 3.84 (2H, t, J=7.4 Hz), 1.80–1.55(4H, m), 1.00–0.80 (6H, m).

REFERENCE EXAMPLE 33

(E)-8-(2-Chlorostyryl)-1,3-dipropylxanthine (Compound 40)

Substantially the same procedure as in Reference Example 1 was repeated using 3.00 g (13.3 mmol) of 5,6-diamino-1,3-dipropyluracil and 2.67 g (14.6 mmol) of 2-chlorocinnamic acid. Then, the resultant crude crystals were recrystallized from toluene to give 3.72 g (yield 82%) of Compound 40 as white needles.

Melting Point: 269.4°–269.9° C.; Elemental Analysis: $C_{19}H_{21}N_4O_2Cl$, Calcd. (%): C, 61.21; H, 5.68; N, 15.03; Found (%): C, 60.94; H, 5.69; N, 14.68; IR (KBr) $v_{max}$ (cm$^{-1}$): 1695, 1645, 1493; NMR (DMSO-d$_6$; 270 MHz)δ(ppm): 8.00–7.80 (2H, m), 7.55– 7.50(1H, m), 7.45–7.37(2H, m), 7.12(1H, d, J=16.5 Hz), 3.99 (2H, t, J=7.3 Hz), 3.86 (2H, t, J=7.4 Hz), 1.80–1.55(4H, m), 1.00–0.80(6H, m).

REFERENCE EXAMPLE 34

(E)-8-(2-Chlorostyryl)-7-methyl-1,3-dipropylxanthine (Compound 41)

Substantially the same procedure as in Reference Example 1 was repeated using 2.37 g (6.37 mmol) of Compound 40 obtained in Reference Example 33 in place of Compound B. Then, the resultant crude crystals were recrystallized from ethanol/water to give 1.88 g (yield 77%) of Compound 41 as yellow needles.

Melting Point: 159.0°–159.9° C.; Elemental Analysis: $C_{20}H_{23}N_4O_2Cl$, Calcd. (%): C, 62.09; H, 5.99; N, 14.48; Found (%): C, 61.75; H, 6.14; N, 14.45; IR (KBr) $v_{max}$ (cm$^{-1}$): 1696, 1650, 1544; NMR (DMSO-d$_6$; 270 MHz)δ(ppm): 8.10(1H, dd, J=2.3, 7.3 Hz), 7.97(1H, d, J=15.5 Hz), 7.55–7.50(1H, m), 7.46–7.35(3H, m), 4.05(3H, s), 4.00(2H, t, J=7.3 Hz), 3.84(2H, t, J=7.3 Hz), 1.80–1.55(4H, m), 1.00–0.80 (6H, m).

REFERENCE EXAMPLE 35

(E)-8-(2-Fluorostyryl)-1,3-dipropylxanthine (Compound 42)

Substantially the same procedure as in Reference Example 1 was repeated using 3.00 g (13.3 mmol) of 5,6-diamino-1,3-dipropyluracil and 2.43 g (14.6 mmol) of 2-fluorocinnamic acid. Then, the resultant crude crystals were recrystallized from dioxane/water to give 3.23 g (yield 68%) of Compound 42 as white needles.

Melting Point: 258.8°–259.2° C.; Elemental Analysis: $C_{19}H_{21}N_4O_2F$, Calcd. (%): C, 64.03; H, 5.94; N, 15.72; Found (%): C, 64.01; H, 6.11; N, 15.52; IR (KBr) $v_{max}$ (cm$^{-1}$): 1702, 1648; NMR (DMSO-d$_6$; 270 MHz)δ(ppm): 7.85–7.77(2H, m), 7.46– 7.32(1H, m), 7.29–7.23(2H, m), 7.16(1H, d, J=16.5 Hz), 3.99 (2H, t, J=7.1 Hz), 3.86 (2H, t, J=7.3 Hz), 1.80–1.55(4H, m), 1.00–0.80(6H, m).

REFERENCE EXAMPLE 36

(E)-8-(2 -Fluorostyryl)-7 -methyl-1,3-dipropylxanthine (Compound 43)

Substantially the same procedure as in Reference Example 1 was repeated using 3.50 g (9.83 mmol) of Compound 42 obtained in Reference Example 35 in place of Compound B. Then, the resultant crude crystals were recrystallized from ethanol/water to give 1.23 g (yield 34%) of Compound 43 as white needles.

Melting Point: 155.5°–155.9° C.; Elemental Analysis: $C_{20}H_{23}N_4O_2F$, Calcd. (%): C, 64.85; H, 6.26; N, 15.12; Found (%): C, 65.00; H, 6.44; N, 15.34; IR (KBr) $v_{max}$ (cm$^{-1}$): 1694, 1660; NMR (DMSO-d$_6$; 270 MHz)δ(ppm): 8.02(1H, t, J=8.3 Hz), 7.75(1H, d, J=15.5 Hz), 7.47–7.40(2H, m), 7.40– 7.25(2H, m), 4.03(3H, s), 4.00(2H, t, J=7.4 Hz), 3.84 (2H, t, J=7.4 Hz), 1.80–1.55(4H, m), 1.00–0.80 (6H, m).

REFERENCE EXAMPLE 37

(E)-8-(4-Methoxy-2,5-dimethylstyryl)-1,3-dipropylxanthine (Compound 44)

Substantially the same procedure as in Reference Example 1 was repeated using 2.5 g (11.1 mmol) of 5,6-diamino-1,3-dipropyluracil and 2.51 g (12.17 mmol) of 4-methoxy-2,5-dimethylcinnamic acid. Then, the resultant crude crystals were recrystallized from ethanol/water to give 1.98 g (yield 45%) of Compound 44 as white crystals.

Melting Point: 268.0–269.2° C.; Elemental Analysis: $C_{22}H_{28}N_4O_3$, Calcd. (%): C, 66.65; H, 7.11; N, 14.13; Found (%): C, 66.82; H, 7.34; N, 14.14; IR (KBr) $v_{max}$ (cm$^{-1}$): 1694, 1644, 1506, 1261; NMR (DMSO-d$_6$; 270 MHz)δ(ppm): 12.95(1H, brs), 7.95 (1H, d, J=15.8 Hz), 7.42 (1H, s), 6.89 (1H, d, J=15.8 Hz), 6.66(1H, s), 4.19–4.07 (4H, m), 3.86(3H, s), 2.48 (3H, s), 2.21 (3H, s), 1.91–1.74 (4H, m), 1.02 (3H, t, J=6.9 Hz), 0.93 (3H, t, J=6.9 Hz).

REFERENCE EXAMPLE 38

(E)-8-(4-Methoxy-2,5-dimethylstyryl)-7-methyl-1,3-dipropylxanthine (Compound 45)

Substantially the same procedure as in Reference Example 1 was repeated using 973 mg (2.45 mmol) of Compound 44 obtained in Reference Example 37 in place of Compound B. Then, the resultant crude crystals were recrystallized from 2-propanol/water to give 966 mg (yield 96%) of Compound 45 as pale yellow needles.

Melting Point: 245.3°–246.3° C.; Elemental Analysis: $C_{23}H_{30}N_4O_3$, Calcd. (%): C, 67.30; H, 7.36; N, 13.65; Found (%): C, 67.37; H, 7.51; N, 13.69; IR (KBr) $v_{max}$ (cm$^{-1}$): 1690, 1655, 1508, 1261; NMR (DMSO-d$_6$; 270 MHz)δ(ppm): 7.96(1H, d, J=15.8 Hz), 7.41(1H, s), 6.70(1H, d, J=15.8 Hz), 6.66(1H, s), 4.14–4.09 (2H, m), 4.05 (3H, s), 4.01–3.95 (2H, m), 2.48(3H, s), 2.22(3H, s), 1.91–1.77(2H, m), 1.74

1.63 (2H, m), 1.03–0.94 (6H, m).

REFERENCE EXAMPLE 39

(Z)-8-(3,4-Dimethoxystyryl)-7-methyl-1,3-dipropylxanthine (Compound 46) (an about 6:4 Mixture of Compound 46 and Compound 1)

Compound 1 (2.00 g, 4.85 mmol) obtained in Reference Example 1 was dissolved in 180 ml of chloroform, and the solution was irradiated with sunlight for 24 hours. After careful concentration of the reaction mixture, methanol was added thereto and deposited crystals were collected by filtration. The crystals were dried under reduced pressure to give 1.72 g (yield 86%) of a mixture of Compound 46 and Compound 1 as a pale yellow powder (The ratio of Compound 46 to Compound 1 was about 6:4 by NMR analysis).

Melting Point: 115.2°–119.4° C.; Elemental Analysis: $C_{22}H_{28}N_4O_4$, Calcd. (%): C, 64.06; H, 6.84; N, 13.58; Found (%): C, 64.02; H, 6.82; N, 13.46; IR (KBr) $v_{max}$ (cm$^{-1}$): 1695, 1656, 1521; NMR (DMSO-d$_6$; 270 MHz)δ(ppm): 7.60 (1×4/10H, d, J=15.8 Hz), 7.40(1×4/10H, d, J=2.0 Hz), 7.32–7.17 (2×4/10H+2×6/10H, m), 6.99 (1×4/10H, d, J=8.4 Hz), 6.94 (1×6/10H, d, J=12.7 Hz), 6.92 (1×6/10H, d, J=8.2 Hz), 6.39(1×6/10H, d, J=12.7 Hz), 4.02 (3×4/10H, s), 4.10–3.80(4H, m), 3.85(3×4/10H, s), 3.80

(3×4/10H, s), 3.77 (6×6/10H, s), 3.64 (3×6/10H, s), 1.80–1.55(4H, m), 1.00–0.85(6H, m).

REFERENCE EXAMPLE 40

(E)-8-(4-Ethoxystyryl)-1,3-dipropylxanthine (Compound 47)

Substantially the same procedure as in Reference Example 1 was repeated using 3.0 g (13.3 mmol) of 5,6-diamino-1,3-dipropyluracil and 2.80 g (14.6 mmol) of 4-ethoxycinnamic acid. Then, the resultant crude crystals were recrystallized from dioxane to give 3.57 g (yield 70%) of Compound 47 as pale yellow needles.

Melting Point: 261.6°–262.0° C.; Elemental Analysis: $C_{21}H_{26}N_4O_3$, Calcd. (%): C, 65.96; H, 6.85; N, 14.65; Found (%): C, 65.93; H, 7.13; N, 14.65; IR (KBr) $\nu_{max}$ ($cm^{-1}$): 1701, 1635, 1516, 1261; (DMSO-$d_6$; 270 MHz)δ(ppm): 13.37 (1H, brs), 7.59 (1H, d, J=16.5 Hz), 7.55 (2H, d, J=8.6 Hz), 6.96 (2H, d, J=8.6 Hz), 6.88 (1H, d, J=16.5 Hz), 4.07 (2H, q, J=6.9 Hz), 3.99 (2H, t, J=7.3 Hz), 3.86(2H, t, J=7.3 Hz), 1.73 (2H, m), 1.58(2H, m), 1.34(3H, t, J=6.9 Hz), 0.90(3H, t, J=7.3 Hz), 0.87 (3H, t, J=7.3 Hz).

REFERENCE EXAMPLE 41

(E)-8-(4-Ethoxystyryl)-7-methyl-1,3-dipropylxanthine (Compound 48)

Substantially the same procedure as in Reference Example 1 was repeated using 2.0 g (5.23 mmol) of Compound 47 obtained in Reference Example 40 in place of Compound B. Then, the resultant crude crystals were recrystallized from hexane/ethyl acetate to give 1.72 g (yield 83%) of Compound as pale green needles.

Melting Point: 174.7°–175.0° C.; Elemental Analysis: $C_{22}H_{28}N_4O_3$, Calcd. (%): C, 66.65; H, 7.11; N, 14.13; Found (%): C, 66.60; H, 7.20; N, 14.27; IR (KBr) $\nu_{max}$ ($cm^{-1}$): 1702, 1660, 1515, 1252; NMR (CDCl$_3$; 270 MHz)δ(ppm): 7.74(1H, d, J=15.8 Hz), 7.52(2H, d, J=8.6 Hz), 6.92(2H, d, J=8.6 Hz), 6.76 (1H, d, J=15.8 Hz), 4.09(2H, t, J=7.6 Hz), 4.08(2H, q, J=6.9 Hz), 4.04 (3H, s), 3.99 (2H, t, J=7.6 Hz), 1.44(3H, t, J=6.9 Hz), 1.00(3H, t, J=7.6 Hz), 0.97 (3H, t, J=7.6 Hz).

REFERENCE EXAMPLE 42

(E)-8-(4-Propoxystyryl)-1,3-dipropylxanthine (Compound 49)

Substantially the same procedure as in Reference Example 1 was repeated using 3.0 g (13.3 mmol) of 5,6-diamino-1,3-dipropyluracil and 3.01 g (14.6 mmol) of 4-propoxycinnamic acid. Then, the resultant crude crystals were recrystallized from dioxane/water to give 1.71 g (yield 33%) of Compound 49 as pale brown needles.

Melting Point: 248.3°–248.7° C.; Elemental Analysis: $C_{22}H_{28}N_4O_3$, Calcd. (%): C, 66.65; H, 7.11; N, 14.13; Found (%): C, 66.50; H, 7.48; N, 14.25; IR (KBr) $\nu_{max}$ ($cm^{-1}$): 1694, 1649, 1514, 1253; NMR (DMSO-$d_6$; 270 MHz)δ(ppm): 13.34 (1H, brs), 7.58 (1H, d, J=16.5 Hz), 7.55 (2H, d, J=8.6 Hz), 6.99 (2H, d, J=8.6 Hz), 6.88 (1H, d, J=16.5 Hz), 4.01–3.95(4H, m), 3.86 (2H, t, J=7.3 Hz), 1.78–1.70 (4H, m), 1.62–1.54(2H, m), 0.98(3H, t, J=7.3 Hz), 0.90 (3H, t, J=7.6 Hz), 0.87 (3H, t, J=7.6 Hz).

REFERENCE EXAMPLE 43

(E)-7-Methyl-8-(4-propoxystyryl)-1,3-dipropylxanthine (Compound 50)

Substantially the same procedure as in Reference Example 1 was repeated using 1.0 g (2.52 mmol) of Compound 49 obtained in Reference Example 42 in place of Compound B. Then, the resultant crude crystals were recrystallized from hexane/ethyl acetate to give 863 mg (yield 83%) of Compound as pale yellow needles.

Melting Point: 172.6°–173.5° C.; Elemental Analysis: $C_{23}H_{30}N_4O_3$, Calcd. (%): C, 67.30; H, 7.36; N, 13.65; Found (%): C, 67.15; H, 7.65; N, 13.58; IR (KBr) $\nu_{max}$ ($cm^{-1}$): 1699, 1658, 1514, 1252; NMR (CDCl$_3$; 270 MHz)δ(ppm): 7.74(1H, d, J=15.8 Hz), 7.52(2H, d, J=8.9 Hz), 6.92(2H, d, J=8.9 Hz), 6.76 (1H, d, J=15.8 Hz), 4.13–3.94(6H, m), 4.04(3H, s), 1.90–1.62 (6H, m), 1.08–0.94 (9H, m).

REFERENCE EXAMPLE 44

(E)-8-(4-Butoxystyryl)-1,3-dipropylxanthine (Compound 51)

Substantially the same procedure as in Reference Example 1 was repeated using 3.0 g (13.3 mmol) of 5,6-diamino-1,3-dipropyluracil and 3.21 g (14.6 mmol) of 4-butoxycinnamic acid. Then, the resultant crude crystals were recrystallized from dioxane/water to give 3.47 g (yield 64%) of Compound 51 as white needles.

Melting Point: 237.3°–238.9° C.; Elemental Analysis: $C_{23}H_{30}N_4O_3$, Calcd. (%) C, 67.30; H, 7.36; N, 13.65; Found (%): C, 67.39; H, 7.45; N, 13.59; IR (KBr) $\nu_{max}$ ($cm^{-1}$): 1697, 1644, 1514, 1257; NMR (DMSO-$d_6$; 270 MHz)δ(ppm): 13.37(1H, brs), 7.58 (1H, d, J=16.2 Hz), 7.55(2H, d, J=8.6 Hz), 6.97(2H, d, J=8.6 Hz), 6.88(1H, d, J=16.2 Hz), 4.04–3.96(4H, m), 3.86(2H, t, J=7.3 Hz), 1.80–1.37(8H, m), 0.97– 0.84 (9H, m).

REFERENCE EXAMPLE 45

(E)-8-(4-Butoxystyryl)-7-methyl-1,3-dipropylxanthine (Compound 52)

Substantially the same procedure as in Reference Example 1 was repeated using 2.0 g (4.87 mmol) of Compound obtained in Reference Example 44 in place of Compound B. Then, the resultant crude crystals were recrystallized from hexane/ethyl acetate to give 1.56 g (yield 75%) of Compound 52 as pale green needles.

Melting Point: 134.8°–135.6° C.; Elemental Analysis: $C_{24}H_{32}N_4O_3$, Calcd. (%): C, 67.90; H, 7.59; N, 13.20; Found (%): C, 68.22; H, 7.88; N, 13.49; IR (KBr) $\nu_{max}$ ($cm^{-1}$): 1696, 1651, 1513, 1247; NMR (CDCl$_3$; 270 MHz)δ(ppm): 7.74(1H, d, J=15.5 Hz), 7.52(2H, d, J=8.6 Hz), 6.92(2H, d, J=8.6 Hz), 6.76 (1H, d, J=15.5 Hz), 4.13–3.95 (6H, m), 4.04 (3H, s), 1.88–1.44(8H, m), 1.03–0.94(9H, m).

REFERENCE EXAMPLE 46

(E)-8-(3,4-Dihydroxystyryl)-7-methyl-1,3-dipropylxanthine (Compound 53)

Compound 1 (770 mg, 1.87 mmol) obtained in Reference Example 1 was dissolved in 15 ml of methylene chloride. To the solution was added 5.6 ml (5.6 mmol) of boron tribromide (1.0M methylene chloride solution) under ice cooling in argon atmosphere, and the mixture was stirred overnight at room temperature. Methanol was added thereto and the mixture was separated with chloroform-an aqueous solution of sodium bicarbonate. The organic layer was washed with a saturated aqueous solution of sodium chloride and dried over anhydrous sodium sulfate, followed by evaporation under reduced pressure. The residue was purified by silica gel column chromatography to give 550 mg (yield 77%) of Compound 53 as a yellow solid, which was then triturated with ether to give a yellow powder.

Melting Point: 250.1°–251.4° C.; Elemental Analysis: $C_{20}H_{24}N_4O_4$, Calcd. (%): C, 62.49; H, 6.29; N, 14.57; Found (%): C, 62.27; H, 6.48; N, 14.74; IR (KBr) $v_{max}$ (cm$^{-1}$): 1680, 1640, 1543, 1306; NMR (DMSO-d$_6$; 270 MHz)δ(ppm): 9.31(1H, brs), 8.95(1H, brs), 7.49(1H, d, J=15.8 Hz), 7.15(1H, d, J=2.0 Hz), 7.04(1H, dd, J=7.9, 2.0 Hz), 6.98(1H, d, J=15.8 Hz), 6.78(1H, d, J=7.9 Hz), 3.99(2H, t, J=7.6 Hz), 3.98 (3H, s), 3.84(2H, t, J=7.4 Hz), 1.73(2H, m), 1.57 (2H, m), 0.90(3H, t, J=7.4 Hz), 0.87(3H, t, J=7.4 Hz).

REFERENCE EXAMPLE 47

(E)-8-(3,4-Diethoxystyryl)-7-methyl-1,3-dipropylxanthine (Compound 54)

Compound 53 (390 mg, 1.01 mmol) obtained in Reference Example 46 was dissolved in 10 ml of dimethylformamide. To the solution were added 0.20 ml (2.50 mmol) of ethyl iodide and 420 mg (3.04 mmol) of potassium carbonate, and the mixture was stirred overnight at room temperature. Water was added thereto to dissolve potassium carbonate and deposited crystals were collected by filtration. The collected crude crystals were recrystallized from hexane/ethyl acetate to give 237 mg (yield 53%) of Compound 54 as pale yellow needles.

Melting Point: 173.8°–174.0° C.; Elemental Analysis: $C_{24}H_{32}N_4O_4$, Calcd. (%): C, 65.44; H, 7.32; N, 12.72; Found (%): C, 65.42; H, 7.48; N, 12.62; IR (KBr) $v_{max}$ (cm$^{-1}$) 1694, 1653, 1508, 1268; NMR (CDCl$_3$; 270 MHz)δ(ppm): 7.71(1H, d, J=15.5 Hz), 7.15(1H, dd, J=8.3, 2.0 Hz), 7.10(1H, d, J=2.0 Hz), 6.89(1H, d, J=8.3 Hz), 6.74(1H, d, J=15.5 Hz), 4.16 (2H, q, J=6.9 Hz), 4.14 (2H, q, J=6.9 Hz), 4.08–3.95 (4H, m), 4.05(3H, s), 1.91–1.76(2H, m), 1.76–1.62 (2H, m), 1.49(3H, t, J=6.9 Hz), 1.48(3H, t, J=6.9 Hz), 1.00 (3H, t, J=7.6 Hz), 0.97 (3H, t, J=7.6 Hz).

REFERENCE EXAMPLE 48

(E)-8-(3-Bromo-4-methoxystyryl)-1,3-dipropylxanthine (Compound 55)

Substantially the same procedure as in Reference Example 1 was repeated using 3.0 g (13.3 mmol) of 5,6-diamino-1,3-dipropyluracil and 3.75 g (14.6 mmol) of 3-bromo-4-methoxycinnamic acid. Then, the resultant crude crystals were recrystallized from dioxane to give 3.43 g (yield 58%) of Compound 55 as yellow needles.

Melting Point: 279.8°–280.6° C.; Elemental Analysis: $C_{20}H_{23}N_4O_3Br$, Calcd. (%): C, 53.70; H, 5.18; N, 12.52; Found (%): C, 53.77; H, 5.20; N, 12.49; IR (KBr) $v_{max}$ (cm$^{-1}$): 1685, 1633, 1599, 1503, 1279; NMR (DMSO-d$_6$; 270 MHz)δ(ppm): 13.42(1H, brs), 7.85 (1H, d, J=2.0 Hz), 7.61(1H, dd, J=8.4, 2.0 Hz), 7.55 (1H, d, J=16.3 Hz), 7.15 (1H, d, J=8.4 Hz), 6.94 (1H, d, J=16.3 Hz), 3.98 (2H, t, J=7.4 Hz), 3.89 (3H, s), 3.86 (2H, t, J=7.4 Hz), 1.80–1.52 (4H, m), 0.89 (6H, q, J=7.4 Hz).

REFERENCE EXAMPLE 49

(E)-8-(3-Bromo-4-methoxystyryl)-7-methyl-3-dipropylxanthine (Compound 56)

Substantially the same procedure as in Reference Example 1 was repeated using 750 mg (1.68 mmol) of Compound 55 obtained in Reference Example 48 in place of Compound B. Then, the resultant crude crystals were recrystallized from hexane/ethyl acetate to give 588 mg (yield 76%) of Compound 56 as pale yellow needles.

Melting Point: 209.4°–210.8° C.; Elemental Analysis: $C_{21}H_{25}N_4O_3Br$, Calcd. (%): C, 54.67; H, 5.46; N, 12.14; Found (%): C, 54.47; H, 5.51; N, 11.91; IR (KBr) $v_{max}$ (cm$^{-1}$): 1693, 1656, 1542, 1500, 1264; NMR (CDCl$_3$; 270 MHz)δ(ppm): 7.83(1H, d, J=2.0 Hz), 7.68(1H, d, J=15.8 Hz), 7.48(1H, dd, J=8.4, 2.0 Hz), 6.92(1H, d, J=8.4 Hz), 6.78(1H, d, J=15.8 Hz), 4.13–4.07 (2H, m), 4.06 (3H, s), 4.01–3.97 (2H, m), 3.95 (3H, s), 1.90–1.65(4H, m), 1.00(3H, t, J=7.4 Hz), 0.97 (3H, t, J=7.4 Hz).

REFERENCE EXAMPLE 50

(E)-8-(2-Bromo-4,5-dimethoxystyryl)-1,3-dipropylxanthine (Compound 57)

Substantially the same procedure as in Reference Example 1 was repeated using 2.0 g (8.85 mmol) of 5,6-diamino-1,3-dipropyluracil and 2.80 g (9.75 mmol) of 2-bromo-4,5-dimethoxycinnamic acid. Then, the resultant crude crystals were recrystallized from dioxane to give 2.38 g (yield 56%) of Compound 57 as pale yellow needles.

Melting Point: 248.2°–249.5° C.; Elemental Analysis: $C_{21}H_{25}N_4O_4Br$, Calcd. (%): C, 52.84; H, 5.28; N, 11.74; Found (%): C, 52.73; H, 5.31; N, 11.45; IR (KBr) $v_{max}$ (cm$^{-1}$): 1697, 1643, 1506, 1263; NMR (DMSO-d$_6$; 270 MHz)δ(ppm): 13.75(1H, brs), 7.81 (1H, d, J=16.3 Hz), 7.39(1H, s), 7.20(1H, s), 7.09 (1H, d, J=16.3 Hz), 4.00–3.82 (4H, m), 3.86(3H, s), 3.82(3H, s), 1.76–1.54(4H, m), 0.92–0.85(6H, m).

REFERENCE EXAMPLE 51

(E)-8-(2-Bromo-4,5-dimethoxystyryl)-7-methyl-1,3-dipropylxanthine (Compound 58)

Substantially the same procedure as in Reference Example 1 was repeated using 800 mg (1.68 mmol) of Compound 57 obtained in Reference Example 50 in place of Compound B. Then, the resultant crude crystals were recrystallized from dioxane to give 766 mg (yield 93%) of Compound 58 as yellow needles.

Melting Point: 228.8°–229.4° C.; Elemental Analysis: $C_{22}H_{27}N_4O_4Br$, Calcd. (%): C, 53.78; H, 5.54; N, 11.40; Found (%): C, 53.76; H, 5.67; N, 11.16; IR (KBr) $v_{max}$ (cm$^{-1}$): 1688, 1650, 1509, 1266; NMR (CDCl$_3$; 270 MHz)δ(ppm): 8.01 (1H, d, J=15.8 Hz), 7.11(1H, s), 7.09(1H, s), 6.75(1H, d, J=15.8 Hz), 4.15–3.92 (4H, m), 4.08 (3H, s), 3.95(3H, s), 3.92 (3H, s), 1.91–1.77 (2H, m), 1.74–1.63 (2H, m), 1.03–0.94 (6H, m).

REFERENCE EXAMPLE 52

(E)-8-(3-Bromo-4,5-dimethoxystyryl)-1,3-dipropylxanthine (Compound 59)

Substantially the same procedure as in Reference Example 1 was repeated using 1.5 g (6.64 mmol) of 5,6-diamino-1,3-dipropyluracil and 2.10 g (7.31 mmol) of 3-bromo-4,5-dimethoxycinnamic acid. Then, the resultant crude crystals were recrystallized from dioxane/water to give 2.11 g (yield 67%) of Compound 59 as white needles.

Melting Point: 276.7°–277.5° C.; Elemental Analysis: $C_{21}H_{25}N_4O_4Br$, Calcd. (%): C, 52.84; H, 5.28; N, 11.74; Found (%): C, 52.72; H, 5.16; N, 11.56; IR (KBr) $v_{max}$ (cm$^{-1}$): 1701, 1650, 1562, 1498; NMR (DMSO-d$_6$; 270 MHz)δ(ppm): 13.44(1H, brs), 7.55 (1H, d, J=16.3 Hz), 7.39(1H, d, J=2.0 Hz), 7.36(1H, d, J=2.0 Hz), 7.07(1H, d, J=16.3 Hz), 3.99(2H, t, J=7.4 Hz), 3.91(3H, s), 3.86(2H, t, J=7.4 Hz), 3.78 (3H, s), 1.77–1.52(4H, m), 0.93–0.85(6H, m).

REFERENCE EXAMPLE 53

(E)-8-(3-Bromo-4,5-dimethoxystyryl)-7-methyl-1,3-dipropylxanthine (Compound 60)

Substantially the same procedure as in Reference Example 1 was repeated using 1.0 g (2.10 mmol) of Compound obtained in Reference Example 52 in place of Compound B. Then, the resultant crude crystals were recrystallized from hexane/ethyl acetate to give 952 mg (yield 93%) of Compound 60 as pale yellow needles.

Melting Point: 180.9°–181.6° C.; MS-EI m/e: 490, 492; IR (KBr) $v_{max}$ (cm$^{-1}$): 1691, 1648, 1542, 1493; NMR (CDCl$_3$; 270 MHz)δ(ppm): 7.68(1H, d, J=15.8 Hz), 7.42 (1H, d, J=2.0 Hz), 7.02 (1H, d, J=2.0 Hz), 6.80 (1H, d, J=15.8 Hz), 4.13–3.95 (4H, m), 4.08 (3H, s), 3.94 (3H, s), 3.90 (3H, s), 1.90–1.65 (4H, m), 1.01 (3H, t, J=7.4 Hz), 0.97(3H, t, J=7.4 Hz).

REFERENCE EXAMPLE 54

(E)-8-(3-Hydroxy-4-methoxystyryl)-7-methyl-1,3-dipropylxanthine (Compound 63)

Compound 53 (500 mg, 1.30 mmol) obtained in Reference Example 46 was dissolved in 10 ml of dimethylformamide. To the solution were added 0.40 ml (6.43 mmol) of methyl iodide and 400 mg (6.50 mmol) of lithium carbonate, and the mixture was stirred at 80° C. for 5 hours. Water was added thereto to dissolve lithium carbonate and deposited crystals were collected by filtration. The collected crude crystals were dissolved in chloroform, washed with a saturated aqueous solution of sodium chloride and dried over anhydrous sodium sulfate, followed by evaporation under reduced pressure. The residue was purified by silica gel column chromatography (eluent: chloroform) to give 162 mg (yield 31%) of Compound 63 as yellow grains.

Melting Point: 200.3°–203.6° C.; IR (KBr) $v_{max}$ (cm$^{-1}$): 1683, 1642, 1512, 1278; NMR (DMSO-d$_6$; 270 MHz)δ(ppm): 8.98 (1H, brs), 7.52 (1H, d, J=15.5 Hz), 7.22 (1H, d, J=2.0 Hz), 7.15 (1H, dd, J=8.3, 2.0 Hz), 7.06(1H, d, J=15.5 Hz), 6.96 (1H, d, J=8.3 Hz), 4.02–3.97 (2H, m), 4.00 (3H, s), 3.84–3.82 (2H, m), 3.82 (3H, s), 1.80–1.50 (4H, m), 0.90 (3H, t, J=7.3 Hz), 0.87(3H, t, J=7.3 Hz).

REFERENCE EXAMPLE 55

(E)-8-(2-Chloro-3,4-dimethoxystyryl)-1,3-diethylxanthine (Compound 112)

Substantially the same procedure as in Example 7 was repeated using 2.00 g (10.1 mmol) of 5,6-diamino-1,3-diethyluracil and 2.94 g (12.1 mmol) of 2-chloro-3,4-dimethoxycinnamic acid. Then, the resultant crude crystals were recrystallized from 2-propanol/water to give 2.19 g (yield 54%) of Compound 112 as pale yellow needles.

Melting Point: 278.0°–280.9° C.; Elemental Analysis: $C_{19}H_{21}ClN_4O_4$, Calcd. (%): C, 56.36; H, 5.22; N, 13.83; Found (%): C, 56.13; H, 5.21; N, 13.67; IR (KBr) $v_{max}$ (cm$^{-1}$): 1705, 1642, 1499; NMR (270 MHz; DMSO-d$_6$)δ(ppm): 7.88(1H, d, J=16.3 Hz), 7.64 (1H, d, J=8.9 Hz), 7.13 (1H, d, J=8.9 Hz), 7.00 J=7.1 Hz), 3.98–3.88 (1H, d, J=16.3 Hz), 4.06(2H, q, (2H, m), 3.88 (3H, s), 3.77 (3H, s), 1.26 (3H, t, J=7.1 Hz), 1.14 (3H, t, J=6.9 Hz).

REFERENCE EXAMPLE 56

(E)-8-(2-Chloro-3,4-dimethoxystyryl)-1,3-diethyl-7-methylxanthine (Compound 113)

Substantially the same procedure as in Example 8 was repeated using 1.80 g (4.45 mmol) of Compound 112 obtained in Reference Example 55 in place of Compound 64. Then, the resultant crude crystals were recrystallized from 2-propanol/water to give 1.20 g (yield 64%) of Compound 113 as yellow needles.

Melting Point: 204.6°–205.4° C.; Elemental Analysis: $C_{20}H_{23}ClN_4O_4$, Calcd. (%): C, 57.34; H, 5.53; N, 13.37; Found (%): C, 57.46; H, 5.67; N, 13.10; IR (KBr) $v_{max}$ (cm$^{-1}$): 1696, 1657, 1496, 1439, 1292; NMR (270 MHz; DMSO-d$_6$)δ(ppm): 7.92(1H, d, J=15.8 Hz), 7.86(1H, d, J=8.9 Hz), 7.29(1H, d, J=15.8 Hz), 7.16 (1H, d, J=8.9 Hz), 4.11–4.03 (2H, m), 4.03 (3H, s), 3.96–3.90(2H, m), 3.90(3H, s), 3.77(3H, s), 1.26 (3H, t, J=6.9 Hz), 1.13 (3H, t, J=6.9 Hz).

REFERENCE EXAMPLE 57

(E)-8-(2-Chloro-3,4-dimethoxystyryl)theophylline (Compound 114)

2-Chloro-3,4-dimethoxycinnamic acid (3.93 g, 16.2 mmol) was dissolved in 57 ml of pyridine. To the solution was added 1.26 ml (17.6 mmol) of thionyl chloride under ice cooling, and the mixture was stirred at 60° C. for 1.5 hours. Methylene chloride (58 ml) containing 2.50g (14.7 mmol) of 5,6-diamino-1,3-dimethyluracil was added dropwise to the solution under ice cooling, and the reaction solution was stirred at room temperature for further 40 minutes. The deposited crystals were collected by filtration and the obtained crude crystals were dissolved in a mixture of 68 ml of an aqueous 2N sodium hydroxide solution, 68 ml of dioxane, and 34 ml of water, followed by heating under reflux for 30 minutes. After cooling, the solution was neutralized with a concentrated aqueous solution of hydrochloric acid, and the deposited crystals were collected by filtration. The collected crystals were washed with water, dried, and recrystallized from dimethylformamide/water to give 1.55 g (yield 30%) of Compound 114 as pale yellow needles.

Melting Point: 241.6°–242.6° C.; Elemental Analysis: $C_{17}H_{17}ClN_4O_4$, Calcd. (%): C, 54.18; H, 4.54; N, 14.86; Found (%): C, 54.31; H, 4.54; N, 14.43; IR (KBr) $v_{max}$ (cm$^{-1}$): 1704, 1653, 1496, 1300; NMR (270 MHz; DMSO-d$_6$)δ(ppm): 7.88(1H, d, J=16.2 Hz), 7.62 (1H, d, J=8.9 Hz), 7.13 (1H, d, J=8.9 Hz), 6.97 (1H, d, J=16.2Hz), 3.88 (3H, S), 3.77 (3H, s), 3.47 (3H, s), 3.25 (3H, s).

REFERENCE EXAMPLE 58

(E)-8-(2-Chloro-3,4-dimethoxystyryl)caffeine (Compound 115)

Substantially the same procedure as in Example 8 was repeated using 1.0 g (2.66 mmol) of Compound 114 obtained in Reference Example 57 in place of Compound 64. Then, the resultant crude crystals were recrystallized from toluene to give 840 mg (yield 81%) of Compound 115 as a yellow powder.

Melting Point: 284.6°–288.0° C.; Elemental Analysis: $C_{18}H_{19}ClN_4O_4$, Calcd. (%): C, 55.31; H, 4.59; N, 14.33; Found (%): C, 55.40; H, 4.83; N, 14.09; IR (KBr) $v_{max}$ (cm$^{-1}$): 1688, 1650, 1493, 1290; NMR (270 MHz; CDCl$_3$)δ(ppm): 8.10(1H, d, J=15.8 Hz), 7.43(1H, d, J=8.8 Hz), 6.88(1H, d, J=8.8 Hz), 6.83 (1H, d, J=15.8 Hz), 4.06(3H, s), 3.93(3H, s), 3.90 (3H, s), 3.64 (3H, s), 3.42 (3H, s).

REFERENCE EXAMPLE 59

(E)-8-(3,4-Difluorostyryl)-1,3-diethylxanthine (Compound 116)

Substantially the same procedure as in Example 7 was repeated using 2.50 g (12.6 mmol) of 5,6-diamino-1,3-diethyluracil and 2.79 g (15.2 mmol) of 3,4-difluorocinnamic acid. Then, the resultant crude crystals were recrystallized from dioxane/water to give 2.12 g (yield 49%) of Compound 116 as gray plates.

Melting Point: >300° C.; Elemental Analysis: $C_{17}H_{16}F_2N_4O_2$, Calcd. (%): C, 58.95; H, 4.65; N, 16.17; Found (%): C, 59.25; H, 4.59; N, 16.42; IR (KBr) $v_{max}$ (cm$^{-1}$): 1688, 1640, 1519; NMR (270 MHz; DMSO-d$_6$)δ(ppm): 7.78(1H, dd, J=11.4, 7.1 Hz), 7.60 (1H, d, J=16.3 Hz), 7.50–7.45 (2H, m), 7.07(1H, d, J=16.3 Hz), 4.06(2H, q, J=7.0 Hz), 3.94 (2H, q, J=7.1 Hz), 1.26(3H, t, J=7.0 Hz), 1.14 (3H, t, J=7.1 Hz).

REFERENCE EXAMPLE 60

(E)-8-(3,4-Difluorostyryl)-1,3-diethyl-7-methylxanthine (Compound 117)

Substantially the same procedure as in Example 8 was repeated using 1.70 g (4.91 mmol) of Compound 116 obtained in Reference Example 59 in place of Compound 64. Then, the resultant crude crystals were recrystallized from toluene/cyclohexane to give 1.29 g (yield 73%) of Compound as yellow needles.

Melting Point: 208.5°–210.8° C.; Elemental Analysis: $C_{18}H_{18}F_2N_4O_2$, Calcd. (%): C, 59.99; H, 5.03; N, 15.54; Found (%): C, 60.09; H, 5.04; N, 15.19; IR (KBr) $v_{max}$ (cm$^{-1}$): 1688, 1652, 1545, 1520, 1441; NMR (270 MHz; DMSO-d$_6$)δ(ppm): 8.02(1H, ddd, J=12.4, 7.7, 2.0 Hz), 7.65–7.60(1H, m), 7.61(1H, d, J=15.8 Hz), 7.54–7.43(1H, m), 7.40(1H, d, J=15.8Hz), 4.08–4.04 (2H, m), 4.04 (3H, s), 3.92 (2H, q, J=6.9 Hz), 1.26(3H, t, J=6.9 Hz), 1.13(3H, t, J=6.9 Hz).

REFERENCE EXAMPLE 61

(E)-8-(3-Bromo-4-methoxystyryl)-1,3-diethylxanthine (Compound 118)

Substantially the same procedure as in Example 7 was repeated using 2.00 g (10.1 mmol) of 5,6-diamino-1,3-diethyluracil and 2.72 g (10.6 mmol) of 3-bromo-4methoxycinnamic acid. Then, the resultant crude crystals were recrystallized from dioxane to give 726 mg (yield 17%) of Compound 118 as pale brown needles.

Melting Point: >280° C.; Elemental Analysis: $C_{18}H_{19}BrN_4O_3$, Calcd. (%): C, 51.57; H, 4.57; N, 13.36; Found (%): C, 51.33; H, 4.56; N, 13.17; IR (KBr) $v_{max}$ (cm$^{-1}$): 1694, 1648, 1506, 1281, 1260; NMR (270 MHz; DMSO-d$_6$)δ(ppm): 13.52(1H, brs), 7.87 (1H, d, J=2.0 Hz), 7.63(1H, dd, J=8.4, 2.0 Hz), 7.56 (1H, d, J=16.3 Hz), 7.16(1H, d, J=8.4 Hz), 6.95(1H, d, J=16.3 Hz), 4.06(2H, q, J=6.9 Hz), 3.93(2H, q, J=6.9 Hz), 3.89(3H, s), 1.26(3H, t, J=6.9 Hz), 1.14 (3H, t, J=6.9 Hz).

REFERENCE EXAMPLE 62

(E)-8-(3-Bromo-4-methoxystyryl)-1,3-diethyl-7-methylxanthine (Compound 119)

Substantially the same procedure as in Example-8 was repeated using 400 mg (0.95 mmol) of Compound 118 obtained in Reference Example 61 in place of Compound 64. Then, the resultant crude crystals were recrystallized from dioxane/water to give 332 mg (yield 80%) of Compound 119 as pale yellow needles.

Melting Point: 219.1°–223.7° C.; Elemental Analysis: $C_{19}H_{21}BrN_4O_3$, Calcd. (%): C, 52.67; H, 4.88; N, 12.93; Found (%): C, 52.79; H, 4.97; N, 12.70; IR (KBr)$v_{max}$ (cm$^{-1}$): 1686, 1651, 1541, 1501, 1435; NMR (270 MHz; CDCl$_3$)δ(ppm): 7.83(1H, d, J=2.0 Hz), 7.69(1H, d, J=15.8 Hz), 7.48(1H, dd, J=8.4, 2.0 Hz), 6.92(1H, d, J=8.4 Hz), 6.78(1H, d, J=15.8 Hz), 4.21 (2H, q, J=6.9 Hz), 4.09(2H, q, J=6.9 Hz), 4.06(3H, s), 3.95(3H, s), 1.38(3H, t, J=6.9 Hz), 1.26(3H, t, J=6.9 Hz).

REFERENCE EXAMPLE 63

(E)-8-(3-Bromo-4-methoxystyryl)theophylline (Compound 120)

Substantially the same procedure as in Example 7 was repeated using 2.00 g (11.8 mmol) of 5,6-diamino-1,3-dimethyluracil and 3.32 g (12.9 retool) of 3-bromo-4-methoxycinnamic acid. Then, the resultant crude crystals were recrystallized from dimethylformamide to give 2.00 g (yield 43%) of Compound 120 as a pale yellow powder.

Melting Point: >280° C.; Elemental Analysis: $C_{16}H_{15}BrN_4O_3$, Calcd. (%): C, 49.12; H, 3.86; N, 14.32; Found (%): C, 49.16; H, 3.80; N, 14.06; IR (KBr) $v_{max}$ (cm$^{-1}$): 1691, 1644, 1598, 1499, 1257; NMR (270 MHz; DMSO-d$_6$)δ(ppm): 13.41(1H, brs), 7.84 (1H, d, J=2.0 Hz), 7.61(1H, dd, J=8.4, 2.0 Hz), 7.56 (1H, d, J=16.3 Hz), 7.15(1H, d, J=8.4 Hz), 6.92(1H, d, J=16.3 Hz), 3.89(3H, s), 3.47(3H, s), 3.26(3H, s).

REFERENCE EXAMPLE 64

(E)-8-(3-Bromo-4-methoxystyryl)caffeine (Compound 121)

Substantially the same procedure as in Example 8 was repeated using 1.00 g (2.56 mmol) of Compound 120 obtained in Reference Example 63 in place of Compound 64. Then, the resultant crude crystals were recrystallized from dioxane to give 877 mg (yield 85%) of Compound 121 as a yellow powder.

Melting Point: 283.3°–283.4° C.; Elemental Analysis: $C_{17}H_{17}BrN_4O_3$, Calcd. (%): C, 50.39; H, 4.23; N, 13.83; Found (%): C, 50.04; H, 4.00; N, 13.49; IR (KBr) $v_{max}$ (cm$^{-1}$): 1693, 1654, 1500; NMR (270 MHz; CDCl$_3$)δ(ppm): 7.82(1H, d, J=2.0 Hz), 7.70(1H, d, J=15.8 Hz), 7.47(1H, dd, J=8.4, 2.0 Hz), 6.92 (1H, d, J=8.4 Hz), 6.78 (1H, d, J=15.8 Hz), 4.07 (3H, s), 3.95(3H, s), 3.62(3H, s), 3.42(3H, s).

REFERENCE EXAMPLE 65

(E)-8-(2-Bromo-4,5-dimethoxystyryl)-1,3-diethylxanthine (Compound 122)

Substantially the same procedure as in Example 7 was repeated using 3.00 g (15.1 mmol) of 5,6-diamino-1,3-diethyluracil and 4.78 g (17.2 mmol) of 2-bromo-4,5-dimethoxycinnamic acid. Then, the resultant crude crystals were recrystallized from dioxane to give 3.34 g (yield 49%) of Compound 122 as pale yellow needles.

Melting Point: >285° C.; Elemental Analysis: $C_{19}H_{21}BrN_4O_4$, Calcd. (%): C, 50.79; H, 4.71; N, 12.47; Found (%): C, 50.49; H, 4.64; N, 12.36; IR (KBr) $v_{max}$ (cm$^{-1}$): 1693, 1621, 1509, 1260; NMR (270 MHz; DMSO-d$_6$)δ(ppm): 13.65 (1H, brs), 7.81 (1H, d, J=16.3 Hz), 7.37(1H, s), 7.20(1H, s), 7.06 (1H, d, J=16.3 Hz), 4.07(2H, q, J=6.9 Hz), 3.95(2H, q, J=6.9 Hz), 3.86(3H, s), 3.82(3H, s), 1.27(3H, t, J=6.9 Hz), 1.15 (3H, t, J=6.9 Hz).

REFERENCE EXAMPLE 66

(E)-8-(2-Bromo-4,5-dimethoxystyryl)-1,3-diethyl-7-methylxanthine (Compound 123)

Substantially the same procedure as in Example 8 was repeated using 1.50 g (3.34 mmol) of Compound 122 obtained in Reference Example 65 in place of Compound 64. Then, the resultant crude crystals were recrystallized from hexane/ethyl acetate to give 1.43 g (yield 92%) of Compound as yellow needles.

Melting Point: 234.2°–234.9° C.; Elemental Analysis: $C_{20}H_{23}BrN_4O_4$, Calcd. (%): C, 51.85; H, 5.00; N, 12.09; Found (%): C, 51.96; H, 4.95; N, 11.90; IR (KBr) $v_{max}$ (cm$^{-1}$): 1688, 1648, 1504, 1307, 1261; NMR (270 MHz; CDCl$_3$)δ(ppm): 8.01(1H, d, J=15.8 Hz), 7.11 (1H, s), 7.09(1H, s), 6.76(1H, d, J=15.8 Hz), 4.22(2H, q, J=6.9 Hz), 4.09(2H, q, J=6.9 Hz), 4.08 (3H, s), 3.95 (3H, s), 3.92 (3H, s), 1.39 (3H, t, J=6.9 Hz), 1.27 (3H, t, J=6.9 Hz).

REFERENCE EXAMPLE 67

(E)-8-(4,5-Dimethoxy-2-nitrostyryl)-1,3-diethylxanthine (Compound 124)

Substantially the same procedure as in Example 7 was repeated using 1.50 g (7.57 mmol) of 5,6-diamino-1,3-diethyluracil and 2.11 g (8.33 mmol) of 4,5-dimethoxy-2-nitrocinnamic acid. Then, the resultant crude crystals were recrystallized from dioxane to give 1.22 g (yield 39%) of Compound 124 as orange needles.

Melting Point: 283.6°–284.2° C.; Elemental Analysis: $C_{19}H_{21}N_5O_6$, Calcd. (%): C, 54.94; H, 5.09; N, 16.86; Found (%): C, 54.90; H, 5.07; N, 16.88; IR (KBr) $v_{max}$ (cm$^{-1}$): 1692, 1641, 1520; NMR (270 MHz; DMSO-d$_6$)δ(ppm): 7.99 (1H, d, J=16.3 Hz), 7.61(1H, s), 7.38(1H, s), 7.15(1H, d, J=16.3 Hz), 4.06 (2H, q, J=6.9 Hz), 3.98 (3H, s), 3.95 (2H, q, J=6.9 Hz), 3.89(3H, s), 1.26(3H, t, J=6.9 Hz), 1.15 (3H, t, J=6.9 Hz).

REFERENCE EXAMPLE 68

(E)-8-(4,5-Dimethoxy-2-nitrostyryl)-1,3-diethyl-7-methylxanthine (Compound 125)

Substantially the same procedure as in Example 8 was repeated using 822 mg (1.98 mmol) of Compound 124 obtained in Reference Example 67 in place of Compound 64 Then, the resultant crude crystals were recrystallized from ethyl acetate to give 762 mg (yield 90%) of Compound as orange needles.

Melting Point: 246.3°–246.8° C.; Elemental Analysis: $C_{20}H_{23}N_5O_6$, Calcd. (%): C, 55.94; H, 5.40; N, 16.31; Found (%): C, 55.98; H, 5.42; N, 16.43; IR (KBr) $v_{max}$ (cm$^{-1}$): 1692, 1657, 1519, 1273; NMR (270 MHz; CDCl$_3$)δ(ppm): 8.27 (1H, d, J=15.8 Hz), 7.66(1H, s), 7.03(1H, s), 6.77 (1H, d, J=15.8 Hz), 4.21 (2H, q, J=6.9 Hz), 4.10 (3H, s), 4.09 (2H, q, J=6.9 Hz), 4.05 (3H, s), 4.00(3H, s), 1.37(3H, t, J=6.9 Hz), 1.27 (3H, t, J=6.9 Hz).

REFERENCE EXAMPLE 69

(E)-1,3-Diethyl-8-(3-methoxy-2-nitrostyryl)xanthine (Compound 126)

Substantially the same procedure as in Example 7 was repeated using 2.50 g (12.6 mmol) of 5,6-diamino-1,3-diethyluracil and 3.10 g (13.9 mmol) of 3-methoxy-2-nitrocinnamic acid. Then, the resultant crude crystals were recrystallized from dioxane/water to give 2.28 g (yield 47%) of Compound 126 as orange needles.

Melting Point: >285° C.; Elemental Analysis: $C_{18}H_{19}N_5O_5$, Calcd. (%): C, 56.10; H, 4.97; N, 18.17; Found (%): C, 56.37; H, 4.88; N, 17.85; IR (KBr) $v_{max}$ (cm$^{-1}$): 1695, 1640, 1533; NMR (270 MHz; DMSO-d$_6$)δ(ppm): 13.88 (1H, brs), 7.60– 7.56(2H, m), 7.39(1H, d, J=16.3 Hz), 7.32(1H, dd, J=6.9, 3.0 Hz), 7.21 (1H, d, J=16.3 Hz), 4.05 (2H, q, J=6.9 Hz), 3.94 (2H, q, J=6.9 Hz), 3.91 (3H, s), 1.25 (3H, t, J=6.9 Hz), 1.14(3H, t, J=6.9 Hz).

REFERENCE EXAMPLE 70

(E)-1,3-Diethyl-8-(3-methoxy-2-nitrostyryl)-7-methylxanthine (Compound 127)

Substantially the same procedure as in Example 8 was repeated using 688 mg (1.79 mmol) of Compound 126 obtained in Reference Example 69 in place of Compound 64. Then, the resultant crude crystals were recrystallized from ethyl acetate to give 623 mg (yield 87%) of Compound 127 as yellow needles.

Melting Point: 258.4°–259.9° C.; Elemental Analysis: $C_{19}H_{21}N_5O_5$, Calcd. (%): C, 57.14; H, 5.30; N, 17.53; Found (%): C, 57.26; H, 5.34; N, 17.26; IR (KBr) $v_{max}$ (cm$^{-1}$): 1697, 1546, 1530; NMR (270 MHz; CDCl$_3$)δ(ppm): 7.62 (1H, d, J=15.3 Hz), 7.46 (1H, dd, J=8.4, 7.9 Hz), 7.30 (1H, d, J=7.9 Hz), 7.05 (1H, d, J=8.4 Hz), 6.95 (1H, d, J=15.3 Hz), 4.19 (2H, q, J=6.9 Hz), 4.08 (2H, q, J=6.9 Hz), 4.05 (3H, s), 3.94(3H, s), 1.36(3H, t, J=6.9 Hz), 1.26(3H, t, J=6.9 Hz).

REFERENCE EXAMPLE 71

(E)-1,3-Diethyl-8-(3-fluorostyryl)xanthine (Compound 128)

Substantially the same procedure as in Example 7 was repeated using 3.00 g (15.1 mmol) of 5,6-diamino-1,3-diethyluracil and 2.77 g (16.7 mmol) of 3-fluorocinnamic acid. Then, the resultant crude crystals were recrystallized from dioxane/water to give 1.96 g (yield 40%) of Compound 128 as a pale yellow powder.

Melting Point: >270° C.; Elemental Analysis: $C_{17}H_{17}FN_4O_2$, Calcd. (%): C, 62.19; H, 5.22; N, 17.06; Found (%): C, 61.90; H, 5.21; N, 17.15; IR (KBr) $v_{max}$ (cm$^{-1}$): 1692, 1622, 1501; NMR (270 MHz; $CF_3COOD$)δ(ppm): 11.6(1H, brs), 8.05(1H, d, J=16.5 Hz), 7.56–7.46(2H, m), 7.38(1H, d, J=9.2 Hz), 7.29–7.22(1H, m), 7.19(1H, d, J=16.5 Hz), 4.43–4.03 (4H, m), 1.52 (3H, t, J=7.3Hz), 1.41 (3H, t, J=6.9 Hz).

REFERENCE EXAMPLE 72

(E)-1,3-Diethyl-8-(3-fluorostyryl)-7-methylxanthine (Compound 129)

Substantially the same procedure as in Example 8 was repeated using 1.80 g (5.49 mmol) of Compound 128 obtained in Reference Example 71 in place of Compound 64. Then, the resultant crude crystals were recrystallized from toluene/cyclohexane to give 1.04 g (yield 55%) of Compound as white needles.

Melting Point: 178.2°–179.4° C.; Elemental Analysis: $C_{18}H_{19}FN_4O_2 \cdot 0.25H_2O$, Calcd. (%): C, 62.33; H, 5.67; N, 16.15; Found (%): C, 62.19; H, 5.63; N, 16.26; IR (KBr) $v_{max}$ (cm$^{-1}$): 1694, 1650; NMR (270 MHz; DMSO-$d_6$)δ(ppm): 7.75(1H, dd, J=10.1, 2.0 Hz), 7.66 (1H, d, J=15.8 Hz), 7.63–7.60 (1H, m), 7.50–7.42 (1H, m), 7.44 (1H, d, J=15.8 Hz), 7.19 (1H, dt, J=2.0, 8.3 Hz), 4.10–4.05(2H, m), 4.05 (3H, s), 3.92(2H, q, J=7.0 Hz), 1.26(3H, t, J=7.1 Hz), 1.13 (3H, t, J=7.0 Hz).

REFERENCE EXAMPLE 73

(E)-8-(3,5-Dimethoxystyryl)-1,3-diethylxanthine (Compound 130)

Substantially the same procedure as in Example 7 was repeated using 3.00 g (15.1 mmol) of 5,6-diamino-1,3-diethyluracil and 3.48 g (16.7 mmol) of 3,5-dimethoxycinnamic acid. Then, the resultant crude crystals were recrystallized from ethanol/water to give 2.74 g (yield 49%) of Compound 130 as a white powder.

Melting Point: >270° C.; Elemental Analysis: $C_{19}H_{22}N_4O_4 \cdot 0.5H_2O$, Calcd. (%): C, 60.15; H, 6.11; N, 14.77; Found (%): C, 60.41; H, 6.15; N, 15.02; IR (KBr) $v_{max}$ (cm$^{-1}$): 1686, 1638, 1587; NMR (270 MHz; DMSO-$d_6$)δ(ppm): 7.57(1H, d, J=16.5 Hz), 7.07(1H, d, J=16.5 Hz), 6.79(2H, d, J=2.0 Hz), 6.50 (1H, t, J=2.0 Hz), 4.06(2H, q, J=7.0 Hz), 3.94(2H, q, J=6.9 Hz), 3.79(6H, s), 1.26(3H, t, J=7.0 Hz), 1.14 (3H, t, J=6.9 Hz).

REFERENCE EXAMPLE 74

(E)-8-(3,5-Dimethoxystyryl)-1,3-diethyl-7-methylxanthine (Compound 31)

Substantially the same procedure as in Example 8 was repeated using 3.00 g (8.11 mmol) of Compound 130 obtained in Reference Example 73 in place of Compound 64. Then, the resultant crude crystals were recrystallized from toluene/cyclohexane to give 2.28 g (yield 73%) of Compound 131 as yellow needles.

Melting Point: 184.2°–185.3° C.; Elemental Analysis: $C_{20}H_{24}N_4O_4$, Calcd. (%): C, 62.49; H, 6.29; N, 14.57; Found (%): C, 62.66; H, 6.48; N, 14.65; IR (KBr) $v_{max}$ (cm$^{-1}$): 1690, 1659, 1595; NMR (270 MHz; DMSO-$d_6$)δ(ppm): 7.60(1H, d, J=15.7 Hz), 7.35(1H, d, J=15.7 Hz), 6.98(2H, d, J=2.2 Hz), 6.51 (1H, t, J=2.2 Hz), 4.11–4.01(2H, m), 4.05(3H, s), 3.92(2H, q, J=7.0 Hz), 3.80(6H, s), 1.26(3H, t, J=7.1 Hz), 1.13 (3H, t, J=7.0 Hz).

REFERENCE EXAMPLE 75

(E)-8-(3-Chlorostyryl)-1,3-diethylxanthine (Compound 132)

Substantially the same procedure as in Example 7 was repeated using 3.50 g (17.7 mmol) of 5,6-diamino-1,3-diethyluracil and 3.55 g (19.4 mmol) of 3-chlorocinnamic acid. Then, the resultant crude crystals were recrystallized from dioxane/water to give 2.57 g (yield 42%) of Compound 132 as white plates.

Melting Point: >280° C.; Elemental Analysis: $C_{17}H_{17}ClN_4O_2$, Calcd. (%): C, 59.22; H, 4.97; N, 16.25; Found (%): C, 59.12; H, 5.01; N, 16.30; IR (KBr) $v_{max}$ (cm$^{-1}$): 1689, 1640, 1490; NMR (270 MHz; $CF_3COOD$)δ(ppm): 8.35(1H, d, J=16.4 Hz), 8.01(1H, s), 7.52–7.36(3H, m), 7.14(1H, d, J=16.4 Hz), 4.37–4.23 (4H, m), 1.45 (3H, t, J=6.8 Hz), 1.34(3H, t, J=6.9 Hz).

REFERENCE EXAMPLE 76

(E)-8-(3-Chlorostyryl)-1,3-diethyl-7-methylxanthine (Compound 133)

Substantially the same procedure as in Example 8 was repeated using 3.00 g (8.72 mmol) of Compound 132 obtained in Reference Example 75 in place of Compound 64. Then, the resultant crude crystals were recrystallized from ethanol/water to give 1.41 g (yield 45%) of Compound 133 as a pale yellow powder.

Melting Point: 134.0°–134.4° C.; Elemental Analysis: $C_{18}H_{19}ClN_4O_2 \cdot H_2O$, Calcd. (%): C, 57.37; H, 5.62; N, 14.87; Found (%): C, 57.67; H, 5.51; N, 14.92; IR (KBr) $v_{max}$ (cm$^{-1}$): 1688, 1656, 1545; NMR (270 MHz; DMSO-$d_6$)δ(ppm): 7.98(1H, s), 7.72(1H, t, J=2.0 Hz), 7.63 (1H, d, J=15.8 Hz), 7.49–7.39(3H, m), 4.11–4.03 (2H, m), 4.05(3H, s), 3.92(2H, q, J=6.9 Hz), 1.26 (3H, t, J=6.9 Hz), 1.13 (3H, t, J=6.9 Hz).

REFERENCE EXAMPLE 77

(E)-1,3-Diethyl-8-(α-methylstyryl)xanthine (Compound 134)

Substantially the same procedure as in Example 7 was repeated using 2.00 g (10.1 mmol) of 5,6-diamino-1,3-diethyluracil and 1.80 g (11.1 mmol) of α-methylcinnamic acid. Then, the resultant crude crystals were recrystallized from ethanol/water to give 1.63 g (yield 50%) of Compound 134 as white needles.

Melting Point: 250.8°–252.0° C.; Elemental Analysis: $C_{18}H_{20}N_4O_2$, Calcd. (%): C, 66.65; H, 6.21; N, 17.27; Found (%): C, 66.62; H, 6.30; N, 17.31; IR (KBr) $v_{max}$ (cm$^{-1}$): 1696, 1657, 1493; NMR (270 MHz; DMSO-$d_6$)δ(ppm): 13.44(1H, brs), 7.61 (1H, d, J=1.3 Hz), 7.49–7.30(6H, m), 4.07(2H, q, J=7.0 Hz), 3.95 (2H, q, J=6.9

Hz), 2.31 (3H, d, J=1.3 Hz), 1.26(3H, t, J=7.0 Hz), 1.14(3H, t, J= 6.9 Hz).

REFERENCE EXAMPLE 78

(E)-1,3-Diethyl-7-methyl-8-(α-methylstyryl)xanthine
(Compound 135)

Substantially the same procedure as in Example 8 was repeated using 1.00 g (3.09 mmol) of Compound 134 obtained in Reference Example 77 in place of Compound 64. Then, the resultant crude crystals were recrystallized from ethanol/2-propanol to give 800 mg (yield 77%) of Compound 135 as white needles.

Melting Point: 137.2°–139.3° C.; Elemental Analysis: $C_{19}H_{22}N_4O_2$, Calcd. (%): C, 67.44; H, 6.55; N, 16.56; Found (%): C, 67.01; H, 6.73; N, 16.62; IR (KBr) $v_{max}$ (cm$^{-1}$): 1699, 1654, 1537; NMR (270 MHz; DMSO-$d_6$)δ(ppm): 7.52–7.32(5H, m), 7.00 (1H, d, J=1.3 Hz), 4.04(2H, q, J=7.2 Hz), 4.00(3H, s), 3.94(2H, q, J=6.9 Hz), 2.29(3H, d, J=1.3 Hz), 1.24(3H, t, J=7.2 Hz), 1.13(3H, t, J=6.9 Hz).

REFERENCE EXAMPLE 79

(E)-1,3-Diethyl-8-(4-trifluoromethylstyryl)xanthine
(Compound 136)

Substantially the same procedure as in Example 7 was repeated using 2.20 g (11.2 mmol) of 5,6-diamino-1,3-diethyluracil and 2.66 g (12.3 mmol) of 4-trifluoromethylcinnamic acid. Then, the resultant crude crystals were recrystallized from dioxane/water to give 2.09 g (yield 49%) of Compound 136 as a white powder.

Melting Point: >280° C.; Elemental Analysis: $C_{18}H_{17}F_3N_4O_2$, Calcd. (%): C, 57.14; H, 4.53; N, 14.81; Found (%): C, 57.25; H, 4.51; N, 14.82; IR (KBr) $v_{max}$ (cm$^{-1}$): 1696, 1654, 1637, 1324; NMR (270 MHz; DMSO-$d_6$)δ(ppm): 7.86(2H, d, J=8.1 Hz), 7.76(2H, d, J=8.1 Hz), 7.70(1H, d, J=16.5 Hz), 7.20 (1H, d, J=16.5 Hz), 4.07(2H, q, J=7.1 Hz), 3.94(2H, q, J=7.0 Hz), 1.26(3H, t, J=7.1 Hz), 1.14(3H, t, J=7.0 Hz).

REFERENCE EXAMPLE 80

(E)-1,3-Diethyl-7-methyl-8-(4-trifluoromethylstyryl)xanthine (Compound 137)

Substantially the same procedure as in Example 8 was repeated using 1.30 g (3.44 mmol) of Compound 136 obtained in Reference Example 79 in place of Compound 64. Then, the resultant crude crystals were recrystallized from toluene/cyclohexane to give 990 mg (yield 73%) of Compound 137 as yellow needles.

Melting Point: 207.8°–209.0° C.; Elemental Analysis: $C_{19}H_{19}F_3N_4O_2$, Calcd. (%): C, 58.16; H, 4.88; N, 14.28; Found (%): C, 58.22; H, 4.84; N, 14.32; IR (KBr) $v_{max}$ (cm$^{-1}$): 1700, 1667, 1325; NMR (270 MHz; DMSO-$d_6$)δ(ppm): 8.03(2H, d, J=8.3 Hz), 7.76(2H, d, J=8.3 Hz), 7.73(1H, d, J=15.8 Hz), 7.53 (1H, d, J=15.8 Hz), 4.11–4.03(2H, m), 4.09(3H, s), 3.92 (2H, q, J=7.0 Hz), 1.27 (3H, t, J=6.9 Hz), 1.13 (3H, t, J=7.0 Hz).

REFERENCE EXAMPLE 81

(E)-1,3-Diethyl-8-(α-fluorostyryl)xanthine
(Compound 138)

Substantially the same procedure as in Example 7 was repeated using 1.08 g (5.47 mmol) of 5,6-diamino-1,3-diethyluracil and 1.00 g (6.02 mmol) of α-fluorocinnamic acid. Then, the resultant crude crystals were recrystallized from dioxane/water to give 1.04 g (yield 58%) of Compound 138 as white plates.

Melting Point: >280° C.; Elemental Analysis: $C_{17}H_{17}FN_4O_2$, Calcd. (%): C, 62.19; H, 5.22; N, 17.06; Found (%): C, 62.28; H, 5.22; N, 17.07; IR (KBr) $v_{max}$ (cm$^{-1}$): 1695, 1644, 1506; NMR (270 MHz; DMSO-$d_6$)δ(ppm): 7.68(2H, d, J=6.9 Hz), 7.47–7.35 (3H, m), 6.93(1H, d, J=36.3 Hz), 4.06(2H, q, J=6.9 Hz), 3.94 (2H, q, J=7.0 Hz), 1.26 (3H, t, J=6.9 Hz), 1.14 (3H, t, J=7.0 Hz).

REFERENCE EXAMPLE 82

(E)-1,3-Diethyl-8-(α-fluorostyryl)-7-methylxanthine
(Compound 139)

Substantially the same procedure as in Example 8 was repeated using 800 mg (2.44 mmol) of Compound 138 obtained in Reference Example 81 in place of Compound 64. Then, the resultant crude crystals were recrystallized from toluene/cyclohexane to give 550 mg (yield 66%) of Compound 139 as a white powder.

Melting Point: 153.5°–155.5° C.; Elemental Analysis: $C_{18}H_{19}FN_4O_2$, Calcd. (%): C, 63.15; H, 5.59; N, 16.36; Found (%): C, 63.25; H, 5.66; N, 16.44; IR (KBr) $v_{max}$ (cm$^{-1}$): 1696, 1662, 1539; NMR (270 MHz; CDCl$_3$)δ(ppm): 7.68–7.65(2H, m), 7.47–7.31(3H, m), 6.89(1H, d, J=39.3 Hz), 4.13–4.05(2H, m), 4.21(3H, s), 4.09(2H, q, J=7.1 Hz), 1.37(3H, t, J=7.1 Hz), 1.27 (3H, t, J=7.1 Hz).

REFERENCE EXAMPLE 83

(E)-8-(4-Bromostyryl)-1,3-diethylxanthine
(Compound 140)

Substantially the same procedure as in Example 7 was repeated using 2.20 g (11.1 mmol) of 5,6-diamino-1,3-diethyluracil and 2.78 g (12.2 mmol) of 4-bromocinnamic acid. Then, the resultant crude crystals were recrystallized from tetrahydrofuran/water to give 930 mg (yield 22%) of Compound 140 as yellow columns.

Melting Point: >270° C.; Elemental Analysis: $C_{17}H_{17}BrN_4O_2$, Calcd. (%): C, 52.46; H, 4.40; N, 14.39; Found (%): C, 52.41; H, 4.28; N, 14.43; IR (KBr) $v_{max}$ (cm$^{-1}$): 1686, 1619, 1496; NMR (270 MHz; DMSO-$d_6$)δ(ppm): 7.63–7.18(4H, m), 7.60 (1H, d, J=16.2 Hz), 7.07(1H, d, J=16.2 Hz), 4.06(2H, q, J=6.9 Hz), 3.94(2H, q, J=6.8 Hz), 1.26(3H, t, J=6.9 Hz), 1.14 (3H, t, J=6.8 Hz).

REFERENCE EXAMPLE 84

(E)-8-(4-Bromostyryl)-1,3-diethyl-7
-methylxanthine (Compound 141)

Substantially the same procedure as in Example 8 was repeated using 1.80 g (4.63 mmol) of Compound 143 obtained in Reference Example 83 in place of Compound 64. Then, the resultant crude crystals were recrystallized from toluene/ethanol to give 660 mg (yield 35%) of Compound 141 as pale yellow needles.

Melting Point: 198.5°–198.9° C.; Elemental Analysis: $C_{18}H_{19}BrN_4O_2 \cdot 0.25H_2O$, Calcd. (%): C, 53.02; H, 4.82; N, 13.74; Found (%): C, 53.09; H, 4.62; N, 13.79; IR (KBr) $v_{max}$ (cm$^{-1}$): 1691, 1662, 1543; NMR (270 MHz; DMSO-$d_6$)δ(ppm): 7.78(2H, d, J=7.6 Hz), 7.67–7.61(3H, m), 7.41(1H, d, J=16.2 Hz), 4.11–4.04 (2H, m), 4.04(3H, s), 3.92(2H, q, J=6.7 Hz), 1.26 (3H, t, J=6.8 Hz), 1.13(3H, t, J=6.7 Hz).

REFERENCE EXAMPLE 85

(E)-1,3-Diethyl-8-(3-trifluoromethoxystyryl)xanthine (Compound 142)

Substantially the same procedure as in Example 7 was repeated using 1.00 g (5.05 mmol) of 5,6-diamino-1,3-diethyluracil and 1.29 g (5.56 mmol) of 3-trifluoromethoxycinnamic acid. Then, the resultant crude crystals were recrystallized from dioxane/water to give 1.19 g (yield 60%) of Compound 142 as white needles.

Melting Point: 266.4°–267.3° C.; Elemental Analysis: $C_{18}H_{17}F_3N_4O_3$, Calcd. (%): C, 54.83; H, 4.34; N, 14.21; Found (%): C, 54.79; H, 4.22; N, 14.20; IR (KBr) $v_{max}$ (cm$^{-1}$): 1697, 1658, 1500, 1262; NMR (270 MHz; DMSO-$d_6$)δ(ppm): 13.57 (1H, brs), 7.67 (1H, d, J=16.5 Hz), 7.66(1H, d, J=7.9 Hz), 7.63(1H, s), 7.55 (1H, t, J=7.9 Hz), 7.34 (1H, d, J=7.9 Hz), 7.14 (1H, d, J=16.5 Hz), 4.07 (2H, q, J=6.9 Hz), 3.94 (2H, q, J=6.9 Hz), 1.27 (3H, t, J=6.9 Hz), 1.14 (3H, t, J=6.9 Hz).

REFERENCE EXAMPLE 86

(E)-1,3-Diethyl-7-methyl-8-(3-trifluoromethoxystyryl)xanthine (Compound 143)

Substantially the same procedure as in Example 8 was repeated using 700 mg (1.78 mmol) of Compound 142 obtained in Reference Example 85 in place of Compound 64. Then, the resultant crude crystals were recrystallized from ethyl acetate to give 329 mg (yield 45%) of Compound 143 as white needles.

Melting Point: 178.7°–179.3° C.; Elemental Analysis: $C_{19}H_{19}F_3N_4O_3$, Calcd. (%): C, 55.88; H, 4.69; N, 13.72; Found (%): C, 56.27; H, 4.68; N, 13.67; IR (KBr) $v_{max}$ (cm$^{-1}$): 1694, 1660, 1265, 1213; NMR (270 MHz; CDCl$_3$)δ(ppm): 7.77(1H, d, J=15.8 Hz), 7.53–7.20(4H, m), 6.93(1H, d, J=15.8 Hz), 4.21(2H, q, J=6.9 Hz), 4.09(2H, q, J=6.9 Hz), 4.08(3H, s), 1.38(3H, t, J=6.9 Hz), 1.27(3H, t, J=6.9 Hz).

REFERENCE EXAMPLE 87

(E)-1,3-Diethyl-8-(4-methoxymethoxystyryl)xanthine (Compound 144)

Substantially the same procedure as in Example 7 was repeated using 4.00 g (20.2 mmol) of 5,6-diamino-1,3-diethyluracil and 4.62 g (22.2 mmol) of 4-methoxymethoxycinnamic acid. Then, the resultant crude crystals were recrystallized from dioxane/water to give 4.80 g (yield 64%) of Compound 144 as pale yellow needles.

Melting Point: 270.2°–271.4° C.; Elemental Analysis: $C_{19}H_{22}N_4O_4$, Calcd. (%): C, 61.61; H, 5.98; N, 15.13; Found (%): C, 61.97; H, 5.98; N, 15.05; IR (KBr) $v_{max}$ (cm$^{-1}$): 1695, 1641, 1510, 1238; NMR (270 MHz; DMSO-$d_6$)δ(ppm): 13.40 (1H, brs), 7.60 (1H, d, J=16.5 Hz), 7.57 (2H, d, J=8.6 Hz), 7.06 (2H, d, J=8.6 Hz), 6.90 (1H, d, J=16.5 Hz), 5.23 (2H, s), 4.07 (2H, q, J=6.9 Hz), 3.94 (2H, q, J=6.9 Hz), 3.39 (3H, s), 1.26(3H, t, J=6.9 Hz), 1.14 (3H, t, J=6.9 Hz).

REFERENCE EXAMPLE 88

(E)-1,3-Diethyl-8-(4-methoxymethoxystyryl)-7-methylxanthine (Compound 145)

Substantially the same procedure as in Example 8 was repeated using 3.50 g (9.45 mmol) of Compound 144 obtained in Reference Example 87 in place of Compound 64. Then, the resultant crude crystals were recrystallized from hexane/ethyl acetate to give 3.39 g (yield 93%) of Compound as pale yellow plates.

Melting Point: 163.9°–164.7° C.; Elemental Analysis: $C_{20}H_{24}N_4O_4$, Calcd. (%): C, 62.49; H, 6.29; N, 14.57; Found (%): C, 62.21; H, 6.27; N, 14.58; IR (KBr) $v_{max}$ (cm$^{-1}$): 1688, 1651, 1510, 1238; NMR (270 MHz; CDCl$_3$)δ(ppm): 7.75(1H, d, J=15.8 Hz), 7.53(2H, d, J=8.6 Hz), 7.07(2H, d, J=S.6 Hz), 6.79 (1H, d, J=15.8 Hz), 5.21 (2H, s), 4.21 (2H, q, J=6.9 Hz), 4.09 (2H, q, J=6.9 Hz), 4.05 (3H, s), 3.50 (3H, s), 1.38(3H, t, J=6.9 Hz), 1.26(3H, t, J=6.9 Hz).

REFERENCE EXAMPLE 89

(E)-1,3-Diethyl-8-(4-fluorostyryl)xanthine (Compound 146)

Substantially the same procedure as in Example 7 was repeated using 2.50 g (12.6 mmol) of 5,6-diamino-1,3-diethyluracil and 2.31 g (13.9 mmol) of 4-fluorocinnamic acid. Then, the resultant crude crystals were recrystallized from tetrahydrofuran/water to give 2.00 g (yield 51%) of Compound 146 as colorless columns.

Melting Point: >270° C.; Elemental Analysis: $C_{17}H_{17}FN_4O_2$, Calcd. (%): C, 62.19; H, 5.22; N, 17.06; Found (%): C, 62.02; H, 5.12; N, 17.02; IR (KBr) $v_{max}$ (cm$^{-1}$): 1689, 1560, 1508; NMR (270 MHz; DMSO-$d_6$)δ(ppm): 8.06(1H, d, J=16.3 Hz), 7.72(2H, dd, J=8.6, 5.2 Hz), 7.21(2H, t, J=8.6 Hz), 7.10(1H, d, J=16.3 Hz), 4.43–4.30(4H, m), 1.53(3H, t, J=7.2 Hz), 1.41(3H, t, J=7.2 Hz).

REFERENCE EXAMPLE 90

(E)-1,3-Diethyl-8-(4-fluorostyryl)-7-methylxanthine (Compound 147)

Substantially the same procedure as in Example 8 was repeated using 1.80 g (5.18 mmol) of Compound 146 obtained in Reference Example 89 in place of Compound 64. Then, the resultant crude crystals were recrystallized from toluene/cyclohexane to give 510 mg (yield 29%) of Compound 147 as white needles.

Melting Point: 182.0°–182.5° C.; Elemental Analysis: $C_{18}H_{19}FN_4O_2$, Calcd. (%): C, 63.15; H, 5.59; N, 16.36; Found (%): C, 63.18; H, 5.61; N, 16.40; IR (KBr) $v_{max}$ (cm$^{-1}$): 1687, 1654, 1514; NMR (270 MHz; DMSO-$d_6$)δ(ppm): 7.88(2H, dd, J=8.1, 5.8 Hz), 7.67(1H, d, J=15.8 Hz), 7.41–7.24(3H, m), 4.11–4.03 (2H, m), 4.03 (3H, s), 3.92 (2H, q, J=6.8 Hz), 1.26(3H, t, J=6.9 Hz), 1.13(3H, t, J=6.8 Hz).

REFERENCE EXAMPLE 91

(E)-8-[3,5-Bis(trifluoromethyl)styryl]-1,3-diethylxanthine (Compound 148)

Substantially the same procedure as in Example 7 was repeated using 3.00 g (15.1 mmol) of 5,6-diamino-1,3-diethyluracil and 4.73 g (16.7 mmol) of 3,5-bis(trifluoromethyl)cinnamic acid. Then, the resultant crude crystals were recrystallized from dioxane to give 4.09 g (yield 61%) of Compound 148 as pale yellow needles.

Melting Point: >280° C.; Elemental Analysis: $C_{19}H_{16}F_6N_4O_2$, Calcd. (%): C, 51.13; H, 3.61; N, 12.55; Found (%): C, 50.96; H, 3.40; N, 12.52; IR (KBr) $v_{max}$ (cm$^{-1}$): 1694, 1649, 1495, 1287; NMR (270 MHz; DMSO-$d_6$)$\delta$(ppm): 13.75(1H, brs), 8.35 (2H, s), 8.05(1H, s), 7.80(1H, d, J=16.5 Hz), 7.40 (1H, d, J=16.5 Hz), 4.08(2H, q, J=6.9 Hz), 3.94(2H, q, J=6.9 Hz), 1.27(3H, t, J=6.9 Hz), 1.14(3H, t, J=6.9 Hz).

REFERENCE EXAMPLE 92

(E)-8-[3,5-Bis(trifluoromethyl)styryl]-1,3-diethyl-7-methylxanthine (Compound 149)

Substantially the same procedure as in Example 8 was repeated using 2.00 g (4.68 mmol) of Compound 148 obtained in Reference Example 91 in place of Compound 64. Then, the resultant crude crystals were recrystallized from dioxane/water to give 1.43 g (yield 69%) of Compound 149 as pale green needles.

Melting Point: 204.9°–205.1° C.; MS-EI m/e: 460(M$^+$); IR (KBr) $v_{max}$ (cm$^{-1}$): 1699, 1653, 1546, 1282; NMR (270 MHz; CDCl$_3$)$\delta$(ppm): 8.55 (2H, s), 8.01 (1H, s), 7.85 (1H, d, J=15.8 Hz), 7.72 (1H, d, J=15.8 Hz), 4.09 (3H, s), 4.08(2H, q, J=6.9 Hz), 3.93(2H, q, J=6.9 Hz), 1.28(3H, t, J=6.9 Hz), 1.14(3H, t, J=6.9 Hz).

REFERENCE EXAMPLE 93

(E)-8-(3,5-Difluorostyryl)-1,3-diethylxanthine (Compound 150)

Substantially the same procedure as in Example 7 was repeated using 3.00 g (15.1 mmol) of 5,6-diamino-1,3-diethyluracil and 3.06 g (16.6 mmol) of 3,5-difluorocinnamic acid. Then, the resultant crude crystals were recrystallized from dioxane/water to give 3.30 g (yield 63%) of Compound 150 as pale yellow plates.

Melting Point: >280° C.; Elemental Analysis: $C_{17}H_{16}F_2N_4O_2$, Calcd. (%): C, 58.96; H, 4.65; N, 16.18; Found (%): C, 58.82; H, 4.65; N, 16.07; IR (KBr) $v_{max}$ (cm$^{-1}$): 1686, 1634, 1589, 1489; NMR (270 MHz; DMSO-$d_6$)$\delta$(ppm): 13.66 (1H, brs), 7.60 (1H, d, J=16.5 Hz), 7.36(2H, dd, J=8.6, 2.0 Hz), 7.20(1H, dt, J=9.2, 2.0 Hz), 7.16(1H, d, J=16.5 Hz), 4.07 (2H, q, J=6.9 Hz), 3.94 (2H, q, J=6.9Hz), 1.26 (3H, t, J=6.9 Hz), 1.14(3H, t, J=6.9 Hz).

REFERENCE EXAMPLE 94

(E)-8-(3,5-Difluorostyryl)-1,3-diethyl-7-methylxanthine (Compound 151)

Substantially the same procedure as in Example 8 was repeated using 2.00 g (5.78 mmol) of Compound 150 obtained in Reference Example 93 in place of Compound 64. Then, the resultant crude crystals were recrystallized from hexane/ethyl acetate to give 1.80 g (yield 87%) of Compound 151 as pale yellow needles.

Melting Point: 177.0°–178.6° C.; MS-EI m/e: 360(M$^+$); IR (KBr) $v_{max}$ (cm$^{-1}$): 1683, 1619, 1593, 1543; NMR (270 MHz; CDCl$_3$)$\delta$(ppm): 7.70(1H, d, J=15.5 Hz), 7.09(2H, dd, J=8.3, 2.0 Hz), 6.91(1H, d, J=15.5 Hz), 6.81(1H, dt, J=8.6, 2.0 Hz), 4.21(2H, q, J=6.9 Hz), 4.09 (2H, q, J=6.9 Hz), 4.08 (3H, s), 1.38 (3H, t, J=6.9 Hz), 1.27 (3H, t, J=6.9 Hz).

REFERENCE EXAMPLE 95

(E)-1,3-Diethyl-8-(3-nitrostyryl)xanthine (Compound 152)

Substantially the same procedure as in Example 7 was repeated using 2.5 g (12.6 mmol) of 5,6-diamino-1,3-diethyluracil and 2.68 g (13.9 mmol) of 3-nitrocinnamic acid. Then, the resultant crude crystals were recrystallized from dioxane/water to give 2.01 g (yield 30%) of Compound 152 as a yellow powder.

Melting Point: >270° C.; Elemental Analysis: $C_{17}H_{17}N_5O_4 \cdot 0.25 C_4H_8O_2$, Calcd. (%): C, 57.29; H, 5.07; N, 18.56; Found (%): C, 57.38; H, 5.06; N, 18.63; IR (KBr) $v_{max}$ (cm$^{-1}$): 1688, 1640, 1530; NMR (270 MHz; DMSO-$d_6$)$\delta$(ppm): 8.42(1H, d, J=1.7 Hz), 8.18(1H, dd, J=8.3, 1.7 Hz), 8.12(1H, d, J=7.9 Hz), 7.75(1H, d, J=16.5 Hz), 7.71(1H, t, J=7.9 Hz), 7.24 (1H, d, J=16.5 Hz), 4.08(2H, q, J=7.0 Hz), 3.94(2H, q, J=7.0 Hz), 1.27(3H, t, J=7.0 Hz), 1.14(3H, t, J=7.0 Hz).

REFERENCE EXAMPLE 96

(E)-1,3-Diethyl-7-methyl-8-(3-nitrostyryl)xanthine (Compound 153)

Substantially the same procedure as in Example 8 was repeated using 700 mg (1.97 mmol) of Compound 152 obtained in Reference Example 95 in place of Compound 64. Then, the resultant crude crystals were recrystallized from acetonitrile to give 340 mg (yield 47%) of Compound 153 as a yellow powder.

Melting Point: 250.5°–251.7° C.; Elemental Analysis: $C_{18}H_{19}N_5O_4$, Calcd. (%): C, 58.53; H, 5.18; N, 18.96; Found (%): C, 58.47; H, 5.13; N, 18.89; IR (KBr) $v_{max}$ (cm$^{-1}$): 1699, 1666, 1524; NMR (270 MHz; DMSO-$d_6$)$\delta$(ppm): 8.72(1H, s), 8.25(1H, d, J=7.9 Hz), 8.19(1H, d, J=7.4 Hz), 7.79(1H, d, J=15.88 Hz), 7.72(1H, t, J=7.9 Hz), 7.63(1H, d, J=15.8 Hz), 4.12–4.05(2H, m), 4.08(3H, s), 3.93(2H, q, J=7.2 Hz), 1.27(3H, t, J=7.2 Hz), 1.13(3H, t, J=7.2 Hz).

REFERENCE EXAMPLE 97

(E)-8-(3-Bromostyryl)-1,3-diethylxanthine (Compound 154)

Substantially the same procedure as in Example 7 was repeated using 2.0 g (10.1 mmol) of 5,6-diamino-1,3-diethyluracil and 2.52 g (11.1 mmol) of 3-bromocinnamic acid. Then, the resultant crude crystals were recrystallized from tetrahydrofuran/water to give 2.01 g (yield 37%) of Compound 154 as pale green plates.

Melting Point: >270° C.; Elemental Analysis: $C_{17}H_{17}BrN_4O_2$, Calcd. (%): C, 52.46; H, 4.40; N, 14.39; Found (%): C, 52.54; H, 4.44; N, 14.37; IR (KBr) $v_{max}$ (cm$^{-1}$): 1683, 1636, 1492; NMR (270 MHz; CF$_3$COOD)$\delta$(ppm): 7.99 (1H, d, J=16.6 Hz), 7.84(1H, s), 7.70(1H, d, J=7.9 Hz), 7.62(1H, d, J=7.9 Hz), 7.40 (1H, t, J=7.9 Hz), 7.19 (1H, d, J=16.6 Hz), 4.40–4.30(4H, m), 1.53(3H, t, J=7.2 Hz), 1.41(3H, t, J=7.2 Hz).

REFERENCE EXAMPLE 98

(E)-8-(3-Bromostyryl)-1,3-diethyl-7-methylxanthine (Compound 155)

Substantially the same procedure as in Example 8 was repeated using 2.5 g (6.43 mmol) of Compound 154 obtained in Reference Example 97 in place of Compound 64. Then, the resultant crude crystals were recrystallized from toluene/cyclohexane to give 600 mg (yield 69%) of Compound 155 as a yellow powder.

Melting Point: 187.3°–188.2° C.; Elemental Analysis: $C_{18}H_{19}BrN_4O_2$, Calcd. (%): C, 53.61; H, 4.75; N, 13.89; Found (%): C, 53.83; H, 4.63; N, 13.70; IR (KBr) $v_{max}$ (cm$^{-1}$): 1694, 1654; NMR (270 MHz; DMSO-d$_6$)δ(ppm): 8.13(1H, s), 7.76(1H, d, J=7.6 Hz), 7.63 (1H, d, J=15.8 Hz), 7.54 (1H, d, J=8.9 Hz), 7.46(1H, d, J=15.8 Hz), 7.37(1H, t, J=8.2 Hz), 4.11–4.03 (2H, m), 4.05 (3H, s), 3.92 (2H, q, J=6.9 Hz), 1.26(3H, t, J=6.9 Hz), 1.13(3H, t, J=6.9 Hz).

REFERENCE EXAMPLE 99

(E)-1,3-Diethyl-8-(3-trifluoromethylstyryl)xanthine (Compound 156)

Substantially the same procedure as in Example 7 was repeated using 2.50 g (12.6 mmol) of 5,6-diamino-1,3-diethyluracil and 3.0 g (13.9 mmol) of 3-trifluoromethylcinnamic acid. Then, the resultant crude crystals were recrystallized from acetonitrile/water to give 2.07 g (yield of Compound 156 as white needles.

Melting Point: >270° C.; Elemental Analysis: $C_{18}H_{17}F_3N_4O_2$, Calcd. (%): C, 57.14; H, 4.53; N, 14.81; Found (%): C, 57.15; H, 4.47; N, 14.65; IR (KBr) $v_{max}$ (cm$^{-1}$): 1691, 1641, 1495, 1334; NMR (270 MHz; DMSO-d$_6$)δ(ppm): 13.65 (1H, brs), 7.99– 7.95(2H, m), 7.76–7.63(3H, m), 7.21(1H, d, J=16.1 Hz), 4.07 (2H, q, J=6.9 Hz), 3.94 (2H, q, J=6.7 Hz), 1.27 (3H, t, J=6.9 Hz), 1.14 (3H, t, J=6.7 Hz).

REFERENCE EXAMPLE 100

(E)-1,3-Diethyl-7-methyl-8-(3-trifluoromethylstyryl)xanthine (Compound 157)

Substantially the same procedure as in Example 8 was repeated using 1.70 g (4.50 mmol) of Compound 156 obtained in Reference Example 99 in place of Compound 64. Then, the resultant crude crystals were recrystallized from toluene/cyclohexane to give 1.14 g (yield 65%) of Compound as a pale yellow powder.

Melting Point: 214.8–215.3° C.; Elemental Analysis: $C_{19}H_{19}F_3N_4O_2$, Calcd. (%): C, 58.16; H, 4.88; N, 14.28; Found (%): C, 58.13; H, 4.90; N, 14.22; IR (KBr) $v_{max}$ (cm$^{-1}$): 1697, 1664; NMR (270 MHz; DMSO-d$_6$)δ(ppm): 8.26(1H, s), 8.09(1H, d, J=7.4 Hz), 7.75(1H, d, J=15.8 Hz), 7.69–7.62(2H, m), 7.56 (1H, d, J=15.8 Hz), 4.12–4.00 (2H, m), 4.07 (3H, s), 3.92 (2H, q, J=6.9 Hz), 1.27 (3H, t, J=6.9 Hz), 1.13 (3H, t, J=6.9 Hz).

REFERENCE EXAMPLE 101

(E)-1,3-Diethyl-8-(2-fluorostyryl)xanthine (Compound 160)

Substantially the same procedure as in Example 7 was repeated using 2.70 g (13.6 mmol) of 5,6-diamino-1,3-diethyluracil and 2.49 g (15.0 mmol) of 2-fluorocinnamic acid. Then, the resultant crude crystals were recrystallized from dioxane/water to give 1.81 g (yield 41%) of Compound 160 as a white powder.

Melting Point: >270° C.; Elemental Analysis: $C_{17}H_{17}FN_4O_2$, Calcd. (%): C, 62.19; H, 5.22; N, 17.06; Found (%): C, 62.31; H, 5.23; N, 17.09; IR (KBr) $v_{max}$ (cm$^{-1}$): 1687, 1650, 1557, 1498, 1451; NMR (270 MHz; DMSO-d$_6$)δ(ppm): 7.81(1H, t, J=7.9 Hz), 7.72 (1H, d, J=16.3 Hz), 7.42–7.25(3H, m), 7.15(1H, d, J=16.3 Hz), 4.07 (2H, q, J=6.9 Hz), 3.94(2H, q, J=6.9 Hz), 1.26(3H, t, J=6.9 Hz), 1.14 (3H, t, J=6.9 Hz).

REFERENCE EXAMPLE 102

(E)-1,3-Diethyl-8-(2-fluorostyryl)-7-methylxanthine (Compound 161)

Substantially the same procedure as in Example 8 was repeated using 1.30 g (3.96 mmol) of Compound 160 obtained in Reference Example 101 in place of Compound 64. Then, the resultant crude crystals were recrystallized from toluene/cyclohexane to give 440 mg (yield 32%) of Compound as white needles.

Melting Point: 184.1°–184.6° C.; Elemental Analysis: $C_{18}H_{19}FN_4O_2$, Calcd. (%): C, 63.15; H, 5.59; N, 16.36; Found (%): C, 63.01; H, 5.61; N, 16.27; IR (KBr) $v_{max}$ (cm$^{-1}$): 1697, 1668, 1541; NMR (270 MHz; DMSO-d$_6$)δ(ppm): 8.04(1H, t, J=8.4 Hz), 7.77 (1H, d, J=15.8 Hz), 7.47–7.43 (1H, m), 7.45 (1H, d, J=15.8 Hz), 7.35–7.27 (2H, m), 4.11–4.04 (2H, m), 4.04(3H, s), 3.92(2H, q, J=7.0 Hz), 1.26(3H, t, J=6.9 Hz), 1.13 (3H, t, J=7.0 Hz).

REFERENCE EXAMPLE 103

(E)-8-[4-(N,N-Dimethylamino)styryl]-1,3-diethylxanthine (Compound 162)

Substantially the same procedure as in Example 7 was repeated using 3.00 g (15.1 mmol) of 5,6-diamino-1,3-diethyluracil and 3.30 g (17.3 mmol) of 4-(N,N-dimethylamino)cinnamic acid. Then, the resultant crude crystals were recrystallized from dioxane to give 2.78 g (yield 52%) of Compound 162 as yellow needles.

Melting Point: >300° C.; Elemental Analysis: $C_{19}H_{23}N_5O_2$, Calcd. (%): C, 64.57; H, 6.56; N, 19.82; Found (%): C, 64.78; H, 6.73; N, 19.94; IR (KBr) $v_{max}$ (cm$^{-1}$): 1691, 1650, 1606, 1530; NMR (270 MHz; DMSO-d$_6$)δ(ppm): 13.20(1H, brs), 7.54 (1H, d, J=16.2 Hz), 7.44(2H, d, J=8.6 Hz), 6.75(1H, d, J=16.2 Hz), 6.74(2H, d, J=8.6 Hz), 4.06(2H, q, J=6.9 Hz), 3.94(2H, q, J=6.9 Hz), 2.97(6H, s), 1.26 (3H, t, J=6.9 Hz), 1.14(3H, t, J=6.9 Hz).

REFERENCE EXAMPLE 104

(E)-1,3-Diethyl-8-(4-phenylstyryl)xanthine (Compound 163)

Substantially the same procedure as in Example 7 was repeated using 2.50 g (12.6 mmol) of 5,6-diamino-1,3-diethyluracil and 3.12 g (13.9 mmol) of 4-phenylcinnamic acid. Then, the resultant crude crystals were recrystallized from dioxane/water to give 1.90 g (yield 39%) of Compound 163 as yellow flocculent precipitates.

Melting Point: >270° C.; Elemental Analysis: $C_{23}H_{22}N_4O_2 \cdot 0.25H_2O$, Calcd. (%): C, 70.66; H, 5.80; N, 14.33; Found (%): C, 70.90; H, 5.75; N, 14.32; IR (KBr) $v_{max}$ (cm$^{-1}$): 1689, 1639, 1492; NMR (270 MHz; DMSO-$d_6$)δ(ppm): 7.80–7.65(7H, m), 7.49 (2H, t, J=7.3 Hz), 7.39(1H, t, J=7.3 Hz), 7.10(1H, d, J=16.3 Hz), 4.07(2H, q, J=7.1 Hz), 3.94(2H, q, J=6.8 Hz), 1.27 (3H, t, J=7.1 Hz), 1.14 (3H, t, J=6.8 Hz).

REFERENCE EXAMPLE 105

(E)-1,3-Diethyl-7-methyl-8-(4-phenylstyryl)xanthine (Compound 164)

Compound 163 (1.50 g, 3.89 mmol) obtained in Reference Example 104 was suspended in a mixed solvent of 13 ml of water, 3.9 ml of a 2N aqueous solution of sodium hydroxide, and 7 ml of methanol. To the suspension was dropwise added 0.55 ml (5.83 mmol) of dimethyl sulfate, and the resultant mixture was stirred at 60° C.; for 4 hours. Water (10 ml) was added thereto, and the deposited crystals were collected by filtration and dried. The obtained crude crystals were purified by silica gel column chromatography, followed by recrystallization from ethyl acetate to give 480 mg (yield 28%) of Compound 164 as yellow columns.

Melting Point: 200.5°–201.3° C.; Elemental Analysis: $C_{24}H_{24}N_4O_2 \cdot 0.5CH_3CO_2C_2H_5$, Calcd. (%): C, 70.25; H, 6.35; N, 12.72; Found (%): C, 70.36; H, 6.47; N, 12.60; IR (KBr) $v_{max}$ (cm$^{-1}$): 1685, 1649, 1541; NMR (270 MHz; DMSO-$d_6$)δ(ppm): 7.95 (1H, d, J=14.8 Hz), 7.76–7.69 (6H, m), 7.52–7.45(3H, m), 7.39(1H, t, J=6.4 Hz), 4.12–3.99 (2H, m), 4.06 (3H, s), 3.92 (2H, q, J=6.9 Hz), 1.27(3H, t, J=6.9 Hz), 1.14 (3H, t, J=7.0 Hz).

REFERENCE EXAMPLE 106

(E)-1,3-Diethyl-8-(3-fluoro-4-methoxystyryl)xanthine (Compound 165)

Substantially the same procedure as in Example 7 was repeated using 2.50 g (12.6 mmol) of 5,6-diamino-1,3-diethyluracil and 2.72 g (13.9 mmol) of 3-fluoro-4-methoxycinnamic acid. Then, the resultant crude crystals were recrystallized from dioxane/water to give 1.97 g (yield of Compound 165 as pale yellow flocculent precipitates.

Melting Point: >270° C.; Elemental Analysis: $C_{18}H_{19}FN_4O_3$, Calcd. (%): C, 60.33; H, 5.34; N, 15.63; Found (%): C, 59.99; H, 5.34; N, 15.57; IR (KBr) $v_{max}$ (cm$^{-1}$): 1694, 1644, 1520, 1491; NMR (270 MHz; DMSO-$d_6$)δ(ppm): 7.61–7.54 (2H, m), 7.40 (1H, d, J=8.8 Hz), 7.21 (1H, t, J=8.8 Hz), 6.93 (1H, d, J=16.3 Hz), 4.06 (2H, q, J=7.1 Hz), 3.97–3.88 (2H, m), 3.88 (3H, s), 1.25 (3H, t, J=7.2 Hz), 1.14 (3H, t, J=7.1 Hz).

REFERENCE EXAMPLE 107

(E)-1,3-Diethyl-8-(3-fluoro-4-methoxystyryl)-7-methylxanthine (Compound 166)

Substantially the same procedure as in Example 8 was repeated using 1.50 g (4.19 mmol) of Compound 165 obtained in Reference Example 106 in place of Compound 64. Then, the resultant crude crystals were recrystallized from toluene/ethanol to give 1.22 g (yield 78%) of Compound 166 as a pale yellow powder.

Melting Point: 211.7°–212.2° C.; Elemental Analysis: $C_{19}H_{21}FN_4O_3 \cdot 0.25H_2O$, Calcd. (%): C, 60.55; H, 5.75; N, 14.87; Found (%): C, 60.75; H, 5.81; N, 14.92; IR (KBr) $v_{max}$ (cm$^{-1}$): 1694, 1653, 1544, 1520, 1459; NMR (270 MHz; DMSO-$d_6$)δ(ppm): 7.82(1H, dd, J=12.9, 2.0 Hz), 7.59(1H, d, J=15.8Hz), 7.56–7.52(1H, m), 7.26(1H, d, J=15.8 Hz), 7.19(1H, t, J=8.9 Hz), 4.10– 4.02 (2H, m), 4.02 (3H, s), 3.94–3.88 (2H, m), 3.88 (3H, s), 1.25 (3H, t, J=6.9Hz), 1.13 (3H, t, J=6.9 Hz).

REFERENCE EXAMPLE 108

(E)-8-(3-Chloro-4-fluorostyryl)-1,3-diethylxanthine (Compound 167)

Substantially the same procedure as in Example 7 was repeated using 2.50 g (12.6 mmol) of 5,6-diamino-1,3-diethyluracil and 3.01 g (15.1 mmol) of 3-chloro-4-fluorocinnamic acid. Then, the resultant crude crystals were recrystallized from tetrahydrofuran/water to give 560 mg (yield 32%) of Compound 167 as a white powder.

Melting Point: >270° C.; Elemental Analysis: $C_{17}H_{16}ClFN_4O_2$, Calcd. (%): C, 56.28; H, 4.45; N, 15.44; Found (%): C, 56.30; H, 4.43; N, 15.53; IR (KBr) $v_{max}$ (cm$^{-1}$): 1695, 1649, 1504; NMR (270 MHz; DMSO-$d_6$)δ(ppm): 7.93–7.91(1H, m), 7.66– 7.63(1H, m), 7.58(1H, d, J=16.3 Hz), 7.46(1H, t, J=8.9 Hz), 7.08(1H, d, J=16.3 Hz), 4.05(2H, q, J=7.1 Hz), 3.93(2H, q, J=6.8 Hz), 1.26(3H, t, J=7.1 Hz), 1.14 (3H, t, J=6.8 Hz).

REFERENCE EXAMPLE 109

(E)-8-(3-Chloro-4-fluorostyryl)-1,3-diethyl-7-methylxanthine (Compound 168)

Substantially the same procedure as in Example 8 was repeated using 1.80 g (4.98 mmol) of Compound 167 obtained in Reference Example 108 in place of Compound 64. Then, the resultant crude crystals were recrystallized from ethyl acetate to give 820 mg (yield 44%) of Compound 168 as yellow needles.

Melting Point: 218.4°–219.1° C.; Elemental Analysis: $C_{18}H_{18}ClFN_4O_2$, Calcd. (%): C, 57.37; H, 4.81; N, 14.87; Found (%): C, 57.23; H, 4.85; N, 14.81; IR (KBr) $v_{max}$ (cm$^{-1}$): 1693, 1648, 1541, 1505, 1438; NMR (270 MHz; DMSO-$d_6$)δ(ppm): 8.18(1H, dd, J=7.2, 2.3 Hz), 7.84–7.79(1H, m), 7.63(1H, d, J=15.8 Hz), 7.51–7.44 (2H, m), 4.11–3.99 (2H, m), 4.05 (3H, s), 3.92(2H, q, J=6.9Hz), 1.25(3H, t, J=6.9 Hz), 1.13 (3H, t, J=6.9 Hz).

REFERENCE EXAMPLE 110

(E)-1,3-Diethyl-8-(3-fluoro-2-methylstyryl)xanthine (Compound 171)

Substantially the same procedure as in Example 7 was repeated using 2.50 g (12.6 mmol) of 5,6-diamino-1,3-diethyluracil and 2.50 g (13.9 mmol) of 3-fluoro-2-methylcinnamic acid. Then, the resultant crude crystals were recrystallized from dioxane to give 2.18 g (yield 51%) of Compound 171 as a white powder.

Melting Point: >270° C.; Elemental Analysis: $C_{18}H_{19}FN_4O_2$, Calcd. (%): C, 63.15; H, 5.59; N, 16.36; Found (%): C, 62.81; H, 5.71; N, 16.09; IR (KBr) $v_{max}$ (cm$^{-1}$): 1696, 1658, 1499; NMR (270 MHz; DMSO-$d_6$)δ(ppm): 13.7 (1H, brs), 7.87 (1H, d, J=16.6 Hz), 7.59 (1H, d, J=7.4 Hz), 7.31–7.23 (1H, m), 7.15(1H, t, J=8.7 Hz), 7.05 (1H, d, J=16.6 Hz), 4.06 (2H, q, J=6.9 Hz), 3.94 (2H, q, J=6.9 Hz), 2.33 (3H, d, J=2.0 Hz), 1.26(3H, t, J=7.1 Hz), 1.14 (3H, t, J=6.9 Hz).

REFERENCE EXAMPLE 111

(E)-1,3-Diethyl-8-(3-fluoro-2-methylstyryl)-7-methylxanthine (Compound 172)

Substantially the same procedure as in Example 8 was repeated using 1.30 g (3.80 mmol) of Compound 171 obtained in Reference Example 110 in place of Compound 64. Then, the resultant crude crystals were recrystallized from 2-propanol/water to give 1.12 g (yield 83%) of Compound 172 as white flocculent precipitates.

Melting Point: 198.1°–198.7° C.; Elemental Analysis: $C_{19}H_{21}FN_4O_2 \cdot 0.5H_2O$, Calcd. (%): C, 62.45; H, 6.07; N, 15.33; Found (%): C, 62.39; H, 6.26; N, 15.25; IR (KBr) $v_{max}$ (cm$^{-1}$): 1695, 1654, 1543; NMR (270 MHz; DMSO-$d_6$)δ(ppm): 7.85(1H, d, J=15.5 Hz), 7.75(1H, d, J=7.9 Hz), 7.34–7.27(1H, m), 7.29(1H, d, J=15.5 Hz), 7.18(1H, t, J=8.9 Hz), 4.12–4.04(2H, m), 4.04 (3H, s), 3.92 (2H, q, J=6.9 Hz), 2.32 (3H, d, J=1.7Hz), 1.27(3H, t, J=7.1 Hz), 1.13(3H, t, J=6.9 Hz).

REFERENCE EXAMPLE 112

(E)-8-(3,4-Dihydroxystyryl)-1,3-diethyl-7-methylxanthine (Compound 173)

Compound 65 (2.00 g, 5.20 mmol) obtained in Example 8 was dissolved in 40 ml of methylene chloride. To the solution was added 26 ml (26 mmol) of boron tribromide (1.0M methylene chloride solution) under ice cooling in argon atmosphere, and the mixture was stirred overnight at room temperature. Methanol was added thereto and the mixture was separated with chloroform-an aqueous solution of sodium bicarbonate. The organic layer was washed with a saturated aqueous solution of sodium chloride and dried over anhydrous sodium sulfate, followed by evaporation under reduced pressure. The residue was recrystallized from ethanol to give 643 mg (yield 35%) of Compound 173 as pale yellow grains.

Melting Point: 247.5°–248.2° C.; MS-EI m/e: 356(M$^+$); IR (KBr) $v_{max}$ (cm$^{-1}$): 1675, 1642, 1543, 1520, 1298; NMR (270 MHz; DMSO-$d_6$)δ(ppm): 9.31(1H, brs), 8.95(1H, brs), 7.50(1H, d, J=15.8 Hz), 7.16(1H, s), 7.05(1H, d, J=7.9 Hz), 7.00(1H, d, J=15.8 Hz), 6.77(1H, d, J=7.9 Hz), 4.06 (2H, q, J=6.9 Hz), 3.99 (3H, s), 3.92 (2H, q, J=6.9 Hz), 1.25(3H, t, J=6.9 Hz), 1.13(3H, t, J=6.9 Hz).

REFERENCE EXAMPLE 113

(E)-1,3-Diethyl-8-(3-hydroxy-4-methoxystyryl)-7-methylxanthine (Compound 174)

Compound 173 (400 mg, 1.12 mmol) obtained in Reference Example 112 was dissolved in 8 ml of dimethylformamide. To the solution were added 0.35 ml (5.62 mmol) of methyl iodide and 415 mg (5.62 mmol) of lithium carbonate, and the mixture was stirred at 80° C. for 3.5 hours. Water was added thereto to dissolve lithium carbonate, followed by addition of chloroform. The organic layer was washed with a saturated aqueous solution of sodium chloride and dried over anhydrous sodium sulfate, followed by evaporation under reduced pressure. The residue was purified by silica gel column chromatography (eluent: chloroform) to give 127 mg (yield 76%) of Compound 174 as a pale brown powder. The obtained crude crystals were further recrystallized from ethanol.

Melting Point: 204.5°–205.8° C.; MS-EI m/e: 370(M$^+$); IR (KBr) $v_{max}$ (cm$^{-1}$): 1689, 1653, 1515, 1442; NMR (270 MHz; DMSO-$d_6$)δ(ppm): 9.06(1H, s), 7.53(1H, d, J=15.5 Hz), 7.23(1H, s), 7.17(1H, d, J=8.3 Hz), 7.08 (1H, d, J=15.5 Hz), 6.96 (1H, d, J=8.3 Hz), 4.06 (2H, q, J=6.9 Hz), 4.00(3H, s), 3.92(2H, q, J=6.9 Hz), 3.82(3H, s), 1.25(3H, t, J=6.9 Hz), 1.13 (3H, t, J=6.9 Hz).

REFERENCE EXAMPLE 114

(E)-1,3-Diethyl-8-(4-hydroxystyryl)-7-methylxanthine (Compound 175)

Compound 145 (2.70 g, 7.02 mmol) obtained in Reference Example 88 was dissolved in 50 ml of tetrahydrofuran. To the solution was added 17.6 ml of 2N hydrochloric acid, and the mixture was heated under reflux for 2.5 hours. The reaction solution was neutralized with a 2N aqueous solution of sodium hydroxide under ice cooling, water was added thereto, and the deposited crystals were collected by filtration. The obtained crude crystals were recrystallized from 2-propanol to give 2.33 g (yield 98%) of Compound 175 as yellow grains.

Melting Point: >270° C.; Elemental Analysis: $C_{18}H_{20}N_4O_3$, Calcd. (%): C, 63.52; H, 5.92; N, 16.46; Found (%): C, 63.17; H, 6.02; N, 16.18; IR (KBr) $v_{max}$ (cm$^{-1}$): 1696, 1636, 1607, 1517; NMR (270 MHz; DMSO-$d_6$)δ(ppm): 9.79(1H, s), 7.62(2H, d, J=8.3 Hz), 7.58(1H, d, J=15.8 Hz), 7.08(1H, d, J=15.8 Hz), 6.81 (2H, d, J=8.3 Hz), 4.07 (2H, q, J=6.9 Hz), 3.99 (3H, s), 3.92 (2H, q, J=6.9 Hz), 1.26 (3H, t, J=6.9 Hz), 1.13(3H, t, J=6.9 Hz).

REFERENCE EXAMPLE 115

(E)-8-(4-Benzyloxystyryl)-1,3-diethyl-7-methylxanthine (Compound 176)

Compound 175 (100 mg, 0.29 mmol) obtained in Reference Example 114 was dissolved in 2 ml of dimethylformamide. To the solution were added 162 mg (1.17 mmol) of potassium carbonate and 0.28 ml (2.35 mmol) of benzyl bromide, and the mixture was stirred at 80° C. for 2.5 hours. Water was added thereto under ice cooling to dissolve potassium carbonate and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was recrystallized from hexane/ethyl acetate to give 67 mg (yield 53%) of Compound 176 as yellow needles.

Melting Point: 184.7°–185.4° C.; Elemental Analysis: $C_{25}H_{26}N_4O_3$, Calcd. (%): C, 69.75; H, 6.08; N, 13.01; Found (%): C, 69.70; H, 6.26; N, 12.79; IR (KBr) $v_{max}$ (cm$^{-1}$): 1688, 1655, 1513, 1245; NMR (270 MHz; CDCl$_3$)δ(ppm): 7.74(1H, d, J=15.8 Hz), 7.53 (1H, d, J=8.9 Hz), 7.47–7.32 (5 H, m), 7.01 (2H, d, J=8.9 Hz), 6.78 (1H, d, J=15.8 Hz), 5.11 (2H, s), 4.21 (2H, q, J=6.9 Hz), 4.09 (2H, q, J=6.9 Hz), 4.04 (3H, s), 1.38(3H, t, J=6.9 Hz), 1.26(3H, t, J=6.9 Hz).

REFERENCE EXAMPLE 116

(E)-8-[ 4-(4 -Bromobutoxy)styryl ]-1,3-diethyl-7-methylxanthine (Compound 177)

Compound 175 (200 mg, 0.59 mmol) obtained in Reference Example 114 was dissolved in 4 ml of dimethylformamide. To the solution were added 163 mg (1.18 mmol) of potassium carbonate and 0.56 ml (1.18 mmol) of 1,4-dibromobutane, and the mixture was stirred at 50° C. for 4 hours. Water was added thereto under ice cooling to dissolve potassium carbonate and the deposited crystals were collected by filtration. The obtained crude crystals were recrystallized from hexane/ethyl acetate to give 170 mg (yield 61%) of Compound 177 as pale yellow grains.

Melting Point: 174.8°–176.4° C.; Elemental Analysis: $C_{22}H_{27}BrN_4O_3$, Calcd. (%): C, 55.59; H, 5.72; N, 11.79; Found (%): C, 55.68; H, 5.85; N, 11.69; IR (KBr) $v_{max}$ (cm$^{-1}$): 1688, 1656, 1515, 1244; NMR (270 MHz; CDCl$_3$)δ(ppm): 7.74(1H, d, J=15.8 Hz), 7.53 (2H, d, J=8.9 Hz), 6.92 (2H, d, J=8.9 Hz), 6.77 (1H, d, J=15.8 Hz), 4.21(2H, q, J=6.9 Hz), 4.13–4.02 (4H, m), 4.04(3H, s), 3.50(2H, t, J=6.6 Hz), 2.14– 1.93(4H, m), 1.38(3H, t, J=6.9 Hz), 1.26(3H, t, J=6.9 Hz).

REFERENCE EXAMPLE 117

(E)-8-[4-(4-Azidobutoxy)styryl]-1,3-diethyl-7-methylxanthine (Compound 178)

Compound 177 (235 mg, 0.49 mmol) obtained in Reference Example 116 was dissolved in 10 ml of dimethylformamide. To the solution was added 161 mg (2.48 mmol) of sodium azide, and the mixture was stirred at 80° C. for 3 hours. Water was added thereto under ice cooling and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was purified by silica gel column chromatography (eluent: chloroform), followed by recrystallization from hexane/ethyl acetate to give 216 mg (yield quant.) of Compound 178 as pale yellow grains.

Melting Point: 158.5°–158.9° C.; MS-EI m/e: 437(M$^+$); Elemental Analysis: $C_{22}H_{27}N_7O_3$, Calcd. (%): C, 60.40; H, 6.22; N, 22.41; Found (%): C, 60.15; H, 6.31; N, 22.32; IR (KBr) $v_{max}$ (cm$^{-1}$): 2094, 1653, 1605, 1543, 1515; NMR (270 MHz; CDCl$_3$)δ(ppm): 7.75(1H, d, J=15.5 Hz), 7.53 (2H, d, J=8.6 Hz), 6.92 (2H, d, J=8.6 Hz), 6.77 (1H, d, J=15.5 Hz), 4.21(2H, q, J=6.9 Hz), 4.13–3.69 (4H, m), 4.04 (3H, s), 3.39 (2H, t, J=6.6 Hz), 1.93

1.79(4H, m), 1.38(3H, t, J=6.9 Hz), 1.26(3H, t, J=6.9 Hz).

REFERENCE EXAMPLE 118

(E)-8-[4-(4-Aminobutoxy)styryl]-1,3-diethyl-7-methylxanthine (Compound 179)

Compound 178 (75 mg, 0.17 mmol) obtained in Reference Example 117 was dissolved in 7.5 ml of tetrahydrofuran. To the solution was added 90 mg (0.34 mmol) of triphenylphosphine, and the mixture was heated under reflux for 3 hours. Water (5 ml) was added thereto and the mixture was heated under reflux for further one hour. After cooling, a 2N aqueous solution of sodium hydroxide was added thereto, and the mixture was extracted with chloroform and dried over anhydrous sodium sulfate, followed by evaporation under reduced pressure. The residue was purified by silica gel column chromatography (eluent: chloroform/methanol/triethylamine) to give 74 mg (yield quant.) of Compound 179. The obtained crude crystals were further recrystallized from 2-propanol/water.

Melting Point: 212.1°–214.5° C.; MS-EI m/e: 411(M$^+$); IR (KBr) $v_{max}$ (cm$^{-1}$): 1692, 1649, 1606, 1544, 1515; NMR (270 MHz; DMSO-d$_6$)δ(ppm): 7.74(2H, d, J=8.6 Hz), 7.62(1H, d, J=16.2 Hz), 7.20(1H, d, J=16.2 Hz), 6.98 (2H, d, J=8.6 Hz), 4.08–3.88(6H, m), 4.02(3H, s), 2.83–2.74(2H, m), 1.82–1.59(4H, m), 1.26(3H, t, J=6.9 Hz), 1.13 (3H, t, J=6.9 Hz).

REFERENCE EXAMPLE 119

(E)-8-(4-Ethoxycarbonylmethoxystyryl)-1,3-diethyl-7-methylxanthine (Compound 180)

Compound 175 (300 mg, 0.88 mmol) obtained in Reference Example 114 was dissolved in 10 ml of dimethylformamide. To the solution were added 731 mg (5.29 mmol) of potassium carbonate and 0.47 ml (4.41 mmol) of ethyl chloroacetate, and the mixture was stirred at room temperature for 2 hours. Water was added thereto to dissolve potassium carbonate and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was recrystallized from hexane/ethyl acetate to give 341 mg (yield 91%) of Compound 180 as pale yellow needles.

Melting Point: 191.8°–192.2° C.; MS-EI m/e: 426(M$^+$); IR (KBr) $v_{max}$ (cm$^{-1}$): 1688, 1658, 1650, 1514, 1440; NMR (270 MHz; CDCl$_3$)δ(ppm): 7.74(1H, d, J=15.8 Hz), 7.54 (2H, d, J=8.6 Hz), 6.94 (2H, d, J=8.6 Hz), 6.79 (1H, d, J=15.8 Hz), 4.66(2H, s), 4.29(2H, q, J=6.9 Hz), 4.21 (2H, q, J=6.9 Hz), 4.09 (2H, q, J=6.9 Hz), 4.04(3H, s), 1.38(3H, t, J=6.9 Hz), 1.31 (3H, t, J=6.9 Hz), 1.26(3H, t, J=6.9 Hz).

REFERENCE EXAMPLE 120

(E)-8-(4-Carboxymethoxystyryl)-1,3-diethyl-7-methylxanthine (Compound 181)

Compound 180 (200 mg, 0.47 mmol) obtained in Reference Example 119 was dissolved in a mixed solvent of 4 ml of tetrahydrofuran, 4 ml of ethanol, and 2 ml of water. To the solution was added 98 mg (2.34 mmol) of lithium hydroxide monohydrate, and the mixture was stirred at room temperature for one hour. To the reaction solution was added 2N hydrochloric acid, and the mixture was extracted with chloroform and dried over anhydrous sodium sulfate, followed by evaporation under reduced pressure. The residue was purified by silica gel column chromatography (eluent: chloroform/methanol/acetic acid) to give 40 mg (yield 21%) of Compound 181 as a pale yellow solid.

Melting Point: 267.5–269.0° C.; MS-EI m/e: 398(M$^+$); IR (KBr) $v_{max}$ (cm$^{-1}$): 1684, 1653, 1647, 1515; NMR (270 MHz; DMSO-d$_6$)δ(ppm): 7.74(2H, d, J=8.6 Hz), 7.62(1H, d, J=15.8 Hz), 7.20(1H, d, J=15.8 Hz), 6.96 (2H, d, J=8.6 Hz), 4.70(2H, s), 4.07(2H, q, J=6.9 Hz), 4.01 (3H, s), 3.92 (2H, q, J=6.9 Hz), 1.26 (3H, t, J=6.9 Hz), 1.13(3H, t, J=6.9 Hz).

REFERENCE EXAMPLE 121

(E)-1,3-Diethyl-8-(3-phenoxystyryl)xanthine (Compound 182)

Substantially the same procedure as in Example 7 was repeated using 3.00 g (15.1 mmol) of 5,6-diamino-1,3-diethyluracil and 4.00 g (16.7 mmol) of 3-phenoxycinnamic acid. Then, the resultant -crude crystals were recrystallized from dioxane/water to give 3.82 g (yield 63%) of Compound 182 as pale yellow needles.

Melting Point: 241.4°–243.4° C.; Elemental Analysis: $C_{23}H_{22}N_4O_3$, Calcd. (%): C, 68.64; H, 5.51; N, 13.92; Found (%): C, 68.26; H, 5.59; N, 13.79; IR (KBr) $v_{max}$ (cm$^{-1}$): 1640, 1579, 1492, 1265; NMR (270 MHz; DMSO-$d_6$)δ(ppm): 13.52(1H, brs), 7.87 (1H, d, J=2.0 Hz), 7.63(1H, dd, J=8.4, 2.0 Hz), 7.56 (1H, d, J=16.3 Hz), 7.16(1H, d, J=8.4 Hz), 6.95(1H, d, J=16.3 Hz), 4.06(2H, q, J=6.9 Hz), 3.93(2H, q, J=6.9 Hz), 3.89(3H, s), 1.26(3H, t, J=6.9 Hz), 1.14 (3H, t, J=6.9 Hz).

REFERENCE EXAMPLE 122

(E)-1,3-Diethyl-7-methyl-8-(3-phenoxystyryl)xanthine (Compound 183)

Substantially the same procedure as in Example 8 was repeated using 2.00 g (4.97 mmol) of Compound 182 obtained in Reference Example 121 in place of Compound 64. Then, the resultant crude crystals were recrystallized from hexane/ethyl acetate to give 1.78 g (yield 86%) of Compound as yellow needles.

Melting Point: 205.1°–205.9° C.; Elemental Analysis: $C_{24}H_{24}N_4O_3$, Calcd. (%): C, 69.22; H, 5.81; N, 13.45; Found (%): C, 69.02; H, 5.80; N, 13.48; IR (KBr) $v_{max}$ (cm$^{-1}$): 1692, 1652, 1492, 1241; NMR (270 MHz; CDCl$_3$)δ(ppm): 7.74 (1H, d, J=15.8 Hz), 7.40–6.98 (9H, m), 6.88(1H, d, J=15.8 Hz), 4.20(2H, q, J=6.9 Hz), 4.09(2H, q, J=6.9 Hz), 4.04(3H, s), 1.37 (3H, t, J=6.9 Hz), 1.26(3H, t, J=6.9 Hz).

REFERENCE EXAMPLE 123

(E)-1,3-Diethyl-8-(4-hydroxystyryl)xanthine (Compound 184)

Substantially the same procedure as in Reference Example 114 was repeated using 500 mg (7.02 mmol) of Compound 144 obtained in Reference Example 87. Then, the resultant crude crystals were recrystallized from dioxane/water to give 430 mg (yield 98%) of Compound 184 as pale yellow needles.

Melting Point: >270° C.; Elemental Analysis: $C_{17}H_{18}N_4O_3$, Calcd. (%): C, 62.57; H, 5.56; N, 17.17; Found (%): C, 62.60; H, 5.50; N, 17.07; IR (KBr) $v_{max}$ (cm$^{-1}$): 1674, 1634, 1520, 1488; NMR (270 MHz; DMSO-$d_6$)δ(ppm): 13.34(1H, brs), 9.77 (1H, s), 7.56(1H, d, J=16.2 Hz), 7.46(2H, d, J=8.6 Hz), 6.81 (2H, d, J=8.6 Hz), 6.80 (1H, d, J=16.2 Hz), 4.06 (2H, q, J=6.9 Hz), 3.94 (2H, q, J=6.9 Hz), 1.26(3H, t, J=6.9 Hz), 1.14(3H, t, J=6.9 Hz).

REFERENCE EXAMPLE 124

(E)-1,3-Diethyl-8-(4-hydroxy-2,3-dimethylstyryl)-7-methylxanthine (Compound 185)

Substantially the same procedure as in Reference Example 112 was repeated using 500 mg (1.31 mmol) of Compound 73 obtained in Example 16. Then, the resultant crude crystals were recrystallized from 2-propanol to give 290 mg (yield 60%) of Compound 185 as a pale yellow powder.

Melting Point: 240.2–242.0° C.; MS-EI m/e: 368(M$^+$); IR (KBr) $v_{max}$ (cm$^{-1}$): 1683, 1656, 1586, 1460; NMR (270 MHz; DMSO-$d_6$)δ(ppm): 10.20(1H, brs), 9.64 (1H, brs), 7.92(1H, d, J=15.6 Hz), 7.57(1H, d, J=8.7 Hz), 6.97(1H, d, J=15.6 Hz), 6.74(1H, d, J=8.7 Hz), 4.07(2H, q, J=6.9 Hz), 3.99(3H, s), 3.91 (2H, q, J=6.9 Hz), 2.29(3H, s), 2.10(3H, s), 1.26 (3H, t, J=6.9 Hz), 1.13(3H, t, J=6.9 Hz).

REFERENCE EXAMPLE 125

(Z)-8-(3,4-Dimethoxystyryl)-7-methyl-1,3-dipropylxanthine (Compound 186)

Compound 1 (1.00 g, 2.42 mmol) obtained in Reference Example 1 was dissolved in 1.6 L of methanol, and the solution was irradiated with sunlight for 5 hours. After evaporation under reduced pressure, the residue was purified by high performance liquid chromatography (column: YMC Pack ODS-A, SH-365-10, S-10; 30 mmφ×500 mm, flow rate: 90 ml/min, detection: UV 246 nm) to give 565 mg (yield 57%) of Compound 186 as white needles.

Melting Point: 126.9°–127.2° C.; Elemental Analysis: $C_{22}H_{28}N_4O_4$, Calcd. (%): C, 64.06; H, 6.84; N, 13.58; Found (%): C, 64.12; H, 7.09; N, 13.54; IR (KBr) $v_{max}$ (cm$^{-1}$): 1696, 1654, 1542, 1521; NMR (270 MHz; DMSO-$d_6$)δ(ppm): 7.28(1H, d, J=8.4 Hz), 7.20(1H, s), 6.94(1H, d, J=12.7 Hz), 6.92(1H, d, J=8.4 Hz), 6.39(1H, d, J=12.7 Hz), 3.93 (2H, t, J=7.4 Hz), 3.84 (2H, t, J=6.9HZ), 3.77(6H, S), 3.64 (3H, S), 1.75–1.50 (4H, m), 0.86 (3H, t, J=7.4 Hz), 0.85 (3H, t, J=7.4 Hz).

REFERENCE EXAMPLE 126

(E)-8-(3,4-Dimethoxystyryl)-7-ethyl-1,3-dipropylxanthine (Compound 187)

Substantially the same procedure as in Reference Example 1 was repeated using 1.5 g (3.77 mmol) of Compound B obtained in Reference Example 1 and 0.60 ml (7.54 mmol) of ethyl iodide. Then, the resultant crude crystals were recrystallized from ethanol/water to give 1.38 g (yield 87%) of Compound 187 as white needles.

Melting Point: 107.6°–107.9° C.; Elemental Analysis: $C_{23}H_{30}N_4O_4$, Calcd. (%): C, 64.77; H, 7.09; N, 13.14; Found (%): C, 64.81; H, 7.28; N, 13.21; IR (KBr) $v_{max}$ (cm$^{-1}$): 1695, 1655, 1515, 1265; NMR (270 MHz; CDCl$_3$)δ(ppm): 7.63(1H, d, J=15.8 Hz), 7.42(1H, d, J=1.7 Hz), 7.32(1H, dd, J=1.7, 8.6 Hz), 7.23(1H, d, J=15.8 Hz), 6.99(1H, d, J=8.6 Hz), 4.51 (2H, q, J=6.9 Hz), 3.99(2H, t, J=7.2 Hz), 3.87–3.80 (2H, m), 3.85(3H, s), 3.80(3H, s), 1.80–1.45(4H, m), 1.33(3H, t, J=6.9 Hz), 0.94–0.85(6H, m).

REFERENCE EXAMPLE 127

(E)-8-(3,4-Dimethoxystyryl)-7-propargyl-1,3-dipropylxanthine (Compound 188)

Substantially the same procedure as in Reference Example 1 was repeated using 1.5 g (3.77 mmol) of Compound B obtained in Reference Example 1 and 0.67 ml (7.54 mmol) of propargyl bromide. Then, the resultant crude crystals were recrystallized from cyclohexane/toluene to give 1.35 g (yield 82%) of Compound 188 as a yellow powder.

Melting Point: 153.4°–154.8° C.; Elemental Analysis: $C_{24}H_{28}N_4O_4$, Calcd. (%): C, 66.04; H, 6.47; N, 12.84; Found (%): C, 66.18; H, 6.74; N, 12.87; IR (KBr) $v_{max}$ (cm$^{-1}$): 1684, 1647, 1510, 1270; NMR (270 MHz; CDCl$_3$)δ(ppm): 7.66(1H, d, J=15.7 Hz), 7.41(1H, d, J=1.3 Hz), 7.32(1H, dd, J=1.3, 8.5 Hz), 7.26(1H, d, J=15.7 Hz), 7.02(1H, d, J=8.5 Hz), 5.43 (2H, d, J=2.0 Hz), 4.00 (2H, t, J=7.3 Hz), 3.87–3.81 (2H, m), 3.85(3H, s), 3.81(3H, s), 3.48(1H, t, J=2.0 Hz), 1.80–1.45(4H, m), 0.94–0.85(6H, m).

REFERENCE EXAMPLE 128

(E)-8-[3,4-Bis(methoxymethoxy)styryl]-7-methyl-1,3-dipropylxanthine (Compound 189)

Compound 53 (300 mg, 0.78 mmol) obtained in Reference Example 46 was dissolved in 6 ml of tetrahydrofuran. To the solution were added 1.64 ml (9.41 mmol) of diisopropylethylamine and 1.64 ml (7.12 mmol) of chloromethylmethyl ether under ice-cooling in a stream of argon, and the mixture was heated under reflux for 3 hours. Ice was added to the reaction solution and the mixture was separated with chloroform-a saturated aqueous saline solution. The organic layer was dried over anhydrous sodium sulfate, followed by evaporation under reduced pressure. The residue was purified by silica gel column chromatography (eluent: hexane/ethyl acetate) and recrystallized from hexane/ethyl acetate to give 211 mg (yield 57%) of Compound 189 as white needles.

Melting Point: 172.2°–172.6° C.; Elemental Analysis: $C_{24}H_{32}N_4O_6$, Calcd. (%): C, 61.01; H, 6.82; N, 11.86; Found (%): C, 61.16; H, 7.00; N, 11.88; IR (KBr) $v_{max}$ (cm$^{-1}$): 1688, 1658, 1509, 1267; NMR (270 MHz; CDCl$_3$)δ(ppm): 7.22(1H, d, J=15.8 Hz), 7.39(1H, d, J=1.3 Hz), 7.25–7.16(2H, m), 6.77(1H, d, J=15.8 Hz), 5.30(2H, s), 5.28(2H, s), 4.13–3.95 (4H, m), 4.04(3H, s), 3.56(3H, s), 3.54(3H, s), 1.91–1.61(4H, m), 1.00(3H, t, J=7.6 Hz), 0.97(3H, t, J=7.6 Hz).

REFERENCE EXAMPLE 129

(E)-1,3-Diallyl-8-(3,4-dimethoxystyryl)xanthine (Compound 190)

Substantially the same procedure as in Reference Example 1 was repeated using 2.9 g (13.1 mmol) of 1,3-diallyl-5,6-diaminouracil and 2.99 g (14.4 mmol) of 3,4-dimethoxycinnamic acid. Then, the resultant crude crystals were recrystallized from dioxane/water to give 2.80 g (yield of Compound 190 as pale yellow flocculent precipitates.

Melting Point: 251.6°–252.4° C.; Elemental Analysis: $C_{21}H_{22}N_4O_3$, Calcd. (%): C, 63.95; H, 5.62; N, 14.20; Found (%): C, 63.67; H, 5.61; N, 14.14; IR (KBr) $v_{max}$ (cm$^{-1}$): 1698, 1644, 1516; NMR (270 MHz; DMSO-d$_6$)δ(ppm): 13.50(1H, brs), 7.58 (1H, d, J=16.3 Hz), 7.27 (1H, d, J=2.0 Hz), 7.13 (1H, dd, J=2.0, 8.4 Hz), 6.99(1H, d, J=8.4 Hz), 6.96(1H, d, J=16.3 Hz), 6.07–5.82 (2H, m), 5.20–5.01 (4H, m), 4.68–4.45(4H, m), 3.82 (3H, s), 3.79 (3H, s).

REFERENCE EXAMPLE 130

(E)-1,3-Diallyl-8-(3,4-dimethoxystyryl)-7-methylxanthine (Compound 191)

Substantially the same procedure as in Reference Example 1 was repeated using 2.30 g (5.84 mmol) of Compound 190 obtained in Reference Example 129 in place of Compound B. Then, the resultant crude crystals were recrystallized from ethanol to give 1.85 g (yield 78%) of Compound 191 as pale yellow flocculent precipitates.

Melting Point: 159.5°–160.0° C.; Elemental Analysis: $C_{22}H_{24}N_4O_3$, Calcd. (%): C, 64.69; H, 5.92; N, 13.72; Found (%): C, 64.50; H, 6.03; N, 13.71; IR (KBr) $v_{max}$ (cm$^{-1}$): 1698, 1658, 1515, 1265; NMR (270 MHz; DMSO-d$_6$)δ(ppm): 7.60(1H, d, J=15.3 Hz), 7.42(1H, d, J=1.5 Hz), 7.29(1H, dd, J=1.5, 8.4 Hz), 7.21(1H, d, J=15.3 Hz), 6.99(1H, d, J=8.4 Hz), 6.05– 5.78 (2H, m), 5.20–5.01 (4H, m), 4.68–4.45 (4H, m), 4.03(3H, s), 3.84(3H, s), 3.80(3H, s).

REFERENCE EXAMPLE 131

(E)-8-(3,4-Dimethoxystyryl)-1,3-dipropyl-2-thioxanthine (Compound 192)

Substantially the same procedure as in Reference Example 1 was repeated using 4.00 g (16.5 mmol) of 5,6-diamino-1,3-dipropyl-2-thiouracil and 3.79 g (18.2 mmol) of 3,4-dimethoxycinnamic acid. Then, the resultant crude crystals were recrystallized from dioxane/water to give 3.16 g (yield 46%) of Compound 192 as yellow needles.

Melting Point: 273.2°–272.4° C.; Elemental Analysis: $C_{21}H_{26}N_4O_3S$, Calcd. (%): C, 60.85; H, 6.32; N, 13.52; Found (%): C, 60.85; H, 6.49; N, 13.64; IR (KBr) $v_{max}$ (cm$^{-1}$): 1675, 1515; NMR (270 MHz; DMSO-d$_6$)δ(ppm): 7.64(1H, d, J=16.5 Hz), 7.30 (1H, s), 7.15 (1H, d, J=8.2 Hz), 7.02 (1H, d, J=16.5 Hz), 6.99 (1H, d, J=8.2 Hz), 4.56 (2H, t, J=7.6 Hz), 4.45(2H, t, J=7.6 Hz), 3.83(3H, s), 3.80 (3H, s), 1.85–1.60(4H, m), 0.98–0.82(6H, m).

REFERENCE EXAMPLE 132

(E)-8-(3,4-Dimethoxystyryl)-7-methyl-1,3-dipropyl-2-thioxanthine (Compound 193)

Substantially the same procedure as in Reference Example 1 was repeated using 3.00 g (7.25 mmol) of Compound 192 obtained in Reference Example 131 in place of Compound B. Then, the resultant crude crystals were recrystallized from toluene/ethanol to give 1.79 g (yield 58%) of Compound 193 as a pale yellow powder.

Melting Point: 137.3°–139.2° C.; Elemental Analysis: $C_{22}H_{28}N_4O_3S$, Calcd. (%): C, 61.66; H, 6.59; N, 13.07; Found (%): C, 61.44; H, 6.71; N, 13.05; IR (KBr) $v_{max}$ (cm$^{-1}$): 1684, 1515, 1438; NMR (270 MHz; DMSO-d$_6$)δ(ppm): 7.67(1H, d, J=15.7 Hz), 7.44 (1H, d, J=1.3 Hz), 7.33(1H, dd, J=1.3, 8.3 Hz), 7.24(1H, d, J=15.7 Hz), 7.00(1H, d, J=8.3 Hz), 4.56 (2H, t, J=7.6 Hz), 4.42 (2H, t, J=7.6 Hz), 4.06 (3H, s), 3.85 (3H, s), 3.81 (3H, s), 1.85–1.60 (4H, m), 0.98–0.82 (6H, m).

REFERENCE EXAMPLE 133

(E)-8-(3-Methoxy-4-methoxymethoxystyryl)-1,3-dipropylxanthine (Compound 194)

Substantially the same procedure as in Reference Example 1 was repeated using 4.0 g (17.7 mmol) of 5,6-diamino-1,3-dipropyluracil and 4.63 g (19.4 mmol) of 3-methoxy-4-methoxymethoxycinnamic acid. Then, the resultant crude crystals were recrystallized from dioxane/water to give 5.06 g (yield 67%) of Compound 194 as pale yellow flocculent precipitates.

Melting Point: 226.7°–227.4° C.; Elemental Analysis: $C_{22}H_{28}N_4O_5$, Calcd. (%): C, 61.67; H, 6.58; N, 13.08; Found (%): C, 61.56; H, 6.68; N, 13.09; IR (KBr) $v_{max}$ (cm$^{-1}$): 1697, 1655, 1650, 1516, 1255; NMR (270 MHz; DMSO-d$_6$)δ(ppm): 13.47(1H, brs), 7.60 (1H, d, J=16.5 Hz), 7.31(1H, s), 7.10(2H, m), 7.00 (1H, d, J=16.5 Hz), 5.19(2H, s), 3.98(2H, t, J=6.9 Hz), 3.88–3.83 (5H, m), 3.40 (3H, s), 1.79–1.66 (2H, m), 1.62–1.51 (2H, m), 0.90 (3H, t, J=7.6 Hz), 0.88 (3H, t, J=7.6Hz).

REFERENCE EXAMPLE 134

(E)-8-(3-Methoxy-4-methoxymethoxystyryl)-7-methyl-1,3-dipropylxanthine (Compound 195)

Substantially the same procedure as in Reference Example 1 was repeated using 4.5 g (10.5 mmol) of Compound 194 obtained in Reference Example 133 in place of Compound B. Then, the resultant crude crystals were recrystallized from hexane/ethyl acetate to give 3.66 g (yield 79%) of Compound 195 as pale yellow flocculent precipitates.

Melting Point: 153.2°–154.9° C.; Elemental Analysis: $C_{23}H_{30}N_4O_5 \cdot 0.3H_2O$, Calcd. (%): C, 61.67; H, 6.89; N, 12.51; Found (%): C, 61.76; H, 6.89; N, 12.47; IR (KBr) $v_{max}$ (cm$^{-1}$): 1697, 1656, 1544, 1254; NMR (270 MHz; CDCl$_3$)δ(ppm): 7.73(1H, d, J=15.8 Hz), 7.20–7.13 (2H, m), 7.10 (1H, m), 6.78 (1H, d, J=15.8 Hz), 5.28 (1H, s), 4.14–4.08 (2H, m), 4.06 (3H, s), 4.01–3.97(2H, m), 3.96(3H, s), 3.53(3H, s), 1.91–1.77 (2H, m), 1.76–1.63 (2H, m), 1.01 (3H, t, J=7.6 Hz) 0.97 (3H, t, J=7.6 Hz).

REFERENCE EXAMPLE 135

(E)-8-(4-Hydroxy-3-methoxystyryl)-1,3-dipropylxanthine (Compound 196)

Compound 194 (1.00 g, 2.33 mmol) obtained in Reference Example 133 was dissolved in 10 ml of tetrahydrofuran. To the solution was added 6 ml of 2N hydrochloric acid, and the mixture was heated under reflux for one hour. The reaction solution was neutralized with a 2N aqueous solution of sodium hydroxide under ice cooling. Water was added thereto, and the deposited crystals were collected by filtration. The obtained crude crystals were recrystallized from methanol/water to give 291 mg (yield 32%) of Compound 196 as a yellow powder.

Melting Point: 243.4°–245.2° C.; Elemental Analysis: $C_{20}H_{24}N_4O_4 \cdot 0.4C_4H_8O_2$, Calcd. (%): C, 61.82; H, 6.53; N, 13.35; Found (%): C, 61.58; H, 6.66; N, 13.55; IR (KBr) $v_{max}$ (cm$^{-1}$): 1699, 1635, 1516 NMR (270 MHz; DMSO-d$_6$)δ(ppm): 13.39 (1H, brs), 9.43 (1H, brs), 7.56(1H, d, J=16.5 Hz), 7.24(1H, d, J=1.7 Hz), 7.01(1H, dd, J=1.7, 8.3 Hz), 6.90(1H, d, J=16.5 Hz), 6.81(1H, d, J=8.3 Hz), 3.98(2H, t, J=7.3 Hz), 3.88–3.84(2H, m), 3.84(3H, s), 1.79–1.65 (2H, m), 1.61–1.50 (2H, m), 0.90 (3H, t, J=7.3 Hz), 0.87(3H, t, J=7.3 Hz).

REFERENCE EXAMPLE 136

(E)-8-(4-Hydroxy-3-methoxystyryl)-7-methyl-1,3-dipropylxanthine (Compound 197)

Substantially the same procedure as in Reference Example 135 was repeated using 3.00 g (6.78 mmol) of Compound 195 obtained in Reference Example 134 in place of Compound 194. Then, the resultant crude crystals were recrystallized from hexane/ethyl acetate to give 1.93 g (yield 72%) of Compound 197 as pale yellow grains.

Melting Point: 186.8°–187.9° C.; Elemental Analysis: $C_{21}H_{26}N_4O_4$, Calcd. (%): C, 63.30; H, 6.57; N, 14.06; Found (%): C, 63.19; H, 6.69; N, 14.25; IR (KBr) $v_{max}$ (cm$^{-1}$): 1693, 1650, 1540, 1520, 1284; NMR (270 MHz; DMSO-d$_6$)δ(ppm): 9.44(1H, brs), 7.57 (1H, d, J=15.5 Hz), 7.39(1H, s), 7.19(1H, d, J=8.3 Hz), 7.13 (1H, d, J=15.5 Hz), 6.81 (1H, d, J=8.3 Hz), 4.01 (3H, s), 3.99(2H, t, J=7.6 Hz), 3.86 (3H, s), 3.84 (2H, t, J=7.6 Hz), 1.77–1.66 (2H, m), 1.63–1.50 (2H, m), 0.90 (3H, t, J=7.6 Hz) 0.87 (3H, t, J=7.6 Hz).

What is claimed is:

1. A xanthine derivative of the formula (I-A):

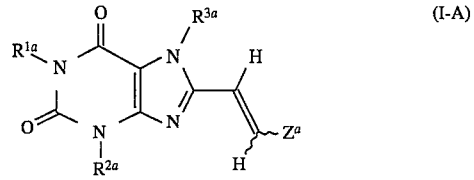

wherein $R^{1a}$ and $R^{2a}$ are independently methyl or ethyl; $R^{3a}$ is hydrogen or lower alkyl; and $Z^a$ is

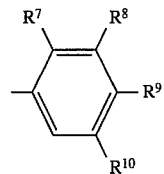

wherein at least one of $R^7$, $R^8$, and $R^9$ is lower alkyl or lower alkoxy and the others represent hydrogen and $R^{10}$ is hydrogen or lower alkyl; or

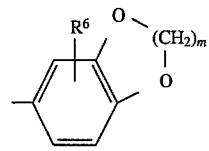

wherein $R^6$ is hydrogen, hydroxy, lower alkyl, lower alkoxy, halogen, nitro or amino, and m is an integer from 1 to 4, or a pharmaceutically acceptable salt thereof.

2. A xanthine derivative of the formula (I-B):

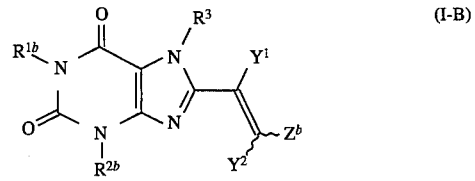

wherein $R^{1b}$ and $R^{2b}$ are independently hydrogen, propyl, butyl, lower alkenyl, or lower alkynyl; $Z^b$ is substituted or unsubstituted naphthyl, or

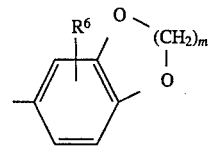

wherein $R^6$ is hydrogen, hydroxy, lower alkyl, lower alkoxy, halogen, nitro or amino, and m is an integer from 1 to 4; and $R^3$ is hydrogen or lower alkyl, $Y^1$ and $Y^2$ are independently hydrogen, halogen or lower alkyl, or a pharmaceutically acceptable salt thereof.

3. A xanthine derivative according to claim 1, in which the configuration at the position 8 of the xanthine ring is (E) form.

4. A xanthine derivative according to claim 3, in which $Z^a$ is

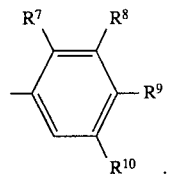

5. A xanthine derivative according to claim 4, in which $R^{3a}$ is lower alkyl.

6. A xanthine derivative according to claim 5, in which $R^{3a}$ is methyl.

7. A xanthine derivative according to claim 6, wherein one of $R^7$, $R^8$, and $R^9$ is methyl, methoxy, ethoxy, or propoxy and the others represent hydrogen; and $R^{10}$ is hydrogen or methyl.

8. A xanthine derivative according to claim 7, in which $R^1$ and $R^2$ are ethyl; $R^8$ and $R^9$ are methoxy; and $R^7$ and $R^{10}$ are hydrogen.

9. A xanthine derivative according to claim 3, in which $Z^a$ is

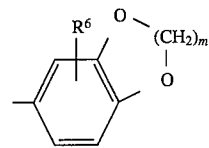

; $R^{3a}$ is methyl; $R^6$ is hydrogen or methoxy; and m is 1 or 2.

10. A xanthine derivative according to claim 9, in which $R^1$ and $R^2$ are ethyl; $R^6$ is 3-methoxy; and m is 1.

11. A xanthine derivative according to claim 2, in which $Z^b$ is

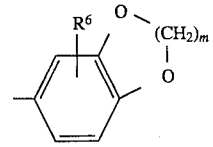

; $R^{1b}$ and $R^2$ are propyl; $R^{3b}$ is methyl; $R^6$ is hydrogen; and m is 2.

* * * * *

UNITED STATES PATENT AND TRADEMARK OFFICE
CERTIFICATE OF CORRECTION

PATENT NO. : 5,484,920
DATED : January 16, 1996
INVENTOR(S) : Fumio Suzuki, et al.

It is certified that error appears in the above-indentified patent and that said Letters Patent is hereby corrected as shown below:

Col. 119, line 19, change "$R^1$" to --$R^{1a}$--;

Col. 119, line 20, change "$R^2$" to --$R^{2a}$--;

Col. 120, line 11, change "$R^1$" to --$R^{1a}$--; and "$R^2$" to --$R^{2a}$--;

Col. 120, line 22, change "$R^2$" to --$R^{2b}$--, and "$R^{3b}$" to --$R^3$--.

Signed and Sealed this

Twenty-second Day of July, 1997

Attest:

*Attesting Officer*

BRUCE LEHMAN

*Commissioner of Patents and Trademarks*

UNITED STATES PATENT AND TRADEMARK OFFICE
Certificate

Patent No. 5,484,920                                           Patented: January 16, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Fumio Suzuki, Mishima (JP); Junichi Shimada, Shizuoka (JP); Nobuaki Koike, Shizuoka (JP); Joji Nakamura, Shizuoka (JP); Shizuo Shioazaki, Fuji (JP); Shunji Ichikawa, Shizuoka (JP); and Hiromi Nonaka, Shizuoka (JP).

Signed and Sealed this Sixth Day of January 2009.

JAMES O. WILSON
*Supervisory Patent Examiner*
Art Unit 1624